(12) United States Patent
Tinsley et al.

(10) Patent No.: US 6,518,413 B1
(45) Date of Patent: Feb. 11, 2003

(54) UTROPHIN GENE EXPRESSION

(75) Inventors: Jonathon M. Tinsley, Oxford (GB); Kay E. Davies, Oxford (GB)

(73) Assignee: Medical Research Council, London (GB)

( * ) Notice: Subject to any disclaimer, the term of this patent is extended or adjusted under 35 U.S.C. 154(b) by 0 days.

(21) Appl. No.: 09/091,501

(22) PCT Filed: Dec. 19, 1996

(86) PCT No.: PCT/GB96/03156

§ 371 (c)(1), (2), (4) Date: Jul. 14, 1998

(87) PCT Pub. No.: WO97/22696

PCT Pub. Date: Jun. 26, 1997

(30) Foreign Application Priority Data

Dec. 19, 1995 (GB) ............................................. 9525962
Jul. 26, 1996 (GB) ............................................. 9615797
Oct. 24, 1996 (GB) ............................................. 9622174

(51) Int. Cl.[7] ............................................. C07H 21/02
(52) U.S. Cl. .................... 536/23.1; 536/24.1; 536/23.5; 435/69.1; 435/69.7; 435/6; 435/325; 435/369; 435/320.1; 435/252.3; 435/458; 435/71.1; 530/350; 530/300; 514/12; 514/44; 424/450; 424/93.2; 264/4.1
(58) Field of Search .......................... 435/6, 325, 69.1, 435/369, 320.1, 458, 252.3, 69.7, 71.1; 536/23.1, 24.1, 23.5; 514/44, 12; 424/450, 93.2; 530/300, 350, 324; 264/4.1

(56) References Cited

FOREIGN PATENT DOCUMENTS

WO    WO 95/30009    * 11/1995

OTHER PUBLICATIONS

Alignments*
Winder et al, "Utrophin actin binding domain: analysis of actin binding and cellular targeting", Journal of Cell Science 108:63–71 (1995).
Love et al, "An autosomal transcript in skeletal muscle with homology to dystrophin", Nature 339:55–58 (1989).
Blake et al, "G–utrophin, the autosomal homologue of dystrophin Dp116, is expressed in sensory ganglia and brain", Proc. Natl. Acad. Sci. USA 92:3697–3701 (1995).
Love et al, "An autosomal transcript in skeletal muscle with homology to dystrophin", Nature 339:55–58 (1989).
Tinsley et al, "Primary structure of dystrophin–related protein", Nature 360:591–593 (1992).
Phelps et al, "Expression of full–length and truncated dystrophin mini–genes in transgenic *mdx* mice", Human Molecular Genetics 4(8):1251–1258 (1995).
Tinsley et al, "Amelioration of the dystrophic phenotype of *mdx* mice using a truncated utrophin transgene", Nature 384:349–353 (1996).
Love et al, "Dystrophin and Dystrophin–Related Proteins: A Review of Protein and RNA Studies", Neuromuscular Disorders 3(1):5–21 (1993).
Koenig et al, "The Complete Sequence of Dystrophin Predicts a Rod–Shaped Cytoskeletal Protein", Cell 53:219–228 (1988).
Tinsley and Davies, "Utrophin: A Potential Replacement for Dystrophin?", Neuromuscular Disord. 3(5/6):537–539 (1993).
Thi Man et al, "Full–length and short forms of utrophin, the dystrophin–related protein", FEBS Letters 358(3):262–266 (1995).

* cited by examiner

*Primary Examiner*—Karen Cochrane Carlson
*Assistant Examiner*—Hope A. Robinson
(74) *Attorney, Agent, or Firm*—Nixon & Vanderhye P.C.

(57) ABSTRACT

Nucleic acid from which a polypeptide with utrophin function can be expressed, especially mini-genes and chimaeric constructs. Expression significantly decreases the severity of the dystrophic muscle phenotype in an animal model, indicating usefulness in treatment of muscular dystrophy. The nucleic acid and encoded polypeptides are also useful in screening for substances to modulate utrophin binding to actin and/or the dystrophin protein complex.

35 Claims, 25 Drawing Sheets

Figure 1a

Region with the actin binding which was unclonable in human.

Figure 1b    Sequence of 2nd unclonable region in human

Figure 3a

```
                  M  A  K  Y  G  E  H  E  A  S  P  D  N  G  Q  N  E
   1  ACTAGTCAAGATGGCCAAGTATGGAGAACATGAAGCCAGTCCTGACAATGGGCAGAACGA         60

F  S  D  I  I  E  S  R  S  D  E  H  N  D  V  Q  K  K  T  F
  61  ATTCAGTGACATCATTGAGTCCAGATCTGATGAACACAATGATGTACAGAAGAAAACCTT        120

T  K  W  I  N  A  R  F  S  K  S  G  K  P  P  I  S  D  M  F
 121  TACCAAATGGATAAACGCTCGATTTTCCAAGAGTGGGAAACCACCCATCAGTGATATGTT        180

S  D  L  K  D  G  R  K  L  L  D  L  L  E  G  L  T  G  T  S
 181  CTCAGACCTCAAAGATGGGAGAAAGCTCTTGGATCTTCTCGAAGGCCTCACAGGAACATC        240

L  P  K  E  R  G  S  T  R  V  H  A  L  N  N  V  N  R  V  L
 241  ATTGCCAAAGGAACGTGGTTCCACAAGGGTGCATGCCTTAAACAATGTCAACCGAGTGCT        300

Q  V  L  H  Q  N  N  V  D  L  V  N  I  G  G  T  D  I  V  D
 301  ACAGGTTTTACATCAGAACAATGTGGACTTGGTGAATATTGGAGGCACGGACATTGTGGA        360

G  N  P  K  L  T  L  G  L  L  W  S  I  I  L  H  W  Q  V  K
 361  TGGAAATCCCAAGCTGACTTTAGGGTTACTCTGGAGCATCATTCTGCACTGGCAGGTGAA        420

D  V  M  K  D  I  M  S  D  L  Q  Q  T  N  S  E  K  I  L  L
 421  GGATGTCATGAAAGATATCATGTCAGACCTGCAGCAGACAAACAGCGAGAAGATCCTGCT        480

S  W  V  R  Q  T  T  R  P  Y  S  Q  V  N  V  L  N  F  T  T
 481  GAGCTGGGTGCGGCAGACCACCAGGCCCTACAGTCAAGTCAACGTCCTCAACTTCACCAC        540

S  W  T  D  G  L  A  F  N  A  V  L  H  R  H  K  P  D  L  F
 541  CAGCTGGACCGATGGACTCGCGTTCAACGCCGTGCTCCACCGGCACAAACCAGATCTCTT        600

S  W  D  R  V  V  K  M  S  P  I  E  R  L  E  H  A  F  S  K
 601  CAGCTGGGACAGAGTGGTCAAAATGTCCCCAATTGAGAGACTTGAACATGCTTTTAGCAA        660

A  H  T  Y  L  G  I  E  K  L  L  D  P  E  D  V  A  V  H  L
 661  GGCCCACACTTATTTGGGAATTGAAAAGCTTCTAGATCCTGAAGATGTTGCTGTGCATCT        720

P  X  X  X  X  X  X  X  X  X  X  X  X  V  E  V  L  P  Q  Q
 721  CCCNNNNNNNNNNNNNNNNNNNNNNNNNNNNNNNNNNNNNCCGTTGAGGTGCTTCCTCAGCA      780

V  T  I  D  A  I  R  E  V  E  T  L  P  R  K  Y  K  K  E  C
 781  AGTCACGATAGATGCCATCCGAGAGGTGGAGACTCTCCCAAGGAAGTATAAGAAAGAATG        840

E  E  E  E  I  H  I  Q  S  A  V  L  A  E  E  G  Q  S  P  R
 841  TGAAGAGGAAGAAATTCATATCCAGAGTGCAGTGCTGGCAGAGGAAGGCCAGAGTCCCCG        900

A  E  T  P  S  T  V  T  E  V  D  M  D  L  D  S  Y  Q  I  A
 901  AGCTGAGACCCCTAGCACCGTCACTGAAGTGGACATGGATTTGGACAGCTACCAGATAGC        960

L  E  E  V  L  T  W  L  L  S  A  E  D  T  F  Q  E  Q  D  D
 961  GCTAGAGGAAGTGCTGACGTGGCTGCTGTCCGCGGAGGACACGTTCCAGGAGCAAGATGA       1020

I  S  D  D  V  E  E  V  K  E  Q  F  A  T  H  E  T  F  M  M
1021  CATTTCTGATGATGTCGAAGAAGTCAAAGAGCAGTTTGCTACCCATGAAACTTTTATGAT       1080

E  L  T  A  H  Q  S  S  V  G  S  V  L  Q  A  G  N  Q  L  M
1081  GGAGCTGACAGCACACCAGAGCAGCGTGGGGAGCGTCCTGCAGGCTGGCAACCAGCTGAT       1140

T  Q  G  T  L  S  E  E  E  E  F  E  I  Q  E  Q  M  T  L  L
1141  GACACAAGGGACTCTGTCAGAGGAGGAGGAGTTTGAGATCCAGGAACAGATGACCTTGCT       1200
```

Figure 3b

```
       N  A  R  W  E  A  L  R  V  E  S  M  E  R  Q  S  R  L  H  D
1201   GAATGCAAGGTGGGAGGCGCTCCGGGTGGAGAGCATGGAGAGGCAGTCCCGGCTGCACGA   1260

A  L  M  E  L  Q  K  K  Q  L  Q  Q  L  S  S  W  L  A  L  T
1261   CGCTCTGATGGAGCTGCAGAAGAAACAGCTGCAGCAGCTCTCAAGCTGGCTGGCCCTCAC   1320

E  E  R  I  Q  K  M  E  S  P  P  L  G  D  D  L  P  S  L  Q
1321   AGAAGAGCGCATTCAGAAGATGGAGAGCCCTCCGCTGGGTGATGACCTGCCCTCCCTGCA   1380

K  L  L  Q  E  H  K  S  L  Q  N  D  L  E  A  E  Q  V  K  V
1381   GAAGCTGCTTCAAGAACATAAAAGTTTGCAAAATGACCTTGAAGCTGAACAGGTGAAGGT   1440

N  S  L  T  H  M  V  V  I  V  D  E  N  S  G  E  S  A  T  A
1441   AAATTCCTTAACTCACATGGTGGTGATTGTGGATGAAAACAGTGGGGAGAGTGCCACAGC   1500

L  L  E  D  Q  L  Q  K  L  G  E  R  W  T  A  V  C  R  W  T
1501   TCTTCTGGAAGATCAGTTACAGAAACTGGGTGAGCGCTGGACAGCTGTATGCCGCTGGAC   1560

E  E  R  W  N  R  L  Q  E  I  S  I  L  W  Q  E  L  L  E  E
1561   TGAAGAACGTTGGAACAGGTTGCAAGAAATCAGTATTCTGTGGCAGGAATTATTGGAAGA   1620

Q  C  L  L  E  A  W  L  T  E  K  E  E  A  L  N  K  V  Q  T
1621   GCAGTGTCTGTTGGAGGCTTGGCTCACCGAAAAGGAAGAGGCTTTGAATAAAGTTCAAAC   1680

S  N  F  K  D  Q  K  E  L  S  V  S  V  R  R  L  A  I  L  K
1681   CAGCAACTTTAAAGACCAGAAGGAACTAAGTGTCAGTGTCCGGCGTCTGGCTATATTGAA   1740

E  D  M  E  M  K  R  Q  T  L  D  Q  L  S  E  I  G  Q  D  V
1741   GGAAGACATGGAAATGAAGAGGCAGACTCTGGATCAACTGAGTGAGATTGGCCAGGATGT   1800

G  Q  L  L  S  N  P  K  A  S  K  K  M  N  S  D  S  E  E  L
1801   GGGCCAATTACTCAGTAATCCCAAGGCATCTAAGAAGATGAACAGTGACTCTGAGGAGCT   1860

T  Q  R  W  D  S  L  V  Q  R  L  E  D  S  S  N  Q  V  T  Q
1861   AACACAGAGATGGGATTCTCTGGTTCAGAGACTCGAAGACTCTTCTAACCAGGTGACTCA   1920

A  V  A  K  L  G  M  S  Q  I  P  Q  K  D  L  L  E  T  V  H
1921   GGCGGTAGCGAAGCTCGGCATGTCCCAGATTCCACAGAAGGACCTATTGGAGACCGTTCA   1980

V  R  E  K  G  M  V  K  K  P  K  Q  E  L  P  P  P  L  T  K
1981   TGTGAGAGAAAAGGGGATGGTGAAGAAGCCCAAGCAGGAACTGCCTCCTCCGTTAACAAA   2040

A  E  H  A  M  Q  K  R  S  T  T  E  L  G  E  N  L  Q  E  L
2041   GGCTGAGCATGCTATGCAAAAGAGATCAACCACCGAATTGGGAGAAAACCTGCAAGAATT   2100

R  D  L  T  Q  E  M  E  V  H  A  E  K  L  K  W  L  N  R  T
2101   AAGAGACTTAACTCAAGAAATGGAAGTACATGCTGAAAAACTCAAATGGCTGAATAGAAC   2160

E  L  E  M  L  S  D  K  S  L  S  L  P  E  R  D  K  I  S  E
2161   TGAATTGGAGATGCTTTCAGATAAAAGTCTGAGTTTACCTGAAAGGGATAAAATTTCAGA   2220

S  L  R  T  V  N  M  T  W  N  K  I  C  R  E  V  P  T  T  L
2221   AAGCTTAAGGACTGTAAATATGACATGGAATAAGATTTGCAGAGAGGTGCCTACCACCCT   2280

K  E  C  I  Q  E  P  S  S  V  S  Q  T  R  I  A  A  H  P  N
2281   GAAGGAATGCATCCAGGAGCCCAGTTCTGTTTCACAGACAAGGATTGCTGCTCATCCTAA   2340

V  Q  K  V  V  L  V  S  S  A  S  D  I  P  V  Q  S  H  R  T
2341   TGTCCAAAAGGTGGTGCTAGTATCATCTGCGTCAGATATTCCTGTTCAGTCTCATCGTAC   2400

S  E  I  S  I  P  A  D  L  D  K  T  I  T  E  L  A  D  W  L
2401   TTCGGAAATTTCAATTCCTGCTGATCTTGATAAAACTATAACAGAACTAGCCGACTGGCT   2460
```

Figure 3c

```
            V  L  I  D  Q  M  L  K  S  N  I  V  T  V  G  D  V  E  E  I
2461  GGTATTAATCGACCAGATGCTGAAGTCCAACATTGTCACTGTTGGGGATGTAGAAGAGAT       2520

N  K  T  V  S  R  M  K  I  T  K  A  D  L  E  Q  R  H  P  Q
2521  CAATAAGACCGTTTCCCGAATGAAAATTACAAAGGCTGACTTAGAACAGCGCCATCCTCA       2580

L  D  Y  V  F  T  L  A  Q  N  L  K  N  K  A  S  S  S  D  M
2581  GCTGGATTATGTTTTTACATTGGCACAGAATTTGAAAAATAAAGCTTCCAGTTCAGATAT       2640

R  T  A  I  T  E  K  L  E  R  V  K  N  Q  W  D  G  T  Q  H
2641  GAGAACAGCAATTACAGAAAAATTGGAAAGGGTCAAGAACCAGTGGGATGGCACCCAGCA       2700

G  V  E  L  R  Q  Q  Q  L  E  D  M  I  I  D  S  L  Q  W  D
2701  TGGCGTTGAGCTAAGACAGCAGCAGCTTGAGGACATGATTATTGACAGTCTTCAGTGGGA       2760

D  H  R  E  E  T  E  E  L  M  R  K  Y  E  A  R  L  Y  I  L
2761  TGACCATAGGGAGGAGACTGAAGAACTGATGAGAAAATATGAGGCTCGACTCTATATTCT       2820

Q  Q  A  R  R  D  P  L  T  K  Q  I  S  D  N  Q  I  L  L  Q
2821  TCAGCAAGCCCGACGGGATCCACTCACCAAACAAATTTCTGATAACCAAATACTGCTTCA       2880

E  L  G  P  G  D  G  I  V  M  A  F  D  N  V  L  Q  K  L  L
2881  AGAACTGGGTCCTGGAGATGGTATCGTCATGGCGTTCGATAACGTCCTGCAGAAACTCCT       2940

E  E  Y  G  S  D  D  T  R  N  V  K  E  T  T  E  Y  L  K  T
2941  GGAGGAATATGGGAGTGATGACACAAGGAATGTGAAAGAAACCACAGAGTACTTAAAAAC       3000

S  W  I  N  L  K  Q  S  I  A  D  R  Q  N  A  L  E  A  E  W
3001  ATCATGGATCAATCTCAAACAAAGTATTGCTGACAGACAGAACGCCTTGGAGGCTGAGTG       3060

R  T  V  Q  A  S  R  R  D  L  E  N  F  L  K  W  I  Q  E  A
3061  GAGGACGGTGCAGGCCTCTCGCAGAGATCTGGAAAACTTCCTGAAGTGGATCCAAGAAGC       3120

E  T  T  V  N  V  L  V  D  A  S  H  R  E  N  A  L  Q  D  S
3121  AGAGACCACAGTGAATGTGCTTGTGGATGCCTCTCATCGGGAGAATGCTCTTCAGGATAG       3180

I  L  A  R  E  L  K  Q  Q  M  Q  D  I  Q  A  E  I  D  A  H
3181  TATCTTGGCCAGGGAACTCAAACAGCAGATGCAGGACATCCAGGCAGAAATTGATGCCCA       3240

N  D  I  F  K  S  I  D  G  N  R  Q  K  M  V  K  A  L  G  N
3241  CAATGACATATTTAAAAGCATTGACGGAAACAGGCAGAAGATGGTAAAAGCTTTGGGAAA       3300

S  E  E  A  T  M  L  Q  H  R  L  D  D  M  N  Q  R  W  N  D
3301  TTCTGAAGAGGCTACTATGCTTCAACATCGACTGGATGATATGAACCAAAGATGGAATGA       3360

L  K  A  K  S  A  S  I  R  A  H  L  E  A  S  A  E  K  W  N
3361  CTTAAAAGCAAAATCTGCTAGCATCAGGGCCCATTTGGAGGCCAGCGCTGAGAAGTGGAA       3420

R  L  L  M  S  L  E  E  L  I  K  W  L  N  M  K  D  E  E  L
3421  CAGGTTGCTGATGTCCTTAGAAGAACTGATCAAATGGCTGAATATGAAAGATGAAGAGCT       3480

K  K  Q  M  P  I  G  G  D  V  P  A  L  Q  L  Q  Y  D  H  C
3481  TAAGAAACAAATGCCTATTGGAGGAGATGTTCCAGCCTTACAGCTCCAGTATGACCATTG       3540

K  A  L  R  R  E  L  K  E  K  E  Y  S  V  L  N  A  V  D  Q
3541  TAAGGCCCTGAGACGGGAGTTAAAGGAGAAAGAATATTCTGTCCTGAATGCTGTCGACCA       3600

A  R  V  F  L  A  D  Q  P  I  E  A  P  E  E  P  R  R  N  L
3601  GGCCCGAGTTTTCTTGGCTGATCAGCCAATTGAGGCCCCTGAAGAGCCAAGAAGAAACCT       3660

Q  S  K  T  E  L  T  P  E  E  R  A  Q  K  I  A  K  A  M  R
3661  ACAATCAAAAACAGAATTAACTCCTGAGGAGAGAGCCCAAAAGATTGCCAAAGCCATGCG       3720
```

Figure 3d

```
          K  Q  S  S  E  V  K  E  K  W  E  S  L  N  A  V  T  S  N  W
3721  CAAACAGTCTTCTGAAGTCAAAGAAAAATGGGAAAGTCTAAATGCTGTAACTAGCAATTG    3780

Q  K  Q  V  D  K  A  L  E  K  L  R  D  L  Q  G  A  M  D  D
3781  GCAAAAGCAAGTGGACAAGGCATTGGAGAAACTCAGAGACCTGCAGGGAGCTATGGATGA    3840

L  D  A  D  M  K  E  A  E  S  V  R  N  G  W  K  P  V  G  D
3841  CCTGGACGCTGACATGAAGGAGGCAGAGTCCGTGCGGAATGGCTGGAAGCCCGTGGGAGA    3900

L  L  I  D  S  L  Q  D  H  I  E  K  I  M  A  F  R  E  E  I
3901  CTTACTCATTGACTCGCTGCAGGATCACATTGAAAAAATCATGGCATTTAGAGAAGAAAT    3960

A  P  I  N  F  K  V  K  T  V  N  D  L  S  S  Q  L  S  P  L
3961  TGCACCAATCAACTTTAAAGTTAAAACGGTGAATGATTTATCCAGTCAGCTGTCTCCACT    4020

D  L  H  P  S  L  K  M  S  R  Q  L  D  D  L  N  M  R  W  K
4021  TGACCTGCATCCCTCTCTAAAGATGTCTCGCCAGCTAGATGACCTTAATATGCGATGGAA    4080

L  L  Q  V  S  V  D  D  R  L  K  Q  L  Q  E  A  H  R  D  F
4081  ACTTTTACAGGTTTCTGTGGATGATCGCCTTAAACAGCTTCAGGAAGCCCACAGAGATTT    4140

G  P  S  S  Q  H  F  L  S  T  S  V  Q  L  P  W  Q  R  S  I
4141  TGGACCATCCTCTCAGCATTTTCTCTCTACGTCAGTCCAGCTGCCGTGGCAAAGATCCAT    4200

S  H  N  K  V  P  Y  Y  I  N  H  Q  T  Q  T  T  C  W  D  H
4201  TTCACATAATAAAGTGCCCTATTACATCAACCATCAAACACAGACCACCTGTTGGGACCA    4260

P  K  M  T  E  L  F  Q  S  L  A  D  L  N  N  V  R  F  S  A
4261  TCCTAAAATGACCGAACTCTTTCAATCCCTTGCTGACCTGAATAATGTACGTTTTTCTGC    4320

Y  R  T  A  I  K  I  R  R  L  Q  K  A  L  C  D  L  L  E
4321  CTACCGTACAGCAATCAAAATCCGAAGACTACAAAAAGCACTATGTTTGGATCTCTTAGA    4380

L  S  T  T  N  E  I  F  K  Q  H  K  L  N  Q  N  D  Q  L  L
4381  GTTGAGTACAACAAATGAAATTTTCAAACAGCACAAGTTGAACCAAAATGACCAGCTCCT    4440

S  V  P  D  V  I  N  C  L  T  T  T  Y  D  G  L  E  Q  M  H
4441  CAGTGTTCCAGATGTCATCAACTGTCTGACAACAACTTATGATGGACTTGAGCAAATGCA    4500

K  D  L  V  N  V  P  L  C  V  D  M  C  L  N  W  L  L  N  V
4501  TAAGGACCTGGTCAACGTTCCACTCTGTGTTGATATGTGTCTCAATTGGTTGCTCAATGT    4560

Y  D  T  G  R  T  G  K  I  R  V  Q  S  L  K  I  G  L  M  S
4561  CTATGACACGGGTCGAACTGGAAAAATTAGAGTGCAGAGTCTGAAGATTGGATTAATGTC    4620

L  S  K  G  L  L  E  E  K  Y  R  Y  L  F  K  E  V  A  G  P
4621  TCTCTCCAAAGGTCTCTTGGAAGAAAAATACAGATATCTCTTTAAGGAAGTTGCGGGGCC    4680

T  E  M  C  D  Q  R  Q  L  G  L  L  L  H  D  A  I  Q  I  P
4681  GACAGAAATGTGTGACCAGAGGCAGCTGGGCCTGTTACTTCATGATGCCATCCAGATCCC    4740

R  Q  L  G  E  V  A  A  F  G  G  S  N  I  E  P  S  V  R  S
4741  CCGGCAGCTAGGTGAAGTAGCAGCTTTTGGAGGCAGTAATATTGAGCCTAGTGTTCGCAG    4800

C  F  Q  Q  N  N  N  K  P  E  I  S  V  K  E  F  I  D  W  M
4801  CTGCTTCCAACAGAATAACAATAAACCAGAAATAAGTGTGAAAGAGTTTATAGATTGGAT    4860

H  L  E  P  Q  S  M  V  W  L  P  V  L  H  R  V  A  A  A  E
4861  GCATTTGGAACCACAGTCCATGGTTTGGCTCCCAGTTTTACATCGAGTGGCAGCAGCGGA    4920

T  A  K  H  Q  A  K  C  N  I  C  K  E  C  P  I  V  G  F  R
4921  GACTGCAAAACATCAGGCCAAATGCAACATCTGTAAAGAATGTCCAATTGTCGGGTTCAG    4980
```

Figure 3e

```
             Y  R  S  L  K  H  F  N  Y  D  V  C  Q  S  C  F  F  S  G  R
4981   GTATAGAAGCCTTAAGCATTTTAACTATGATGTCTGCCAGAGTTGTTTCTTTTCGGGTCG         5040

T  A  K  G  H  K  L  H  Y  P  M  V  E  Y  C  I  P  T  T  S
5041   AACAGCAAAAGGTCACAAATTACATTACCCAATGGTGGAATATTGTATACCTACAACATC         5100

G  E  D  V  R  D  F  T  K  V  L  K  N  F  R  S  K  K  Y
5101   TGGGGAAGATGTACGAGACTTCACAAAGGTACTTAAGAACAAGTTCAGGTCGAAGAAGTA         5160

F  A  K  H  P  R  L  G  Y  L  P  V  Q  T  V  L  E  G  D  N
5161   CTTTGCCAAACACCCTCGACTTGGTTACCTGCCTGTCCAGACAGTTCTTGAAGGTGACAA         5220

L  E  T  P  I  T  L  I  S  M  W  P  E  H  Y  D  P  S  Q  S
5221   CTTAGAGACTCCTATCACACTCATCAGTATGTGGCCAGAGCACTATGACCCCTCACAATC         5280

P  Q  L  F  H  D  D  T  H  S  R  I  E  Q  Y  A  T  R  L  A
5281   TCCTCAACTGTTTCATGATGACACCCATTCAAGAATAGAACAATATGCCACACGACTGGC         5340

Q  M  E  R  T  N  G  S  F  L  T  D  S  S  T  T  G  S  V
5341   CCAGATGGAAAGGACTAATGGGTCTTTTCTCACTGATAGCAGCTCCACCACAGGAAGTGT         5400

E  D  E  H  A  L  I  Q  Q  Y  C  Q  T  L  G  G  E  S  P  V
5401   GGAAGACGAGCACGCCCTCATCCAGCAGTATTGCCAAACACTCGGAGGAGAGTCCCCAGT         5460

S  Q  P  Q  S  P  A  Q  I  L  K  S  V  E  R  E  E  R  G  E
5461   GAGCCAGCCGCAGAGCCCAGCTCAGATCCTGAAGTCAGTAGAGAGGGAAGAACGTGGAGA         5520

L  E  R  I  I  A  D  L  E  E  E  Q  R  N  L  Q  V  E  Y  E
5521   ACTGGAGAGGATCATTGCTGACCTGGAGGAAGAACAAAGAAATCTACAGGTGGAGTATGA         5580

Q  L  K  D  Q  H  L  R  R  G  L  P  V  G  S  P  P  E  S  I
5581   GCAGCTGAAGGACCAGCACCTCCGAAGGGGGCTCCCTGTCGGTTCACCGCCAGAGTCGAT         5640

I  S  P  H  H  T  S  E  D  S  E  L  I  A  E  A  K  L  L  R
5641   TATATCTCCCCATCACACGTCTGAGGATTCAGAACTTATAGCAGAAGCAAAACTCCTCAG         5700

Q  H  K  G  R  L  E  A  R  M  Q  I  L  E  D  H  N  K  Q  L
5701   GCAGCACAAAGGTCGGCTGGAGGCTAGGATGCAGATTTTAGAAGATCACAATAAACAGCT         5760

E  S  Q  L  H  R  L  R  Q  L  L  E  Q  P  E  S  D  S  R  I
5761   GGAGTCTCAGCTCCACCGCCTCCGACAGCTGCTGGAGCAGCCTGAATCTGATTCCCGAAT         5820

N  G  V  S  P  W  A  S  P  Q  H  S  A  L  S  Y  S  L  D  P
5821   CAATGGTGTTTCCCCATGGGCTTCTCCTCAGCATTCTGCACTGAGCTACTCGCTTGATCC         5880

D  A  S  G  P  Q  F  H  Q  A  A  G  E  D  L  L  A  P  P  H
5881   AGATGCCTCCGGCCCACAGTTCCACCAGGCAGCGGGAGAGGACCTGCTGGCCCCACCGCA         5940

D  T  S  T  D  L  T  E  V  M  E  Q  I  H  S  T  F  P  S  C
5941   CGACACCAGCACGGATCTCACGGAGGTCATGGAGCAGATTCACAGCACGTTTCCATCTTG         6000

C  P  N  V  P  S  R  P  Q  A  M  *
6001   CTGCCCAAATGTTCCCAGCAGGCCACAGGCAATGTAATCACTAGT  6045
```

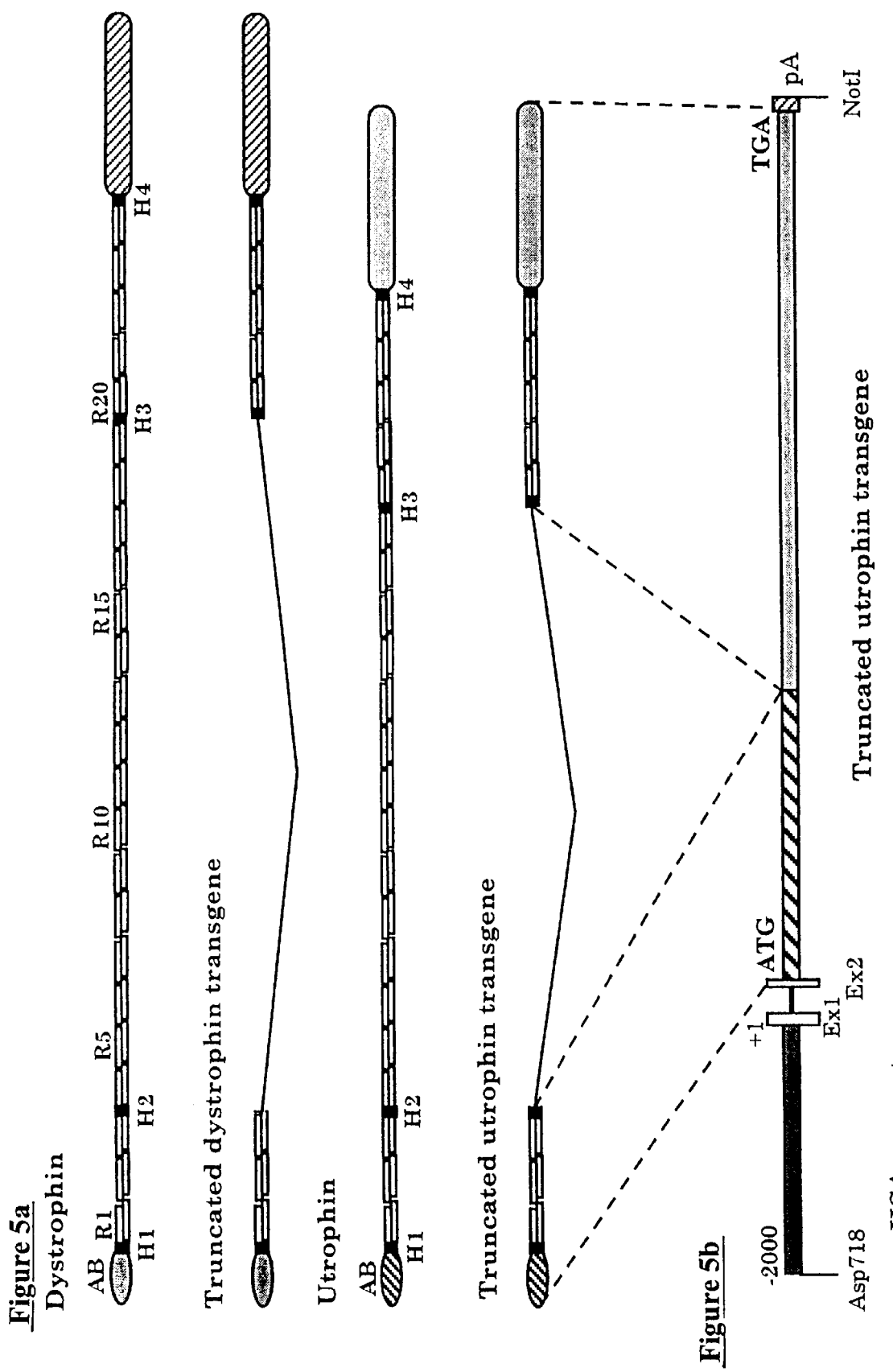

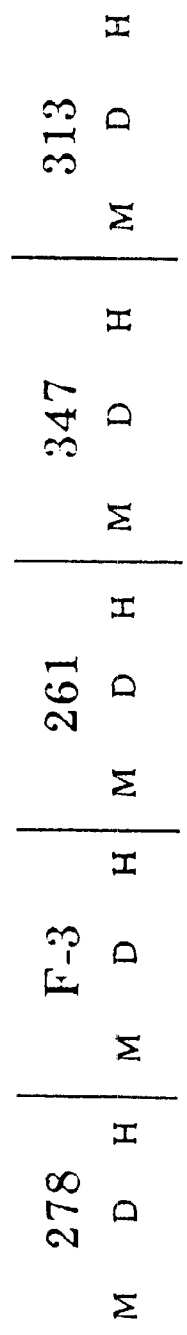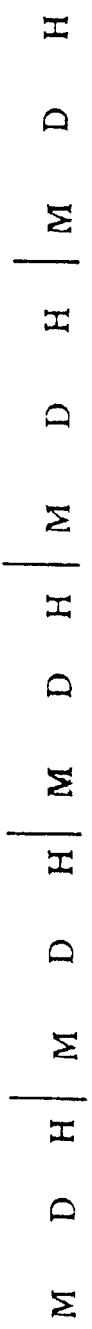
Figure 5c

Figure 9a

```
                        M  A  K  Y  G  E  H  E  A  S  P  D  N  G  Q  N  E
    1   ACTAGTCAAGATGGCCAAGTATGGAGAACATGAAGCCAGTCCTGACAATGGGCAGAACGA       60

F  S  D  I  I  E  S  R  S  D  E  H  N  D  V  Q  K  K  T  F
   61   ATTCAGTGACATCATTGAGTCCAGATCTGATGAACACAATGATGTACAGAAGAAACCTT      120

T  K  W  I  N  A  R  F  S  K  S  G  K  P  P  I  S  D  M  F
  121   TACCAAATGGATAAACGCTCGATTTTCCAAGAGTGGGAAACCACCCATCAGTGATATGTT      180

S  D  L  K  D  G  R  K  L  L  D  L  L  E  G  L  T  G  T  S
  181   CTCAGACCTCAAAGATGGGAGAAAGCTCTTGGATCTTCTCGAAGGCCTCACAGGAACATC      240

L  P  K  E  R  G  S  T  R  V  H  A  L  N  N  V  N  R  V  L
  241   ATTGCCAAAGGAACGTGGTTCCACAAGGGTGCATGCCTTAAACAATGTCAACCGAGTGCT      300

Q  V  L  H  Q  N  N  V  D  L  V  N  I  G  G  T  D  I  V  D
  301   ACAGGTTTTACATCAGAACAATGTGGACTTGGTGAATATTGGAGGCACGGACATTGTGGA      360

G  N  P  K  L  T  G  L  L  W  S  I  I  L  H  W  Q  V  K
  361   TGGAAATCCCAAGCTGACTTTAGGGTTACTCTGGAGCATCATTCTGCACTGGCAGGTGAA      420

D  V  M  K  D  I  M  S  D  L  Q  Q  T  N  S  E  K  I  L  L
  421   GGATGTCATGAAAGATATCATGTCAGACCTGCAGCAGACAAACAGCGAGAAGATCCTGCT      480

S  W  V  R  Q  T  T  R  P  Y  S  Q  V  N  V  L  N  F  T  T
  481   GAGCTGGGTGCGGCAGACCACCAGGCCCTACAGTCAAGTCAACGTCCTCAACTTCACCAC      540

S  W  T  D  G  L  A  F  N  A  V  L  H  R  H  K  P  D  L  F
  541   CAGCTGGACCGATGGACTCGCGTTCAACGCCGTGCTCCACCGGCACAAACCAGATCTCTT      600

S  W  D  R  V  V  K  M  S  P  I  E  R  L  E  H  A  F  S  K
  601   CAGCTGGGACAGAGTGGTCAAAATGTCCCCAATTGAGAGACTTGAACATGCTTTTAGCAA      660

A  H  T  Y  L  G  I  E  K  L  L  D  P  E  D  V  A  V  H  L
  661   GGCCCACACTTATTTGGGAATTGAAAAGCTTCTAGATCCTGAAGATGTTGCTGTGCATCT      720

P  X  X  X  X  X  X  X  X  X  X  X  X  V  E  V  L  P  Q  Q
  721   CCCNNNNNNNNNNNNNNNNNNNNNNNNNNNNNNNNNNNNNNNCCGTTGAGGTGCTTCCTCAGCA   780

V  T  I  D  A  I  R  E  V  E  T  L  P  R  K  Y  K  K  E  C
  781   AGTCACGATAGATGCCATCCGAGAGGTGGAGACTCTCCCAAGGAAGTATAAGAAAGAATG      840

E  E  E  E  I  H  I  Q  S  A  V  L  A  E  E  G  Q  S  P  R
  841   TGAAGAGGAAGAAATTCATATCCAGAGTGCAGTGCTGGCAGAGGAAGGCCAGAGTCCCCG      900

A  E  T  P  S  T  V  T  E  V  D  M  D  L  D  S  Y  Q  I  A
  901   AGCTGAGACCCCTAGCACCGTCACTGAAGTGGACATGGATTTGGACAGCTACCAGATAGC      960

L  E  E  V  L  T  W  L  L  S  A  E  D  T  F  Q  E  Q  D  D
  961   GCTAGAGGAAGTGCTGACGTGGCTGCTGTCCGCGGAGGACACGTTCCAGGAGCAAGATGA     1020

I  S  D  D  V  E  E  V  K  E  Q  F  A  T  H  E  T  F  M  M
 1021   CATTTCTGATGATGTCGAAGAAGTCAAAGAGCAGTTTGCTACCCATGAAACTTTTATGAT     1080

E  L  T  A  H  Q  S  S  V  G  S  V  L  Q  A  G  N  Q  L  M
 1081   GGAGCTGACAGCACACCAGAGCAGCGTGGGGAGCGTCCTGCAGGCTGGCAACCAGCTGAT     1140

T  Q  G  T  L  S  E  E  E  E  F  E  I  Q  E  Q  M  T  L  L
 1141   GACACAAGGGACTCTGTCAGAGGAGGAGGAGTTTGAGATCCAGGAACAGATGACCTTGCT     1200
```

Figure 9b

```
           N  A  R  W  E  A  L  R  V  E  S  M  E  R  Q  S  R  L  H  D
1201  GAATGCAAGGTGGGAGGCGCTCCGGGTGGAGAGCATGGAGAGGCAGTCCCGGCTGCACGA  1260
        A  L  M  E  L  Q  K  K  Q  L  Q  Q  L  S  S  W  L  A  L  T
1261  CGCTCTGATGGAGCTGCAGAAGAAACAGCTGCAGCAGCTCTCAAGCTGGCTGGCCCTCAC  1320
        E  E  R  I  Q  K  M  E  S  P  P  L  G  D  D  L  P  S  L  Q
1321  AGAAGAGCGCATTCAGAAGATGGAGAGCCCTCCGCTGGGTGATGACCTGCCCTCCCTGCA  1380
        K  L  L  Q  E  H  K  S  L  Q  N  D  L  E  A  E  Q  V  K  V
1381  GAAGCTGCTTCAAGAACATAAAAGTTTGCAAAATGACCTTGAAGCTGAACAGGTGAAGGT  1440
        N  S  L  T  H  M  V  V  I  V  D  E  N  S  G  E  S  A  T  A
1441  AAATTCCTTAACTCACATGGTGGTGATTGTGGATGAAAACAGTGGGGAGAGTGCCACAGC  1500
        L  L  E  D  Q  L  Q  K  L  G  E  R  W  T  A  V  C  R  W  T
1501  TCTTCTGGAAGATCAGTTACAGAAACTGGGTGAGCGCTGGACAGCTGTATGCCGCTGGAC  1560
        E  E  R  W  N  R  L  Q  E  I  S  I  L  W  Q  E  L  L  E  E
1561  TGAAGAACGTTGGAACAGGTTGCAAGAAATCAGTATTCTGTGGCAGGAATTATTGGAAGA  1620
        Q  C  L  L  E  A  W  L  T  E  K  E  E  A  L  N  K  V  Q  T
1621  GCAGTGTCTGTTGGAGGCTTGGCTCACCGAAAAGGAAGAGGCTTTGAATAAAGTTCAAAC  1680
        S  N  F  K  D  Q  K  E  L  S  V  S  V  R  R  L  A  I  L  K
1681  CAGCAACTTTAAAGACCAGAAGGAACTAAGTGTCAGTGTCCGGCGTCTGGCTATATTGAA  1740
        E  D  M  E  M  K  R  Q  T  L  D  Q  L  S  E  I  G  Q  D  V
1741  GGAAGACATGGAAATGAAGAGGCAGACTCTGGATCAACTGAGTGAGATTGGCCAGGATGT  1800
        G  Q  L  S  N  P  K  A  S  K  K  M  N  S  D  S  E  E  L
1801  GGGCCAATTACTCAGTAATCCCAAGGCATCTAAGAAGATGAACAGTGACTCTGAGGAGCT  1860
        T  Q  R  W  D  S  L  V  Q  R  L  E  D  S  S  N  Q  V  T  Q
1861  AACACAGAGATGGGATTCTCTGGTTCAGAGACTCGAAGACTCTTCTAACCAGGTGACTCA  1920
        A  V  A  K  L  G  M  S  Q  I  P  Q  K  D  L  L  E  T  V  H
1921  GGCGGTAGCGAAGCTCGGCATGTCCCAGATTCCACAGAAGGACCTATTGGAGACCGTTCA  1980
        V  R  E  K  G  M  V  K  K  P  K  Q  E  L  P  P  P  L  G  P
1981  TGTGAGAGAAAAAGGGATGGTGAAGAAGCCCAAGCAGGAACTGCCTCCTCCGTTGGGCCC  2040
        K  K  R  Q  I  H  V  D  I  E  A  K  K  K  F  D  A  I  S  A
2041  AAAGAAGAGACAGATCCATGTGGATATTGAAGCTAAGAAAAAGTTTGATGCTATAAGTGC  2100
        E  L  L  N  W  I  L  K  W  K  T  A  I  Q  T  T  E  I  K  E
2101  AGAGCTGTTGAACTGGATTTTGAAATGGAAAACTGCCATTCAGACCACAGAGATAAAAGA  2160
        Y  M  K  M  Q  D  T  S  E  M  K  K  K  L  K  A  L  E  K  E
2161  GTATATGAAGATGCAAGACACTTCCGAAATGAAAAAGAAGTTGAAGGCATTAGAAAAAGA  2220
        Q  R  E  R  I  P  R  A  D  E  L  N  Q  T  G  Q  I  L  V  E
2221  ACAGAGAGAAAGAATCCCCAGAGCAGATGAATTAAACCAAACTGGACAAATCCTTGTGGA  2280
        Q  M  G  K  E  G  L  P  T  E  E  I  K  N  V  L  E  K  V  S
2281  GCAAATGGGAAAAGAAGGCCTTCCTACTGAAGAAATAAAAAATGTTCTGGAGAAGGTTTC  2340
        S  E  W  K  N  V  S  Q  H  L  E  D  L  E  R  K  I  Q  L  Q
2341  ATCAGAATGGAAGAATGTATCTCAACATTTGGAAGATCTAGAAAGAAAGATTCAGCTACA  2400
        E  D  I  N  A  Y  F  K  Q  L  D  E  L  E  K  V  I  K  T  K
2401  GGAAGATATAAATGCTTATTTCAAGCAGCTTGATGAGCTTGAAAAGGTCATCAAGACAAA  2460
```

Figure 9c

```
         E  E  W  V  K  H  T  S  I  S  E  S  S  R  Q  S  L  P  S  L
2461  GGAGGAGTGGGTAAAACACACTTCCATTTCTGAATCTTCCCGGCAGTCCTTGCCAAGCTT   2520

K  D  S  C  Q  R  E  L  T  N  L  L  G  L  H  P  K  I  E  M
2521  GAAGGATTCCTGTCAGCGGGAATTGACAAATCTTCTTGGCCTTCACCCCAAAATTGAAAT   2580

A  R  A  S  C  S  A  L  M  S  Q  P  S  A  P  D  F  V  Q  R
2581  GGCTCGTGCAAGCTGCTCGGCCCTGATGTCTCAGCCTTCTGCCCCAGATTTTGTCCAGCG   2640

G  F  D  S  F  L  G  R  Y  Q  A  V  Q  E  A  V  E  D  R  Q
2641  GGGCTTCGATAGCTTTCTGGGCCGCTACCAAGCTGTACAAGAGGCTGTAGAGGATCGTCA   2700

Q  H  L  E  N  E  L  K  G  Q  P  G  H  A  Y  L  E  T  L  K
2701  ACAACATCTAGAGAATGAACTGAAGGGCCAACCTGGACATGCATATCTGGAAACATTGAA   2760

T  L  K  D  V  L  N  D  S  E  N  K  A  Q  V  S  L  N  V  L
2761  AACACTGAAAGATGTGCTAAATGATTCAGAAAATAAGGCCCAGGTGTCTCTGAATGTCCT   2820

N  D  L  A  K  V  E  K  A  L  Q  E  K  K  T  L  D  E  I  L
2821  TAATGATCTTGCCAAGGTGGAGAAGGCCCTGCAAGAAAAAAAGACCCTTGATGAAATCCT   2880

E  N  Q  K  P  A  L  H  K  L  A  E  E  T  K  A  L  E  K  N
2881  TGAGAATCAGAAACCTGCATTACATAAACTTGCAGAAGAAACAAAGGCTCTGGAGAAAAA   2940

V  H  P  D  V  E  K  L  Y  K  Q  E  F  D  D  V  Q  G  K  W
2941  TGTTCATCCTGATGTAGAAAAATTATATAAGCAAGAATTTGATGATGTGCAAGGAAAGTG   3000

N  K  L  K  V  L  V  S  K  D  L  H  L  L  E  E  I  A  L  T
3001  GAACAAGCTAAAGGTCTTGGTTTCCAAAGATCTACATTTGCTTGAGGAAATTGCTCTCAC   3060

L  R  A  F  E  A  D  S  T  V  I  E  K  W  M  D  G  V  K  D
3061  ACTCAGAGCTTTTGAGGCCGATTCAACAGTCATTGAGAAGTGGATGGATGGCGTGAAAGA   3120

F  L  M  K  Q  Q  A  A  Q  G  D  D  A  G  L  Q  R  Q  L  D
3121  CTTCTTAATGAAACAGCAGGCTGCCCAAGGAGACGACGCAGGTCTACAGAGGCAGTTAGA   3180

Q  C  S  A  F  V  N  E  I  E  T  I  E  S  S  L  K  N  M  K
3181  CCAGTGCTCTGCATTTGTTAATGAAATAGAAACAATTGAATCATCTCTGAAAAACATGAA   3240

E  I  E  T  N  L  R  S  G  P  V  A  G  I  K  T  W  V  Q  T
3241  GGAAATAGAGACTAATCTTCGAAGTGGTCCAGTTGCTGGAATAAAAACTTGGGTGCAGAC   3300

R  L  G  D  Y  Q  T  Q  L  E  K  L  S  K  E  I  A  T  Q  K
3301  AAGACTAGGTGACTACCAAACTCAACTGGAGAAACTTAGCAAGGAGATCGCTACTCAAAA   3360

S  R  L  S  E  S  Q  E  K  A  A  N  L  K  K  D  L  A  E  M
3361  AAGTAGGTTGTCTGAAAGTCAAGAAAAAGCTGCGAACCTGAAGAAAGACTTGGCAGAGAT   3420

Q  E  W  M  T  Q  A  E  E  E  Y  L  E  R  D  F  E  Y  K  S
3421  GCAGGAATGGATGACCCAGGCCGAGGAAGAATATTTGGAGCGGGATTTTGAGTACAAGTC   3480

P  E  E  L  E  S  A  V  E  E  M  K  R  A  K  E  D  V  L  Q
3481  ACCAGAAGAGCTTGAGAGTGCTGTGGAAGAGATGAAGAGGGCAAAAGAGGATGTGTTGCA   3540

K  E  V  R  V  K  I  L  K  D  N  I  K  L  L  A  A  K  V  P
3541  GAAGGAGGTGAGAGTGAAGATTCTCAAGGACAACATCAAGTTATTAGCTGCCAAGGTGCC   3600

S  G  G  Q  E  L  T  S  E  L  N  V  V  L  E  N  Y  Q  L  L
3601  CTCTGGTGGCCAGGAGTTGACGTCTGAGCTGAATGTTGTGCTGGAGAATTACCAACTTCT   3660

C  N  R  I  R  G  K  C  H  T  L  E  E  V  W  S  C  W  I  E
3661  TTGTAATAGAATTCGAGGAAAGTGCCACACGCTAgagGAGGTCTGGTCTTGTTGGATTGA   3720
```

Figure 9d

```
              L  L  H  Y  L  D  L  E  T  T  W  L  N  T  L  E  E  R  M  K
3721  ACTGCTTCACTATTTGGATCTTGAAACTACCTGGTTAAACACTTTGGAAGAGCGGATGAA  3780

S  T  E  V  L  P  E  K  T  D  A  V  N  E  A  L  E  S  L  E
3781  GAGCACAGAGGTCCTGCCTGAGAAGACGGATGCTGTCAACGAAGCCCTGGAGTCTCTGGA  3840

S  V  L  R  H  P  A  D  N  R  T  Q  I  R  E  L  G  Q  T  L
3841  ATCTGTTCTGCGCCACCCGGCAGATAATCGCACCCAGATTCGAGAGCTTGGCCAGACTCT  3900

I  D  G  G  I  L  D  D  I  I  S  E  K  L  E  A  F  N  S  R
3901  GATTGATGGGGGATCCTGGATGATATAATCAGTGAGAAACTGGAGGCTTTCAACAGCCG  3960

Y  E  D  L  S  H  L  A  E  S  K  Q  I  S  L  E  K  Q  L  Q
3961  ATATGAAGATCTAAGTCACCTGGCAGAGAGCAAGCAGATTTCTTTGGAAAAGCAACTCCA  4020

V  L  R  E  T  D  Q  M  L  Q  V  L  Q  E  S  L  G  E  L  D
4021  GGTGCTGCGGGAAACTGACCAGATGCTTCAAGTCTTGCAAGAGAGCTTGGGGGAGCTGGA  4080

K  Q  L  T  T  Y  L  T  D  R  I  D  A  F  Q  V  P  Q  E  A
4081  CAAACAGCTCACCACATACCTGACTGACAGGATAGATGCTTTCCAAGTTCCACAGGAAGC  4140

Q  K  I  Q  A  E  I  S  A  H  E  L  T  E  E  L  R  R  N
4141  TCAGAAAATCCAAGCAGAGATCTCAGCCCATGAGCTAACCCTAGAGGAGTTGAGAAGAAA  4200

M  R  S  Q  P  L  T  S  P  E  S  R  T  A  R  G  G  S  Q  M
4201  TATGCGTTCTCAGCCCCTGACCTCCCCAGAGAGTAGGACTGCCAGAGGAGGAAGTCAGAT  4260

D  V  L  Q  R  K  L  R  E  V  S  T  K  F  Q  L  F  Q  K  P
4261  GGATGTGCTACAGAGGAAACTCCGAGAGGTGTCCACAAAGTTCCAGCTTTTCCAGAAGCC  4320

A  N  F  E  Q  R  M  L  D  C  K  R  V  L  D  G  V  K  A  E
4321  AGCTAACTTCGAGCAGCGCATGCTGGACTGCAAGCGTGTGCTGGATGGCGTGAAAGCAGA  4380

L  H  V  L  D  V  K  D  V  D  P  D  V  I  Q  T  H  L  D  K
4381  ACTTCACGTTCTGGATGTGAAGGACGTAGACCCTGACGTCATACAGACGCACCTGGACAA  4440

C  M  K  L  Y  K  T  L  S  E  V  K  L  E  V  E  T  V  I  K
4441  GTGTATGAAACTGTATAAAACTTTGAGTGAAGTCAAACTTGAAGTGGAAACTGTGATTAA  4500

T  G  R  H  I  V  Q  K  Q  Q  T  D  N  P  K  G  M  D  E  Q
4501  AACAGGAAGACATATTGTCCAGAAACAGCAAACGGACAACCCAAAAGGGATGGATGAGCA  4560

L  T  S  L  K  V  L  Y  N  D  L  G  A  Q  V  T  E  G  K  Q
4561  GCTGACTTCCCTGAAGGTTCTTTACAATGACCTGGGCGCACAGGTGACAGAAGGAAAACA  4620

D  L  E  R  A  S  Q  L  A  R  K  M  K  K  E  A  A  S  L  S
4621  GGATCTGGAAAGAGCATCACAGTTGGCCCGGAAAATGAAGAAAGAGGCTGCTTCTCTCTC  4680

E  W  L  S  A  T  E  T  E  L  V  Q  K  S  T  S  E  G  L  L
4681  TGAATGGCTTTCTGCTACTGAAACTGAATTGGTACAGAAGTCCACTTCAGAAGGTCTGCT  4740

G  D  L  D  T  E  I  S  W  A  K  N  V  L  K  D  L  E  K  R
4741  TGGTGACTTGGATACAGAAATTTCCTGGGCTAAAAATGTTCTGAAGGATCTGGAAAAGAG  4800

K  A  D  L  N  T  I  T  E  S  S  A  A  L  Q  N  L  I  E  G
4801  AAAAGCTGATTTAAATACCATCACAGAGAGTAGTGCTGCCCTGCAAAACTTGATTGAGGG  4860

S  E  P  I  L  E  E  R  L  C  V  L  N  A  G  W  S  R  V  R
4861  CAGTGAGCCTATTTTAGAAGAGAGGCTCTGCGTCCTTAACGCTGGGTGGAGCCGAGTTCG  4920

T  W  T  E  D  W  C  N  T  L  M  N  H  Q  N  Q  L  E  I  F
4921  TACCTGGACTGAAGATTGGTGCAATACCTTGATGAACCATCAGAACCAGCTAGAAATATT  4980
```

Figure 9e

```
          D  G  N  V  A  H  I  S  T  W  L  Y  Q  A  E  A  L  L  D  E
4981  TGATGGGAACGTGGCTCACATAAGTACCTGGCTTTATCAAGCTGAAGCTCTATTGGATGA  5040

I  E  K  K  P  T  S  K  Q  E  E  I  V  K  R  L  V  S  E  L
5041  AATTGAAAAGAAACCAACAAGTAAACAGGAAGAAATTGTGAAGCGTTTAGTATCTGAGCT  5100

D  D  A  N  L  Q  V  E  N  V  R  D  Q  A  L  I  L  M  N  A
5101  GGATGATGCCAACCTCCAGGTTGAAAATGTCCGCGATCAAGCCCTTATTTTGATGAATGC  5160

R  G  S  S  R  E  L  V  E  P  K  L  A  E  L  N  R  N  F
5161  CCGTGGAAGCTCAAGCAGGGAGCTTGTAGAACCAAAGTTAGCTGAGCTGAATAGGAAGTT  5220

E  K  V  S  Q  H  I  K  S  A  K  L  L  I  A  Q  E  P  L  Y
5221  TGAAAAGGTGTCTCAACATATCAAAAGTGCCAAATTGCTAATTGCTCAGGAACCATTATA  5280

Q  C  L  V  T  T  E  T  F  E  T  G  V  P  F  S  D  L  E  K
5281  CCAATGTTTGGTCACCACTGAAACATTTGAAACTGGTGTGCCTTTCTCTGACTTGGAAAA  5340

L  E  N  D  I  E  N  M  L  K  F  V  E  K  H  L  E  S  S  D
5341  ATTAGAAAATGACATAGAAAATATGTTAAAATTTGTGGAAAAACACTTGGAATCCAGTGA  5400

E  D  E  K  M  D  E  E  S  A  Q  I  E  E  V  L  Q  R  G  E
5401  TGAAGATGAAAAGATGGATGAGGAGAGTGCCCAGATTGAGGAAGTTCTACAAAGAGGAGA  5460

E  M  L  H  Q  P  M  E  D  N  K  K  E  K  I  R  L  Q  L  L
5461  AGAAATGTTACATCAACCTATGGAAGATAATAAAAAAGAAAAGATCCGTTTGCAATTATT  5520

L  L  H  T  R  Y  N  K  I  K  A  I  P  I  Q  Q  R  K  M  G
5521  ACTTTTGCATACTAGATACAACAAAATTAAGGCAATCCCTATTCAACAGAGGAAAATGGG  5580

Q  L  A  S  G  I  R  S  S  L  L  P  T  D  Y  L  V  E  I  N
5581  TCAACTTGCTTCTGGAATTAGATCATCACTTCTTCCTACAGATTATCTGGTTGAAATTAA  5640

K  I  L  L  C  M  D  D  V  E  L  S  L  N  V  P  E  L  N  T
5641  CAAAATTTTACTTTGCATGGATGATGTTGAATTATCGCTTAATGTTCCAGAGCTCAACAC  5700

A  I  Y  E  D  F  S  F  Q  E  D  S  L  K  N  I  K  D  Q  L
5701  TGCTATTTACGAAGACTTCTCTTTTCAGGAAGACTCTCTGAAGAATATCAAAGACCAACT  5760

D  K  L  G  E  Q  I  A  V  I  H  E  K  Q  P  D  V  I  L  E
5761  GGACAAACTTGGAGAGCAGATTGCAGTCATTCATGAAAAACAGCCAGATGTCATCCTTGA  5820

A  S  G  P  E  A  I  Q  I  R  D  T  L  T  Q  L  N  A  K  W
5821  AGCCTCTGGACCTGAAGCCATTCAGATCAGAGATACACTTACTCAGCTGAATGCAAAATG  5880

D  R  I  N  R  M  Y  S  D  R  K  G  C  F  D  R  A  M  E  E
5881  GGACAGAATTAATAGAATGTACAGTGATCGGAAAGGTTGTTTTGACAGGGCAATGGAAGA  5940

W  R  Q  F  H  C  D  L  N  D  L  T  Q  W  I  T  E  A  E  E
5941  ATGGAGACAGTTCCATTGTGACCTTAATGACCTCACACAGTGGATAACAGAGGCTGAAGA  6000

L  L  V  D  T  C  A  P  G  G  S  L  D  L  E  K  A  R  I  H
6001  ATTACTGGTTGATACCTGTGCTCCAGGTGGCAGCCTGGACTTAGAGAAAGCCAGGATACA  6060

Q  Q  E  L  E  V  G  I  S  S  H  Q  P  S  F  A  A  L  N  R
6061  TCAGCAGGAACTTGAGGTGGGCATCAGCAGCCACCAGCCCAGTTTTGCAGCACTAAACCG  6120

T  G  D  G  I  V  Q  K  L  S  Q  A  D  G  S  F  L  K  E  K
6121  AACTGGGGATGGGATTGTGCAGAAACTCTCCCAGGCAGATGGAAGCTTCTTGAAAGAAAA  6180

L  A  G  L  N  Q  R  W  D  A  I  V  A  E  V  K  D  R  Q  P
6181  ACTGGCAGGTTTAAACCAACGCTGGGATGCAATTGTTGCAGAAGTGAAGGATAGGCAGCC  6240
```

Figure 9f

```
          R  L  K  G  E  S  K  Q  V  M  K  Y  R  H  Q  L  D  E  I  I
6241  AAGGCTAAAAGGAGAAAGTAAGCAGGTGATGAAGTACAGGCATCAGCTAGATGAGATTAT  6300

C  W  L  T  K  A  E  H  A  M  Q  K  R  S  T  T  E  L  G  E
6301  CTGTTGGTTAACAAAGGCTGAGCATGCTATGCAAAAGAGATCAACCACCGAATTGGGAGA  6360

N  L  Q  E  L  R  D  L  T  Q  E  M  E  V  H  A  E  K  L  K
6361  AAACCTGCAAGAATTAAGAGACTTAACTCAAGAAATGGAAGTACATGCTGAAAAACTCAA  6420

W  L  N  R  T  E  L  E  M  L  S  D  K  S  L  S  L  P  E  R
6421  ATGGCTGAATAGAACTGAATTGGAGATGCTTTCAGATAAAAGTCTGAGTTTACCTGAAAG  6480

D  K  I  S  E  S  L  R  T  V  N  M  T  W  N  K  I  C  R  E
6481  GGATAAAATTTCAGAAAGCTTAAGGACTGTAAATATGACATGGAATAAGATTTGCAGAGA  6540

V  P  T  T  L  K  E  C  I  Q  E  P  S  S  V  S  Q  T  R  I
6541  GGTGCCTACCACCCTGAAGGAATGCATCCAGGAGCCCAGTTCTGTTTCACAGACAAGGAT  6600

A  A  H  P  N  V  Q  K  V  V  L  V  S  S  A  S  D  I  P  V
6601  TGCTGCTCATCCTAATGTCCAAAAGGTGGTGCTAGTATCATCTGCGTCAGATATTCCTGT  6660

Q  S  H  R  T  S  E  I  S  I  P  A  D  L  D  K  T  I  T  E
6661  TCAGTCTCATCGTACTTCGGAAATTTCAATTCCTGCTGATCTTGATAAAACTATAACAGA  6720

L  A  D  W  L  V  L  I  D  Q  M  L  K  S  N  I  V  T  V  G
6721  ACTAGCCGACTGGCTGGTATTAATCGACCAGATGCTGAAGTCCAACATTGTCACTGTTGG  6780

D  V  E  E  I  N  K  T  V  S  R  M  K  I  T  K  A  D  L  E
6781  GGATGTAGAAGAGATCAATAAGACCGTTTCCCGAATGAAAATTACAAAGGCTGACTTAGA  6840

Q  R  H  P  Q  L  D  Y  V  F  T  L  A  Q  N  L  K  N  K  A
6841  ACAGCGCCATCCTCAGCTGGATTATGTTTTTACATTGGCACAGAATTTGAAAAATAAAGC  6900

S  S  S  D  M  R  T  A  I  T  E  K  L  E  R  V  K  N  Q  W
6901  TTCCAGTTCAGATATGAGAACAGCAATTACAGAAAAATTGGAAAGGGTCAAGAACCAGTG  6960

D  G  T  Q  H  G  V  E  L  R  Q  Q  Q  L  E  D  M  I  I  D
6961  GGATGGCACCCAGCATGGCGTTGAGCTAAGACAGCAGCAGCTTGAGGACATGATTATTGA  7020

S  L  Q  W  D  D  H  R  E  E  T  E  E  L  M  R  K  Y  E  A
7021  CAGTCTTCAGTGGGATGACCATAGGGAGGAGACTGAAGAACTGATGAGAAAATATGAGGC  7080

R  L  Y  I  L  Q  Q  A  R  R  D  P  L  T  K  Q  I  S  D  N
7081  TCGACTCTATATTCTTCAGCAAGCCCGACGGGATCCACTCACCAAACAAATTTCTGATAA  7140

Q  I  L  L  Q  E  L  G  P  G  D  G  I  V  M  A  F  D  N  V
7141  CCAAATACTGCTTCAAGAACTGGGTCCTGGAGATGGTATCGTCATGGCGTTCGATAACGT  7200

L  Q  K  L  L  E  E  Y  G  S  D  D  T  R  N  V  K  E  T  T
7201  CCTGCAGAAACTCCTGGAGGAATATGGGAGTGATGACACAAGGAATGTGAAAGAAACCAC  7260

E  Y  L  K  T  S  W  I  N  L  K  Q  S  I  A  D  R  Q  N  A
7261  AGAGTACTTAAAAACATCATGGATCAATCTCAAACAAAGTATTGCTGACAGACAGAACGC  7320

L  E  A  E  W  R  T  V  Q  A  S  R  R  D  L  E  N  F  L  K
7321  CTTGGAGGCTGAGTGGAGGACGGTGCAGGCCTCTCGCAGAGATCTGGAAAACTTCCTGAA  7380

W  I  Q  E  A  E  T  T  V  N  V  L  V  D  A  S  H  R  E  N
7381  GTGGATCCAAGAAGCAGAGACCACAGTGAATGTGCTTGTGGATGCCTCTCATCGGGAGAA  7440

A  L  Q  D  S  I  L  A  R  E  L  K  Q  Q  M  Q  D  I  Q  A
7441  TGCTCTTCAGGATAGTATCTTGGCCAGGGAACTCAAACAGCAGATGCAGGACATCCAGGC  7500
```

Figure 9g

```
          E  I  D  A  H  N  D  I  F  K  S  I  D  G  N  R  Q  K  M  V
7501  AGAAATTGATGCCCACAATGACATATTTAAAAGCATTGACGGAAACAGGCAGAAGATGGT  7560

K  A  L  G  N  S  E  E  A  T  M  L  Q  H  R  L  D  D  M  N
7561  AAAAGCTTTGGGAAATTCTGAAGAGGCTACTATGCTTCAACATCGACTGGATGATATGAA  7620

Q  R  W  N  D  L  K  A  K  S  A  S  I  R  A  H  L  E  A  S
7621  CCAAAGATGGAATGACTTAAAAGCAAAATCTGCTAGCATCAGGGCCCATTTGGAGGCCAG  7680

A  E  K  W  N  R  L  L  M  S  L  E  E  L  I  K  W  L  N  M
7681  CGCTGAGAAGTGGAACAGGTTGCTGATGTCCTTAGAAGAACTGATCAAATGGCTGAATAT  7740

K  D  E  E  L  K  K  Q  M  P  I  G  G  D  V  P  A  L  Q  L
7741  GAAAGATGAAGAGCTTAAGAAACAAATGCCTATTGGAGGAGATGTTCCAGCCTTACAGCT  7800

Q  Y  D  H  C  K  A  L  R  R  E  L  K  E  K  E  Y  S  V  L
7801  CCAGTATGACCATTGTAAGGCCCTGAGACGGGAGTTAAAGGAGAAGAATATTCTGTCCT   7860

N  A  V  D  Q  A  R  V  F  L  A  D  Q  P  I  E  A  P  E  E
7861  GAATGCTGTCGACCAGGCCCGAGTTTTCTTGGCTGATCAGCCAATTGAGGCCCCTGAAGA  7920

P  R  R  N  L  Q  S  K  T  E  L  T  P  E  E  R  A  Q  K  I
7921  GCCAAGAAGAAACCTACAATCAAAAACAGAATTAACTCCTGAGGAGAGAGCCCAAAAGAT  7980

A  K  A  M  R  K  Q  S  S  E  V  K  E  K  W  E  S  L  N  A
7981  TGCCAAAGCCATGCGCAAACAGTCTTCTGAAGTCAAAGAAAAATGGGAAAGTCTAAATGC  8040

V  T  S  N  W  Q  K  Q  V  D  K  A  L  E  K  L  R  D  L  Q
8041  TGTAACTAGCAATTGGCAAAAGCAAGTGGACAAGGCATTGGAGAAACTCAGAGACCTGCA  8100

G  A  M  D  D  L  D  A  D  M  K  E  A  E  S  V  R  N  G  W
8101  GGGAGCTATGGATGACCTGGACGCTGACATGAAGGAGGCAGAGTCCGTGCGGAATGGCTG  8160

K  P  V  G  D  L  L  I  D  S  L  Q  D  H  I  E  K  I  M  A
8161  GAAGCCCGTGGGAGACTTACTCATTGACTCGCTGCAGGATCACATTGAAAAAATCATGGC  8220

F  R  E  E  I  A  P  I  N  F  K  V  K  T  V  N  D  L  S  S
8221  ATTTAGAGAAGAAATTGCACCAATCAACTTTAAAGTTAAAACGGTGAATGATTTATCCAG  8280

Q  L  S  P  L  D  L  H  P  S  L  K  M  S  R  Q  L  D  D  L
8281  TCAGCTGTCTCCACTTGACCTGCATCCCTCTCTAAAGATGTCTCGCCAGCTAGATGACCT  8340

N  M  R  W  K  L  L  Q  V  S  V  D  D  R  L  K  Q  L  Q  E
8341  TAATATGCGATGGAAACTTTTACAGGTTTCTGTGGATGATCGCCTTAAACAGCTTCAGGA  8400

A  H  R  D  F  G  P  S  S  Q  H  F  L  S  T  S  V  Q  L  P
8401  AGCCCACAGAGATTTTGGACCATCCTCTCAGCATTTTCTCTCTACGTCAGTCCAGCTGCC  8460

W  Q  R  S  I  S  H  N  K  V  P  Y  Y  I  N  H  Q  T  Q  T
8461  GTGGCAAAGATCCATTTCACATAATAAAGTGCCCTATTACATCAACCATCAAACACAGAC  8520

T  C  W  D  H  P  K  M  T  E  L  F  Q  S  L  A  D  L  N  N
8521  CACCTGTTGGGACCATCCTAAAATGACCGAACTCTTTCAATCCCTTGCTGACCTGAATAA  8580

V  R  F  S  A  Y  R  T  A  I  K  I  R  R  L  Q  K  A  L  C
8581  TGTACGTTTTTCTGCCTACCGTACAGCAATCAAAATCCGAAGACTACAAAAAGCACTATG  8640

L  D  L  L  E  L  S  T  T  N  E  I  F  K  Q  H  K  L  N  Q
8641  TTTGGATCTCTTAGAGTTGAGTACAACAAATGAAATTTTCAAACAGCACAAGTTGAACCA  8700

N  D  Q  L  L  S  V  P  D  V  I  N  C  L  T  T  T  Y  D  G
8701  AAATGACCAGCTCCTCAGTGTTCCAGATGTCATCAACTGTCTGACAACAACTTATGATGG  8760
```

Figure 9h

```
          L  E  Q  M  H  K  D  L  V  N  V  P  L  C  V  D  M  C  L  N
8761 ACTTGAGCAAATGCATAAGGACCTGGTCAACGTTCCACTCTGTGTTGATATGTGTCTCAA 8820
          W  L  N  V  Y  D  T  G  R  T  G  K  I  R  V  Q  S  L  K
8821 TTGGTTGCTCAATGTCTATGACACGGGTCGAACTGGAAAAATTAGAGTGCAGAGTCTGAA 8880
          I  G  L  M  S  L  S  K  G  L  L  E  E  K  Y  R  Y  L  F  K
8881 GATTGGATTAATGTCTCTCTCCAAAGGTCTCTTGGAAGAAAAATACAGATATCTCTTTAA 8940
          E  V  A  G  P  T  E  M  C  D  Q  R  Q  L  G  L  L  L  H  D
8941 GGAAGTTGCGGGGCCGACAGAAATGTGTGACCAGAGGCAGCTGGGCCTGTTACTTCATGA 9000
          A  I  Q  I  P  R  Q  L  G  E  V  A  A  F  G  G  S  N  I  E
9001 TGCCATCCAGATCCCCCGGCAGCTAGGTGAAGTAGCAGCTTTTGGAGGCAGTAATATTGA 9060
          P  S  V  R  S  C  F  Q  Q  N  N  N  K  P  E  I  S  V  K  E
9061 GCCTAGTGTTCGCAGCTGCTTCCAACAGAATAACAATAAACCAGAAATAAGTGTGAAAGA 9120
          F  I  D  W  M  H  L  E  P  Q  S  M  V  W  L  P  V  L  H  R
9121 GTTTATAGATTGGATGCATTTGGAACCACAGTCCATGGTTTGGCTCCCAGTTTTACATCG 9180
          V  A  A  A  E  T  A  K  H  Q  A  K  C  N  I  C  K  E  C  P
9181 AGTGGCAGCAGCGGAGACTGCAAAACATCAGGCCAAATGCAACATCTGTAAAGAATGTCC 9240
          I  V  G  F  R  Y  R  S  L  K  H  F  N  Y  D  V  C  Q  S  C
9241 AATTGTCGGGTTCAGGTATAGAAGCCTTAAGCATTTTAACTATGATGTCTGCCAGAGTTG 9300
          F  F  S  G  R  T  A  K  G  H  K  L  H  Y  P  M  V  E  Y  C
9301 TTTCTTTTCGGGTCGAACAGCAAAAGGTCACAAATTACATTACCCAATGGTGGAATATTG 9360
          I  P  T  T  S  G  E  D  V  R  D  F  T  K  V  L  K  N  K  F
9361 TATACCTACAACATCTGGGGAAGATGTACGAGACTTCACAAAGGTACTTAAGAACAAGTT 9420
          R  S  K  K  Y  F  A  K  H  P  R  L  G  Y  L  P  V  Q  T  V
9421 CAGGTCGAAGAAGTACTTTGCCAAACACCCTCGACTTGGTTACCTGCCTGTCCAGACAGT 9480
          L  E  G  D  N  L  E  T  P  I  T  L  I  S  M  W  P  E  H  Y
9481 TCTTGAAGGTGACAACTTAGAGACTCCTATCACACTCATCAGTATGTGGCCAGAGCACTA 9540
          D  P  S  Q  S  P  Q  L  F  H  D  D  T  H  S  R  I  E  Q  Y
9541 TGACCCCTCACAATCTCCTCAACTGTTTCATGATGACACCCATTCAAGAATAGAACAATA 9600
          A  T  R  L  A  Q  M  E  R  T  N  G  S  F  L  T  D  S  S  S
9601 TGCCACACGACTGGCCCAGATGGAAAGGACTAATGGGTCTTTTCTCACTGATAGCAGCTC 9660
          T  T  G  S  V  E  D  E  H  A  L  I  Q  Q  Y  C  Q  T  L  G
9661 CACCACAGGAAGTGTGGAAGACGAGCACGCCCTCATCCAGCAGTATTGCCAAACACTCGG 9720
          G  E  S  P  V  S  Q  P  Q  S  P  A  Q  I  L  K  S  V  E  R
9721 AGGAGAGTCCCCAGTGAGCCAGCCGCAGAGCCCAGCTCAGATCCTGAAGTCAGTAGAGAG 9780
          E  E  R  G  E  L  E  R  I  I  A  D  L  E  E  E  Q  R  N  L
9781 GGAAGAACGTGGAGAACTGGAGAGGATCATTGCTGACCTGGAGGAAGAACAAAGAAATCT 9840
          Q  V  E  Y  E  Q  L  K  D  Q  H  L  R  R  G  L  P  V  G  S
9841 ACAGGTGGAGTATGAGCAGCTGAAGGACCAGCACCTCCGAAGGGGGCTCCCTGTCGGTTC 9900
          P  P  E  S  I  I  S  P  H  H  T  S  E  D  S  E  L  I  A  E
9901 ACCGCCAGAGTCGATTATATCTCCCCATCACACGTCTGAGGATTCAGAACTTATAGCAGA 9960
          A  K  L  L  R  Q  H  K  G  R  L  E  A  R  M  Q  I  L  E  D
9961 AGCAAAACTCCTCAGGCAGCACAAAGGTCGGCTGGAGGCTAGGATGCAGATTTTAGAAGA 10020
```

Figure 9i

```
           H   N   K   Q   L   E   S   Q   L   H   R   L   R   Q   L   L   E   Q   P   E
10021   TCACAATAAACAGCTGGAGTCTCAGCTCCACCGCCTCCGACAGCTGCTGGAGCAGCCTGA   10080

S   D   S   R   I   N   G   V   S   P   W   A   S   P   Q   H   S   A   L   S
10081   ATCTGATTCCCGAATCAATGGTGTTTCCCCATGGGCTTCTCCTCAGCATTCTGCACTGAG   10140

Y   S   L   D   P   D   A   S   G   P   Q   F   H   Q   A   A   G   E   D   L
10141   CTACTCGCTTGATCCAGATGCCTCCGGCCCACAGTTCCACCAGGCAGCGGGAGAGGACCT   10200

L   A   P   P   H   D   T   S   T   D   L   T   E   V   M   E   Q   I   H   S
10201   GCTGGCCCCACCGCACGACACCAGCACGGATCTCACGGAGGTCATGGAGCAGATTCACAG   10260

T   F   P   S   C   C   P   N   V   P   S   R   P   Q   A   M   *
10261   CACGTTTCCATCTTGCTGCCCAAATGTTCCCAGCAGGCCACAGGCAATGTAATCACTAGT   10320
```

Figure 10

|  |  |  |
|---|---|---|
| humutro  | MAKYGEHEASPDNGQNEFSQIIKSRSDEHNDVQKKTFTKHINARFSKSGKPPINQMFTDLKDGRKLLDLLEGLTG | 75 |
| mouseutro | MAKYGEHEASPDNGQNEFSQIIESRSDEHNDVQKKTFTKHINARFSKSGKPPISDMFSDLKDGRKLLDLLEGLTG | 75 |
| ratutro   | MAKYGHLEASPDDGQNQFSQIIKSRSDEHNDVQKKTFTKHINARFSKSGKPPINDMFSDLKDGRKLLDLLEGLTG | 75 |

|  |  |  |
|---|---|---|
| humutro   | TSLPKERGSTRVHALNNVNRVLQYLHQNNVELVNIGGTDIVDGNHKLTLGLLWSIILHWQVKDVMSDLQQT | 150 |
| mouseutro | TSLPKERGSTRVHALNNVNRVLQYLHQNNVELVNIGGTDIVDGNPKLTLGLLWSIILHWQVKDVMKDIMSDLQQT | 150 |
| ratutro   | TSLPKERGSTRVHALNNVNRVLQYLHQNNVELVNIGGTDIVDGNPKLTLGLLWSIILHWQVKDVMKDIMSDLQQT | 150 |

|  |  |  |
|---|---|---|
| humutro   | NSEKILLSWVRQTTRPYSQVNVLNFTTSWTDGLAFNAVLHRHKPDLFSWDKVVKMSPIERLEHAFSKAQTYLGIE | 225 |
| mouseutro | NSEKILLSWVRQTTRPYSQVNVLNFTTSWTDGLAFNAVLHRHKPDLFSWDRVVKMSPIERLEHAFSKAHTYLGIE | 225 |
| ratutro   | NSEKILLSWVRQTTRPYSQVNVLNFTTSWTDGLAFNAVLHRHKPDLFSWDRVVKMSPTERLEHAFSKAHTYLGIE | 225 |

|  |  |  |
|---|---|---|
| humutro   | KLLDPEDVAVRLPQKKSIIMYLTSLFEVLPQQVTIDAIREVETLPRKYKKECEEEAINIQSTAPEEHESPRAET | 300 |
| mouseutro | KLLDPEDVAVHLPXXXXXXVLPQQVTIDAIREVETLPRKYKKECEEEIHIQSAVLAEEGQSPRAET | 300 |
| ratutro   | KLLDPEDVAVQLPQKKSIIMYLTSLFEVLPQQVTIDAIREVETLPRKYKKECEGEEINIQSAVLTEEGQSPRAET | 300 |

UTROPHIN GENE EXPRESSION

The present invention generally relates to the provision of nucleic acid from which a polypeptide with utrophin function can be expressed, especially mini-genes and chimaeric constructs. Expression of a utrophin transgene significantly decreases the severity of the dystrophic muscle phenotype in an animal model.

The severe muscle wasting disorders, Duchenne muscular dystrophy (DMD) and the less debilitating Becker muscular dystrophy (BMD) are due to mutations in the dystrophin gene. Dystrophin is a large cytoskeletal protein which in muscle is located at the cytoplasmic surface of the sarcolemma, the neuromuscular junction (NMJ) and myotendinous junction (MTJ). The protein is composed of four domains: an actin-binding domain (shown in vitro to bind actin), a rod domain containing triple helical repeats, a cysteine rich (CR) domain and a carboxy-terminal (CT) domain. The majority of the CRCT binds to a complex of proteins and glycoproteins (called the dystrophin protein complex, DPC) spanning the sarcolemma. This complex consists of cytoskeletal syntrophins and dystrobrevin, transmembrane, β-dystroglycan, α-, β-δ-, γ-sarcoglycans and extracellular α-dystroglycan. The DPC links to laminin-α2 (merosin) in the extracellular matrix and to the actin cytoskeleton via dystrophin within the cell. The breakdown of the integrity of the DPC due to the loss of, or impairment of dystrophin function, leads to muscle degeneration and the DMD phenotype. The structure of dystrophin and protein interactions within the DPC have been recently reviewed [1,2,3].

There are various approaches which can be adopted for the gene therapy of DMD. These include myoblast transfer, retroviral infection, adenoviral infection and direct injection of plasmid DNA. In most cases the dystrophin gene used in the experiments generates a truncated protein approximately half the size of the full size protein. This dystrophin minigene was modelled on a natural mutation identified in a very mild Becker patient [4]. The cloned version of this truncated minigene is able to reverse the pathological phenotype in the dystrophin deficient mdx mouse [5,6,7] and has had limited success when delivered to mdx muscle by viral vectors [8,9,10]. Although some progress is being made in each of these areas using the mdx mouse as a model system, there are problems related to the number of muscle cells that can be made dystrophin positive, the levels of expression of the gene and the duration of expression [11]. Another problem to be addressed is the rejection of cells expressing dystrophin because of immunological intolerance i.e. dystrophin within these cells will appear foreign to the host immune system given that most DMD patients will never have expressed dystrophin [12,13].

In order to circumvent some of these problems, possibilities of compensating for dystrophin loss using a related protein, utrophin, are being explored.

Utrophin is a 395 kDa protein encoded by a gene located on chromosome 6q24 and shown to have strong sequence similarity to dystrophin [14]. The actin binding domain of dystrophin and utrophin has 85% similarity and the DPC binding region has 88% similarity. Both of these domains have been shown to function as predicted in vitro. The structure and potential protein interactions are described in detail in reviews [1,2,3].

There is a substantial body of evidence demonstrating that utrophin is capable of localising to the sarcolemma. During normal fetal muscle development there is increased utrophin expression, localised to the sarcolemma up until 18 weeks and 20 days gestation in human and mouse respectively. After this time the utrophin sarcolemmal staining steadily decreases to the significantly lower adult levels shortly before birth where utrophin is localised almost exclusively to the NMJ and MTJ [15,16,17]. The decrease in utrophin expression coincides with increased expression of dystrophin [17]. Many studies have shown that utrophin is bound to the sarcolemma in DMD and BMD patients. However the levels of utrophin localised at the sarcolemma vary from report to report [18,19,20,21]. In some other non Xp21 myopathies, utrophin and dystrophin are simultaneously bound to the sarcolemma of adult skeletal muscle [22].

High levels of utrophin may protect muscle from the consequences of dystrophin loss. Matsumara et al. [23] demonstrated that purified membranes from the mdx mouse contained complexes of utrophin and the DPC. When quadricep muscles (which show necrosis) from these mice were analysed by immunoblotting, the level of utrophin remained approximately the same, however the level of the α-dystroglycan was drastically reduced. In cardiac muscle (which shows no pathology) the level of utrophin was elevated four fold with no loss of the α-dystroglycan. Immunocytochemical analysis of other mdx small calibre skeletal muscles (extraocular and toe) which also have no pathology shows increased utrophin expression and normal levels of α-sarcoglycan. This result suggests that the increased levels of utrophin interacts with the DPC (or an antigenically related complex) at the sarcolemma and prevents loss of the complex thus the structure of these cells remains normal. In the mdx mouse, utrophin levels in muscle remain elevated soon after birth compared with normal mice; however once the utrophin levels have decreased to the adult levels (about 1 week after birth), the first signs of muscle fibre necrosis are detected [15,16].

Thus, in certain circumstances utrophin can localise to the sarcolemma probably at the same binding sites as dystrophin, namely actin and the DPC. If the expression of utrophin is high enough, it may maintain the DPC and thus alleviate the DMD phenotype. It is unlikely that such external upregulation could be tightly controlled giving rise to potentially high levels of utrophin within the cell. However, this may not be a problem as Cox et al. [24] have demonstrated that gross over expression of dystrophin in the muscle of transgenic mdx mice reverts the muscle pathology to normal with no obvious detrimental side effects.

The present invention has arisen from cloning of nucleic acid encoding utrophin and fragments of utrophin from various species. The original aim was to clone nucleic acid encoding human utrophin, but major problems were encountered. A previous paper (14) reported the amino acid sequence of utrophin (so-called "dystrophin-related protein"), obtained by cloning of overlapping cDNAs. However, two regions around the amino terminal actin binding domain were not represented in these clones. These regions could be amplified by PCR and sequenced, but it has proved not to be possible to clone them. Either clones which should have included these regions were rearranged (as determined by restriction mapping) or simply no clones were isolated even if highly recombination deficient E. coli host strains (SURE and STBL2) were used. The gaps in the sequence were identified by comparing the sequence generated from the utrophin cDNAs to the published human dystrophin sequence. It became apparent as further utrophin clones were isolated, none spanned these two gaps.

Sequence information obtained from the amino terminus of the human cDNA was used to design probes and rat and mouse cDNA libraries were screened. Rat cDNAs were also unstable or rearranged in the region corresponding to the unclonable regions in the human sequence. Some large rat clones covering these regions were obtained, but all attempts to generate subclones failed due to rearrangements of the inserts as determined by restriction mapping. Surprisingly, in view of the difficulties with the human and rat sequences, cDNA from the mouse library, covering the regions in question, was found to be stable and amenable to further manipulation including the. generation of smaller subclones.

Figure 1B:
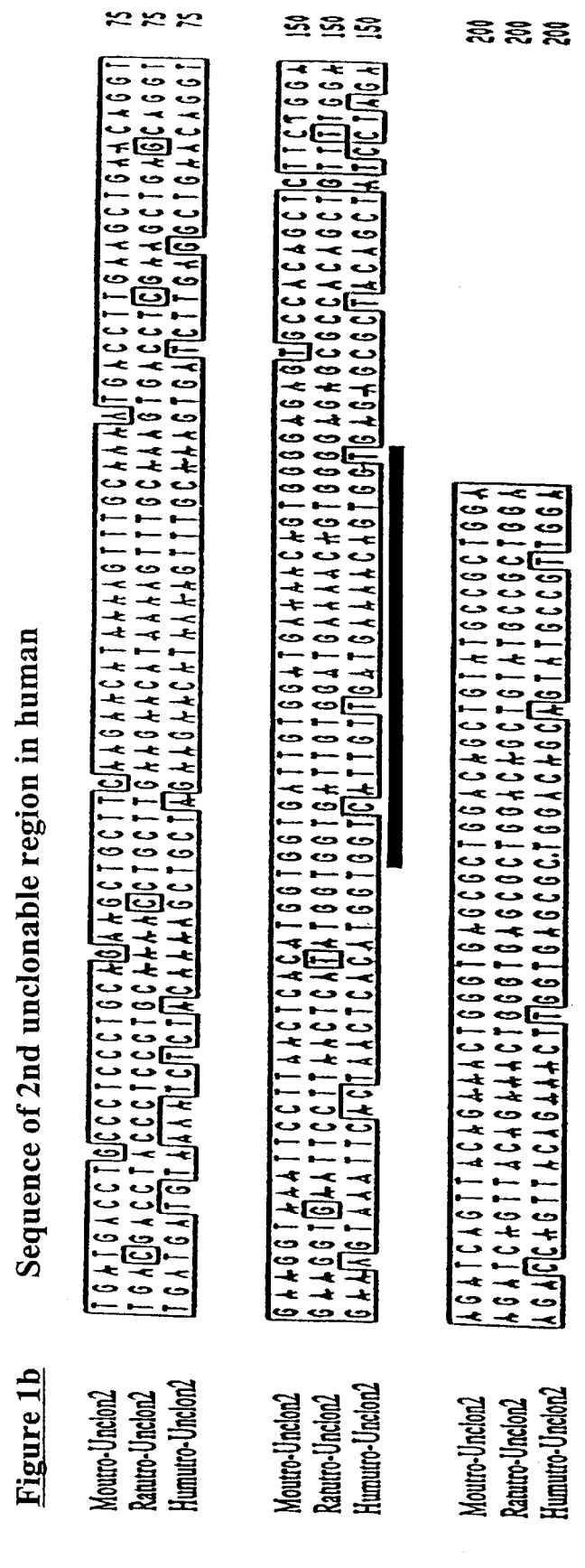

FIG. 1 shows a comparison between human, rat and mouse utrophin nucleotide sequences encoding part of the amino-terminal portion of the respective proteins. The unclonable regions of the human gene are underlined.

This cloning work enables for the first time the construction of a nucleic acid molecule from which a polypeptide with utrophin function can be expressed.

Furthermore, by way of analogy with the success achieved with a dystrophin mini-gene (from which a truncated version of dystrophin is expressed) the present invention provides "utrophin mini-genes" and polypeptides encoded thereby. To overcome the problem of unclonability of regions of the human utrophin gene sequence, the present inventors have realised that it is possible to employ a sequence of nucleotides derived from the mouse utrophin gene in a chimaeric construct to provide for expression of a polypeptide with utrophin function.

According to a first aspect of the present invention there is provided a nucleic acid molecule comprising a sequence of nucleotides encoding a polypeptide with utrophin function.

A potypetide with utrophin function is able to bind actin and able to bind the dystrophin protein complex (DPC).

Polypeptides with utrophin function are generally distinguishable immunologically from dystrophin polypeptides. For example, they may comprise at least one epitope not found in dystrophin. Polypeptides with utrophin function may be identified using specific polyclonal or monoclonal antibodies which do not cross-react with dystrophin. If a polypeptide is able to bind actin and able to bind the dystrophin protein complex and at least one antibody can bind it which cannot bind dystrophin, then the polypeptide has utrophin function. In a preferred embodiment, the polypeptide can be bound by an antibody which binds utrophin but not dystrophin, in other words the polypeptide shares at least one epitope with utrophin which epitope is not found in dystrophin. In another embodiment, the polypeptide does not contain an epitope found in dystrophin, such that the polypeptide is not bound by an antibody which binds dystrophin. In such a case, the epitope recognised by the antibody which binds dystrophin may be one not found in utrophin. The polypeptide may contain no epitope found in dystrophin. The immunological comparison may be made with human utrophin and/or dystrophin, especially if the polypeptide with utrophin function is intended for human use, or with the utrophin and/or dystrophin of the species in which use is intended, e.g. mouse. Mouse monoclonal antibodies MANCH07 and MANNUT1 [31] were used in the work described herein. Standard in vitro binding assays may be used to assess immunological cross-reactivity of a polypeptide.

Thus, the polypeptide comprises an actin-binding domain and a dystrophin protein complex (DPC)-binding domain and utrophin-like as opposed to dystrophin-like, e.g. as determined immunologically.

Preferably the encoding sequence comprises a human sequence, i.e. a sequence obtainable from the genome of a human cell.

Comparison of various amino acid sequences reveals the following % similarities (calculated using the method of Needleman and Wunsch (1974) *J. Mol. Biol.* 48: 443–453, performed using the GAP program from the Winsconsin Package v8, Genetics Computer Group, 575 Science Drive, Madison, Wis. 53711, USA) and identities:

full length human dystrophin v. human utrophin 69% similarity, 50.7% identity;

full length human utrophin v. rat utrophin 93.2% similarity, 87.1% identity;

full length human dystrophin v. mouse dystrophin 95.4% similarity, 91.2% identity;

human dystrophin C-terminus v. human utrophin C-terminus 84.1% similarity, 73.6% identity.

As noted, the present invention is only concerned with "utrophin-like" molecules, not "dystrophin-like" molecules. Thus, polypeptides according to the present invention (e.g. as encoded by nucleic acid according to the invention) may have an amino acid sequence which is greater than about 75% similar, preferably greater than about 80%, about 85%, about 90%, about 95% or about 98% similarity to the amino acid sequence of FIG. 3 or the amino acid sequence of FIG. 9, taken over the full length. The polypeptides may have an amino acid identity of greater than about 55% identity, preferably greater than about 60% identity, about 70%, about 80%, about 90%, about 95% or about 98% identity over the full-length. The levels of similarity and/or identity may be lower outside the C-terminal, DPC-binding domain provided the DPC-binding domain has greater than about 85% similarity, preferably greater than about 90%, about 95% or about 98% similarity with the DPC-binding domain amino acid sequence of FIG. 3 or FIG. 9, or has greater than about 80%, preferably greater than about 85%, about 90%, about 95% or about 98% identity with the DPC-binding domain amino acid sequence of FIG. 3 or FIG. 9. Particular amino acid sequence variants or derivatives may have a sequence which differs from the sequence of FIG. 3 or FIG. 9 by one or more of insertion, addition, substitution or deletion of 1 amino acid, 2, 3, 4, 5–10, 10–20, 20–30, 30–50, 50–100, 100–150, or more than 150 amino acids.

The nucleic acid molecule may be an isolate, or in an isolated and/or purified form, that is to say not in an environment in which it is found in nature, removed from its natural environment. It may be free from other nucleic acid obtainable from the same species, e.g. encoding another polypeptide.

The nucleic acid molecule may be one which is not found in nature. For example, the sequence of nucleotides may form part of a cloning vector and/or an expression vector, as discussed further below. The sequence of nucleotides may represent a variant or derivative of a naturally occurring sequence by virtue of comprising an addition, insertion, deletion and/or substitution of one or more nucleotides with respect to the natural sequence, provided preferably that the encoded polypeptide has the specified characteristics. The addition, insertion, deletion and/or substitution of one or more nucleotides may or may not be reflected in an alteration in the encoded amino acid sequence, depending on the genetic code.

Preferably, the nucleic acid molecule is a "mini-gene", i.e. the polypeptide encoded does not correspond to full-length utrophin but is rather shorter, a truncated version. For instance, part or all of the rod domain may be missing, such that the polypeptide comprises an actin-binding domain and a DPC-binding domain but is shorter than naturally occurring utrophin. In a full-length utrophin gene, the actin-binding domain is encoded by nucleotides 1–739, while the DPC-binding domain (CRCT) is encoded by nucleotides 8499–10301 (where 1 represents the start of translation; FIG. 2A). The respective domains in the polypeptide encoded by a mini-gene according to the invention may comprise amino acids corresponding to those encoded by these nucleotides in the full-length coding sequence.

Dystrophin mini-genes have been shown to be active in animal models (as discussed). Advantages of a mini-gene over a sequence encoding a full-length utrophin molecule or derivative thereof include easier manipulation and inclusion in vectors, such as adenoviral and retroviral vectors for delivery and expression.

A further preferred non-naturally occurring molecule encoding a polypeptide with the specified characteristics is a chimaeric construct wherein the encoding sequence comprises a sequence obtainable from one mammal, preferably human ("a human sequence"), and a sequence obtainable from another mammal, preferably mouse ("a mouse sequence"). Such a chimaeric construct may of course comprise the addition, insertion, substitution and/or deletion of one or more nucleotides with respect to the parent mammalian sequences from which it is derived. Preferably, the part of the coding sequence which encodes the actin-binding domain comprises a sequence of nucleotides obtainable from the mouse, or other non-human mammal, or a sequence of nucleotides derived from a sequence obtainable from the mouse, or other non-human mammal.

In a preferred embodiment, the sequence of nucleotides encoding the polypeptide comprises sequence GAGGCAC at residues 332–338 and/or the sequence GATTGTGGAT-GAAAACAGTGGG at residues 1452–1476 (using the conventional numbering from the initiation codon ATG), and a sequence obtainable from a human.

The nucleic acid molecule may comprise a nucleotide sequence encoding a sequence of amino acids shown in FIG. 1. As discussed, the encoding sequence may be chimaeric, i.e. comprise sequences of nucleotides from different species, e.g. a sequence from or derivable from a human and a sequence from or derivable from a mouse or other non-human mammal.

A chimaeric mini-gene encoding sequence according to the present invention is shown in FIG. 3. Preferred embodiments of the present invention include a nucleic acid molecule comprising a sequence of nucleotides encoding a polypeptide which has an actin-binding domain and a DPC-binding domain and which polypeptide comprises an amino acid sequence encoded by a sequence of nucleotides shown in FIG. 3, a nucleic acid molecule comprising a sequence of nucleotides encoding a variant, allele. or derivative of such a polypeptide by way of addition, substitution, insertion and/or deletion of one or more amino acids, and a nucleic acid molecule comprising a sequence of nucleotides which is a variant, allele or derivative of the sequence shown in FIG. 3, by way of addition, substitution, insertion and/or deletion of one or more nucleotides, with or without a change in the encoded amino acid sequence with respect to the amino acid sequence encoded by a sequence of nucleotides shown in FIG. 3. The proviso is that the encoded polypeptide is "utrophin-like" rather than "dystrophin-like", e.g. as determined immunologically as discussed.

One particular variant or derivative of the sequence of FIG. 3 has a sequence as shown in FIG. 9, which is a "full-length" utrophin construct, including rod domain sequences not included in the mini-gene of FIG. 3.

The sequences of FIG. 3 and FIG. 9 include some positions at which the precise residue is left open (marked by "N" in the nucleotide sequence and "X" in the amino acid sequence). Comparison of the human, mouse and rat utrophin sequences in this region (FIG. 10) shows that the human and rat amino acid sequences are absolutely conserved here. Accordingly, the twelve "X's" in FIGS. 3 and 9 may represent the amino acid sequence DKKSIIMYLTSL (SEQ ID NO:15). Instead, in accordance with the discussion of variants and derivatives herein, a polypeptide according to the invention (as encoded by nucleic acid according to the invention) may include a variant or derivative sequence, by way of one or more of insertion, addition, substitution or deletion of one or more amino acids of the sequence DKKSIIMYLTSL (SEQ ID NO:15), in the position marked by the X's in FIGS. 3 and 9.

Nucleic acid according to the present invention is obtainable by hybridising nucleic acid of target cells (e.g. human, mouse, rat) with one or more oligo- or poly-nucleotides with sequences designed based on the sequence information presented in FIG. 1, FIG. 3 or FIG. 9. Thus, the full mouse sequence, or the sequence in the region marked by the X's in FIGS. 3 and 9, may be obtained by probing or PCR using sequence information provided herein (e.g. FIG. 1).

Nucleic acid according to the present invention is obtainable using one or more oligonucleotide probes or primers designed to hybridise with one or more fragments of a nucleic acid sequence shown in FIG. 1, FIG. 3 or FIG. 9, particularly fragments of relatively rare sequence, based on codon usage or statistical analysis. The amino acid sequence information provided may be used in design of degenerate probes/primers or "long" probes. A primer designed to hybridise with a fragment of the nucleic acid sequence shown may be used in conjunction with one or more oligonucleotides designed to hybridise to a sequence in a cloning vector within which target nucleic acid has been cloned, or in so-called "RACE" (rapid amplification of cDNA ends) in which cDNA's in a library are ligated to an oligonucleotide linker and PCR is performed using a primer which hybridises with the sequence shown in the figure and a primer which hybridises to the oligonucleotide linker.

Nucleic acid isolated and/or purified from one or more cells (e.g. human, mouse) or a nucleic acid library derived from nucleic acid isolated and/or purified from cells (e.g. a cDNA library derived from mRNA isolated from the cells), may be probed under conditions for selective hybridisation and/or subjected to a specific nucleic acid amplification reaction such as the polymerase chain reaction (PCR).

A method may include hybridisation of one or more (e.g. two) probes or primers to target nucleic acid. Where the nucleic acid is double-stranded DNA, hybridisation will generally be preceded by denaturation to produce single-stranded DNA. The hybridisation may be as part of a PCR procedure, or as part of a probing procedure not involving PCR. An example procedure would be a combination of PCR and low stringency hybridisation. A screening procedure, chosen from the many available to those skilled in the art, is used to identify successful hybridisation events and isolated hybridised nucleic acid.

Probing may employ the standard Southern blotting technique. For instance DNA may be extracted from cells and digested with different restriction enzymes. Restriction fragments may then be separated by electrophoresis on an agarose gel, before denaturation and transfer to a nitrocellulose filter. Labelled probe may be hybridised to the DNA fragments on the filter and binding determined. DNA for probing may be prepared from RNA preparations from cells.

Preliminary experiments may be performed by hybridising under low stringency conditions various probes to Southern blots of DNA digested with restriction enzymes.

Suitable conditions would be achieved when a large number of hybridising fragments were obtained while the background hybridisation was low. Using these conditions nucleic acid libraries, e.g. cDNA libraries representative of expressed sequences, may be searched.

It may be necessary for one or more gene fragments to be ligated to generate a full-length coding sequence. Also, where a full-length encoding nucleic acid molecule has not been obtained, a smaller molecule representing part of the full molecule, may be used to obtain full-length clones. Inserts may be prepared from partial cDNA clones and used to screen cDNA libraries.

Those skilled in the art are well able to employ suitable conditions of the desired stringency for selective hybridisation, taking into account factors such as oligonucleotide length and base composition, temperature and so on.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary cells, HeLa cells, baby hamster kidney cells and many others. A common, preferred bacterial host is *E. coli*.

Nucleic acid according to the present invention may form part of a cloning vector and/or a vector from which the encoded polypeptide may be expressed. Suitable vectors can be chosen or constructed, containing appropriate and appropriately positioned regulatory sequences, including promoter sequences, terminator fragments, polyadenylation sequences, enhancer sequences, marker genes and other sequences as appropriate. Vectors may be plasmids, viral e.g. phage, or phagemid, as appropriate. For further details see, for example, *Molecular Cloning: a Laboratory Manual*: 2 nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in *Short Protocols in Molecular Biology*, Second Edition, Ausubel et al. eds., John Wiley & Sons, 1992. The disclosures of Sambrook et al. and Ausubel et al. are incorporated herein by reference.

Thus, a further aspect of the present invention provides a host cell containing nucleic acid as disclosed herein. A still further aspect provides a method comprising introducing such nucleic acid into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage.

The introduction may be followed by causing or allowing expression from the nucleic acid, e.g. by culturing host cells under conditions for expression of the gene.

In one embodiment, the nucleic acid of the invention is integrated into the genome (e.g. chromosome) of the host cell. Integration may be promoted by inclusion of sequences which promote recombination with the genome, in accordance with standard techniques.

The invention also provides a mammal, such as a human, primate or rodent, preferably rat or mouse, comprising a host cell as provided, and methods of production and use of such a mammal. The mammal may be non-human. Transgenic animals, particularly mice, can be generated using any available technique. Particularly suitable for purposes of study are mdx mice or others with a dystrophic phenotype.

The polypeptide encoded by the nucleic acid may be expressed from the nucleic acid in vitro, e.g. in a cell-free system or in cultured cells, or in vivo. In vitro expression may be useful in determining ability of the polypeptide to bind to actin and/or DPC. This may be useful in testing or screening for substances able to modulate one or both of these binding activities. In particular, substances able to increase actin and/or DPC binding of the polypeptide will add to the repertoire of molecules available for potential pharmaceutical/therapeutic exploitation. Such substances, identified as modulators of one or both of the binding activities of the polypeptide, following expression of the polypeptide from encoding nucleic acid therefor, may be investigated further and may be manufactured and/or used in preparation of a medicament, pharmaceutical composition or drug which may subsequently be administered to an individual. In vivo expression is discussed further below.

According to a further aspect of the present invention there is provided a polypeptide with utrophin function (other than utrophin itself). Such a polypeptide comprises an actin-binding domain and a DPC-binding domain and is immunologically recognisable as utrophin-like rather than dystrophin-like, as discussed, not-being a naturally occurring polypeptide. The polypeptide may be any of those discussed above as being encoded by nucleic acid according to the present invention. In particular, the polypeptide may be shorter than naturally occurring full-length utrophin, for example by virtue of lacking all or part of the rod domain. The actin-binding and DPC-binding domains may correspond to those of human, mouse or other non-human utrophin or may be derived therefrom by way of addition, substitution, insertion and/or deletion of one or more amino acids. The polypeptide may be chimaeric, comprising sequences of amino acids from or derived from different species, e.g. human and mouse, as discussed.

A convenient way of producing a polypeptide according to the present invention is to express nucleic acid encoding it. Accordingly, methods of making such polypeptides by expression from encoding nucleic acid therefor are provided by the present invention, in vitro, e.g. in cell-free systems or by culturing host cells under appropriate conditions for expression, or in vivo.

Polypeptides and nucleic acid according to the invention may be used in the manufacture of medicaments, compositions, including pharmaceutical formulations, and drugs for delivery to an-individual, e.g. a human with muscular dystrophy or a non-human mammal, such as a mouse, as a model for study of the polypeptides, muscular dystrophy and therapy thereof.

For example, a method of treatment practised on the human or animal body in accordance with the present invention may comprise administration to an individual of nucleic acid encoding a polypeptide as disclosed herein. The nucleic acid may form part of a construct enabling expression within cells of the individual. Nucleic acid may be introduced into cells using a retroviral vector, preferably one which will not transform cells, or using liposome technology.

Administration is preferably in a "therapeutically effective amount", this being sufficient to show benefit to a patient. Such benefit may be at least amelioration of at least one symptom. The actual amount administered, and rate and time-course of administration, will depend on the nature and severity of what is being treated. Prescription of treatment, eg decisions on dosage etc, is within the responsibility of general practitioners and other medical doctors.

A composition may be administered alone or in combination with other treatments, either simultaneously or sequentially dependent upon the condition to be treated.

Pharmaceutical compositions according to the present invention, and for use in accordance with the present invention, may comprise, in addition to active ingredient, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous or intravenous.

Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such has water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient may be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Injection may be used to deliver nucleic acid to disease sites. Internally, suitable imaging devices may be employed to guide an injecting needle to the desired site.

It may be desirable to remove cells from the body, treat them then return them to the body, or to administer cells derived from cells removed from an individual. This might be appropriate, for example, if muscle stem cells can be isolated. Muscle precursor cells ("mpc") have been used in cell therapy in mdx mice, where implantation of normal mpc gave rise to substantial amounts of dystrophin [25,26,27]. Immunosuppression increases success of cell implantation procedures [13]. Myoblasts may be used to introduce genes into muscle fibres during growth or repair, as has been demonstrated using a replication-defective retroviral vector to introduce a mini-dystrophin construct into proliferating myogenic cells in tissue culture [28].

Thus, cells in culture may have nucleic acid according to the present invention introduced into them before the cells are grafted into muscles in a patient. Grafting the cells back into the donor has the advantages of a genetically corrected autologous transplant. Nucleic acid may be introduced locally into cells using transfection, electroporation, microinjection, liposomes, lipofecting or as naked DNA or RNA, or using any other suitable technique.

Retroviral vectors have also been used to introduce the dystrophin mini-gene into the myoblasts of spontaneously regenerating muscle of the mdx mouse to produce dystrophin-positive fibres [8]. Recombinant replication defective adenoviruses appear particularly effective as an efficient means of introducing constructs into skeletal muscle fibres for persistent expression [29]. See reference 11 for a review of myoblast-based gene therapies.

Adenoviral, retroviral or other viral vectors may be used advantageously for the introduction of a utrophin sequence according to the present invention into muscle cells. Even though in vivo transduction may be restricted to growing or regenerating muscle fibres, retrovirally introduced constructs have the advantage of becoming integrated into the genome of the host cell, potentially conferring lifelong expression.

Liposomes may be used as vehicles for delivery of nucleic acid constructs to skeletal muscle. Intravenous injection of constructs in cationic liposomes has resulted in widespread transfection of most tissues, including skeletal muscle [30]. Lack of immunogenicity allows for repeated administration and lack of tissue specificity may be accommodated by choosing a muscle-specific promoter to drive expression.

For use in distinguishing polypeptide with utrophin function from dystrophin and related polypeptides, antibodies may be obtained using techniques which are standard in the art. Methods of producing antibodies include immunising a mammal (eg mouse, rat, rabbit, horse, goat, sheep or monkey) with the protein or a fragment thereof, or a cell or virus which expresses the protein or fragment. Immunisation with DNA encoding a target polypeptide is also possible (see for example Wolff, et al. *Science* 247: 1465–1468 (1990); Tang, et al. *Nature* 356: 152–154 (1992); Ulmer J B, et al. *Science* 259: 1745–1749 (1993)). Antibodies may be obtained from immunised animals using any of a variety of techniques known in the art, and screened, preferably using binding of antibody to antigen of interest. For instance, Western blotting techniques or immunoprecipitation may be used (Armitage et al, 1992, Nature 357: 80–82).

The production of monoclonal antibodies is well established in the art. Monoclonal antibodies can be subjected to the techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EP184187A, GB 2188638A or EP-A-0239400. A hybridoma producing a monoclonal antibody may be subject to genetic mutation or other changes, which may or may not alter the binding specificity of antibodies produced.

As an alternative or supplement to immunising a mammal with a peptide, an antibody specific for a protein may be obtained from a recombinantly produced library of expressed immunoglobulin variable domains, eg using lambda bacteriophage or filamentous bacteriophage which display functional immunoglobulin binding domains on their surfaces;. for instance see WO92/01047. The library may be naive, that is constructed from sequences obtained from an organism which has not been immunised with the target, or may be one constructed using sequences obtained from an organism which has been exposed to the antigen of interest (or a fragment thereof).

Antibodies may be modified in a number of ways. Indeed the term "antibody" should be construed as covering any specific binding substance having an binding domain with the required specificity. Thus this covers antibody fragments, derivatives, functional equivalents and homologues of antibodies, including any polypeptide comprising an immunoglobulin binding domain, whether natural or synthetic. Chimaeric molecules comprising an immunoglobulin binding domain, or equivalent, fused to another polypeptide are therefore included. Cloning and expression of chimaeric antibodies are described in EP-A-0120694 and EP-A-0125023.

It has been shown that the function of binding antigens can be performed by fragments of a whole antibody. Example binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward, E. S. et al., Nature 341, 544–546 (1989)) which consists of a VH domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al, *Science*, 242, 423–426, 1988; Huston et al, *PNAS USA*, 85, 5879–5883, 1988); (viii) bispecific single chain Fv dimers (PCT/US92/09965) and (ix) "diabodies", multivalent or multispecific fragments constructed by gene fusion (WO94/13804; P. Holliger et al Proc. Natl. Acad. Sci. USA 90 6444–6448, 1993).

Further aspects and embodiments of the present invention, and modifications to aspects and embodiments disclosed herein, will be apparent to those skilled in the art.

The following figures are attached hereto:

FIGS. 1a and 1b: FIG 1a shows the corresponding parts of nucleotide sequences of the mouse (Moutro) (SEQ ID NO:1), rat (ratutro) (SEQ ID NO:2) and human (humutro) (SEQ ID NO:3) starting from the first amino acid and encompassing the actin binding domain and start of the rod domain. The heavyline represents the unclonable region in rat and human. FIG. 1b shows the sequence of the second unclonable region (SEQ ID NO:4, SEQ ID NO:5 and SEQ ID NO:6).

FIGS. 2a–2c are a schematic of the cloning process of PCR6.0. FIG. 2a: The bold numbers represent the utrophin transcript in kb and the numbers below the line represent the nucleotide positions of the regions in question where 1 is the start of translation; FIG. 2b represents the cDNAs used as template for the PCR; FIG. 2c represents the two PCR fragments generated to form PCR6.0.

FIGS. 3a–3e show the nucleotide sequence (both strands) (SEQ ID NO:7 and SEQ ID NO:8) of a "utrophin minigene" according to the present invention and whose construction is described herein.

FIGS. 5a–5c: Utrophin transgene construction and expression. FIG. 5a, Scale representation of dystrophin, utrophin and the two truncated transgenes. The repeated spectrin-like repeats (R) and the potential hinge sites (H) are marked. FIG. 5b, Utrophin transgene vector. The N- and C-terminal portions of utrophin were cloned as PCR products using overlapping cDNAs as template. The regions used are indicated by the dotted lines. The PCR product was cloned into a vector containing the 2.2 kb human skeletal α-actin (HSA) promoter and regulatory regions [20,21] and SV40 large T poly A site. The cloning sites were such that the transgene was located near the beginning of the second HSA untranslated exon and the Asp718/NotI sites were used to liberate the complete fragment. FIG. 5c, Immunoblot of muscle from the utrophin transgenic line F-3 and a non-transgenic C57BL/10 littermate. M, skeletal muscle; H, heart; D, diaphragm.

Figures 6A, 6B:
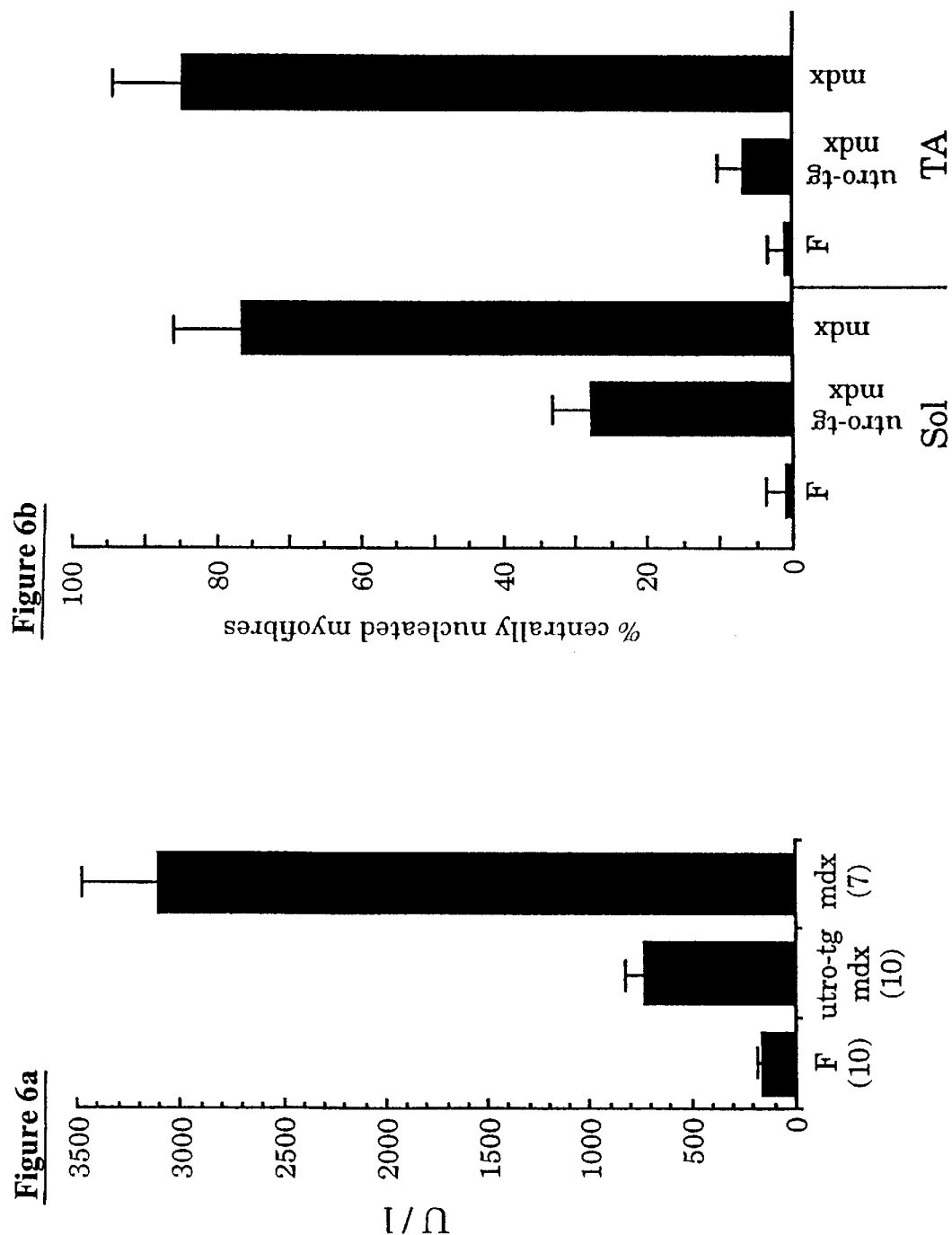

FIGS. 6a and 6b: Decrease in serum CK levels and centralised myofibres in transgenic mdx mice. FIG. 6a, Serum creatine kinase levels in male mdx mice expressing the utrophin transgene. Serum creatine kinase levels from 5 week old mice generated from 4 $F_3$ litters resultant from a male transgenic mouse crossed with female mdx. Offspring consisted of male hemizygous mdx (M mdx), male utrophin transgenic mdx (M Tg mdx) and heterozygous females (F mdx). Female heterozygotes are not significantly different from wild type so can be used as normal controls. The number of mice (n) in each group is shown in parentheses and the mean SE shown by T-bars. FIG. 6b, Proportion of myofibres containing centralised nuclei. The mean SE is shown by T-bars.

Figure 7A:
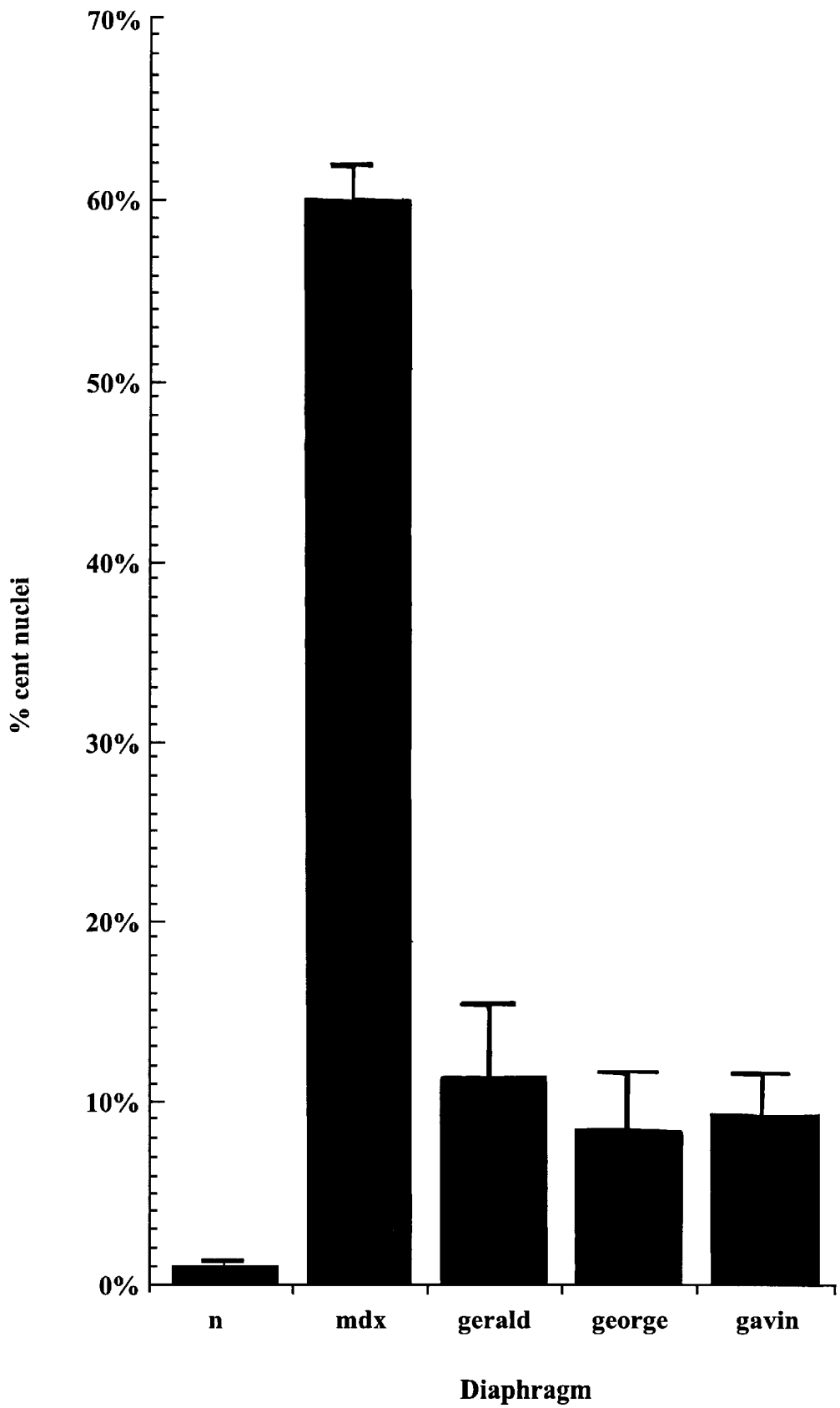
Figure 7B:
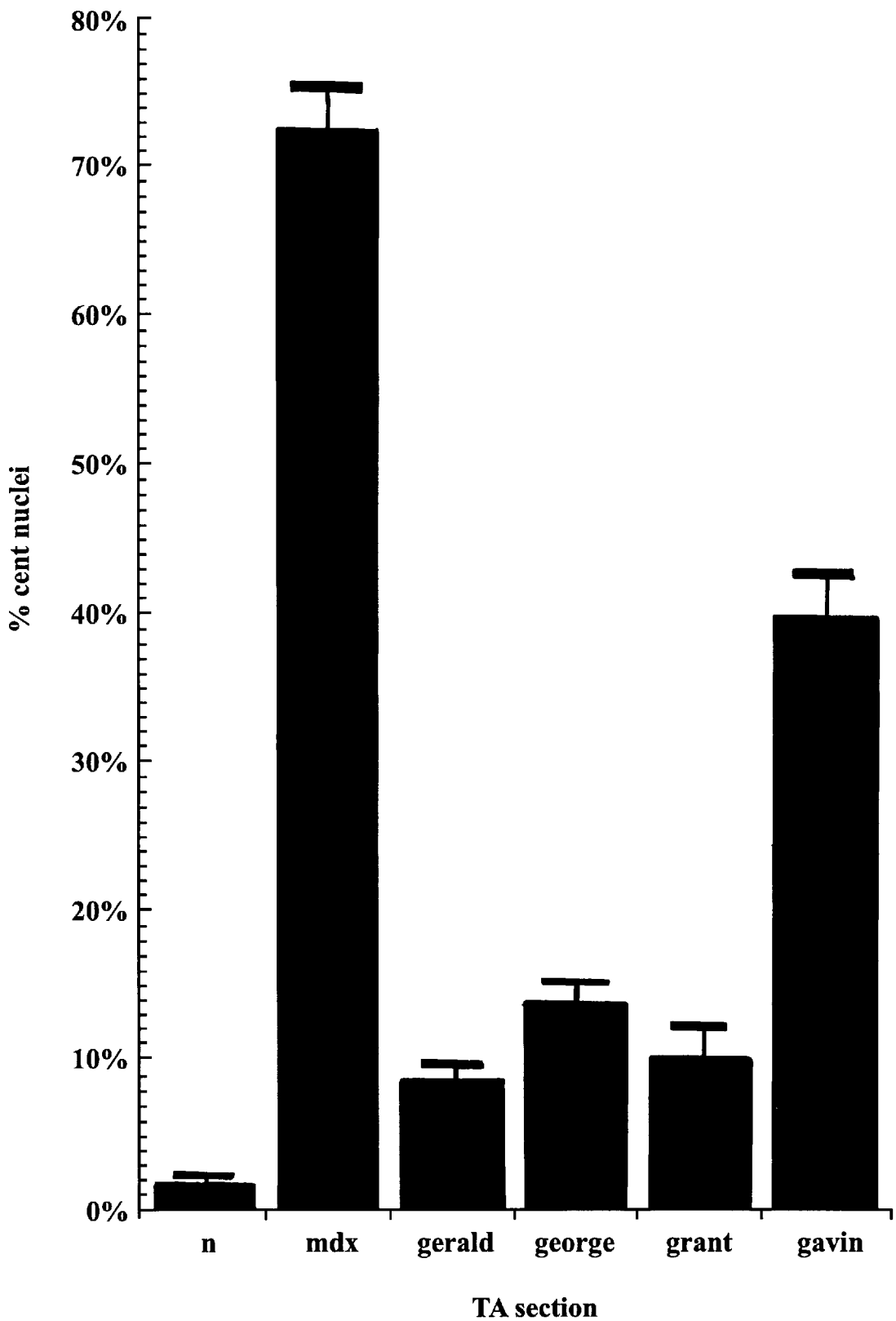

FIGS. 7a and 7b: Decrease in centralised nuclei in Diaphragm and TA muscle from other truncated utrophin transgenic mdx lines (Gerald, George, Grant, Gavin), normal (n) and mdx (mdx). The mean SE is shown by T-bars.

Figure 8:
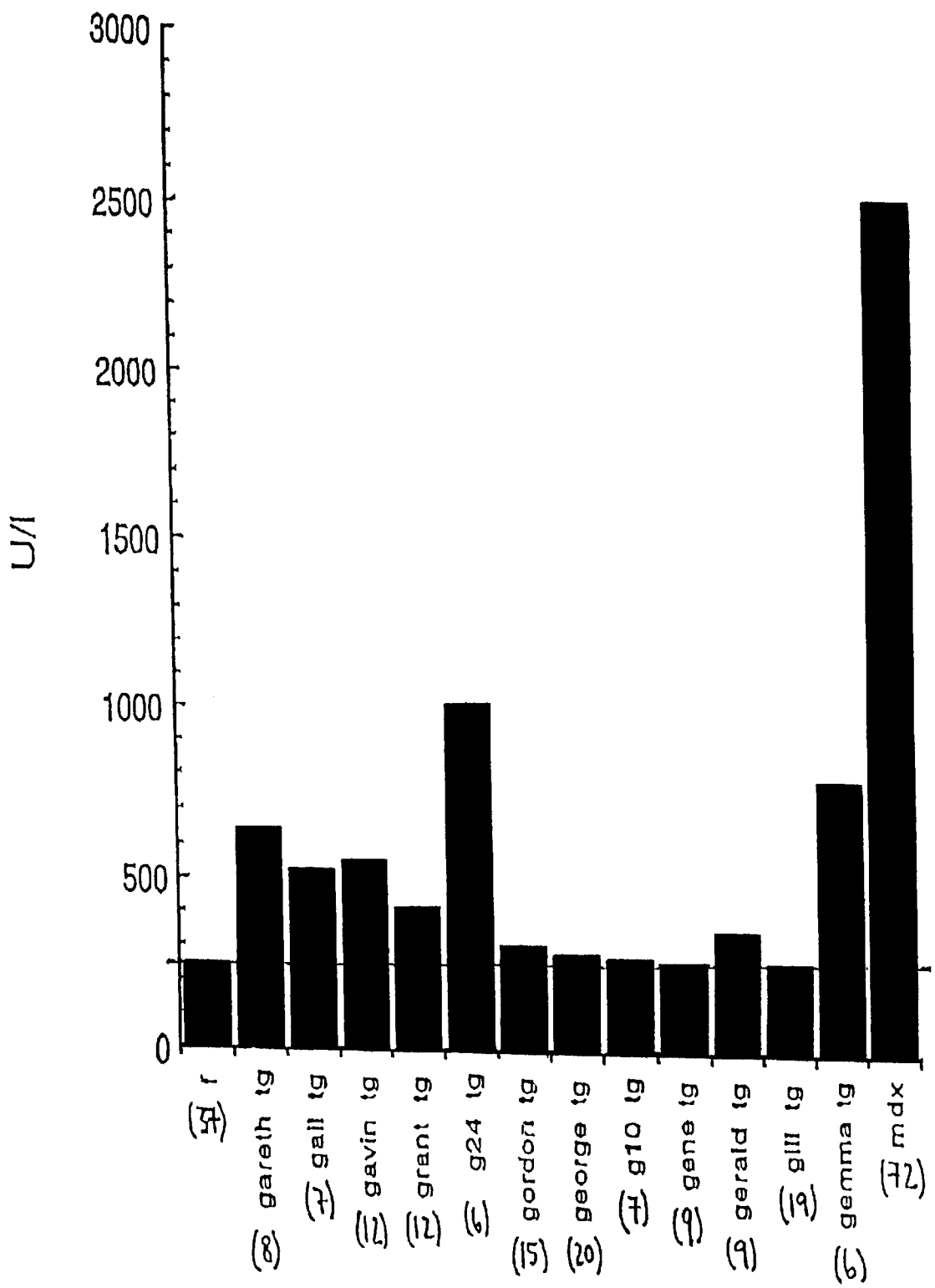

FIG. 8: Decrease in serum creatine kinase from other utrophin transgenic lines, normal (n) and mdx (mdx). The number of mice in each group is shown in parenthesis.

FIGS. 9a–9i: Full length utrophin coding sequence (SEQ ID NO:9) and encoded amino acid sequence (SEQ ID NO:10).

FIG. 10: Alignment of amino acid sequences for the N-terminal regions of human (SEQ ID NO:11), mouse (SEQ ID NO:12) and rat (SEQ ID NO:13) utrophin.

All documents cited are incorporated herein by reference.

EXAMPLE 1

Cloning of Utrophin Minigenes

Figures 2A, 2B, 2C:
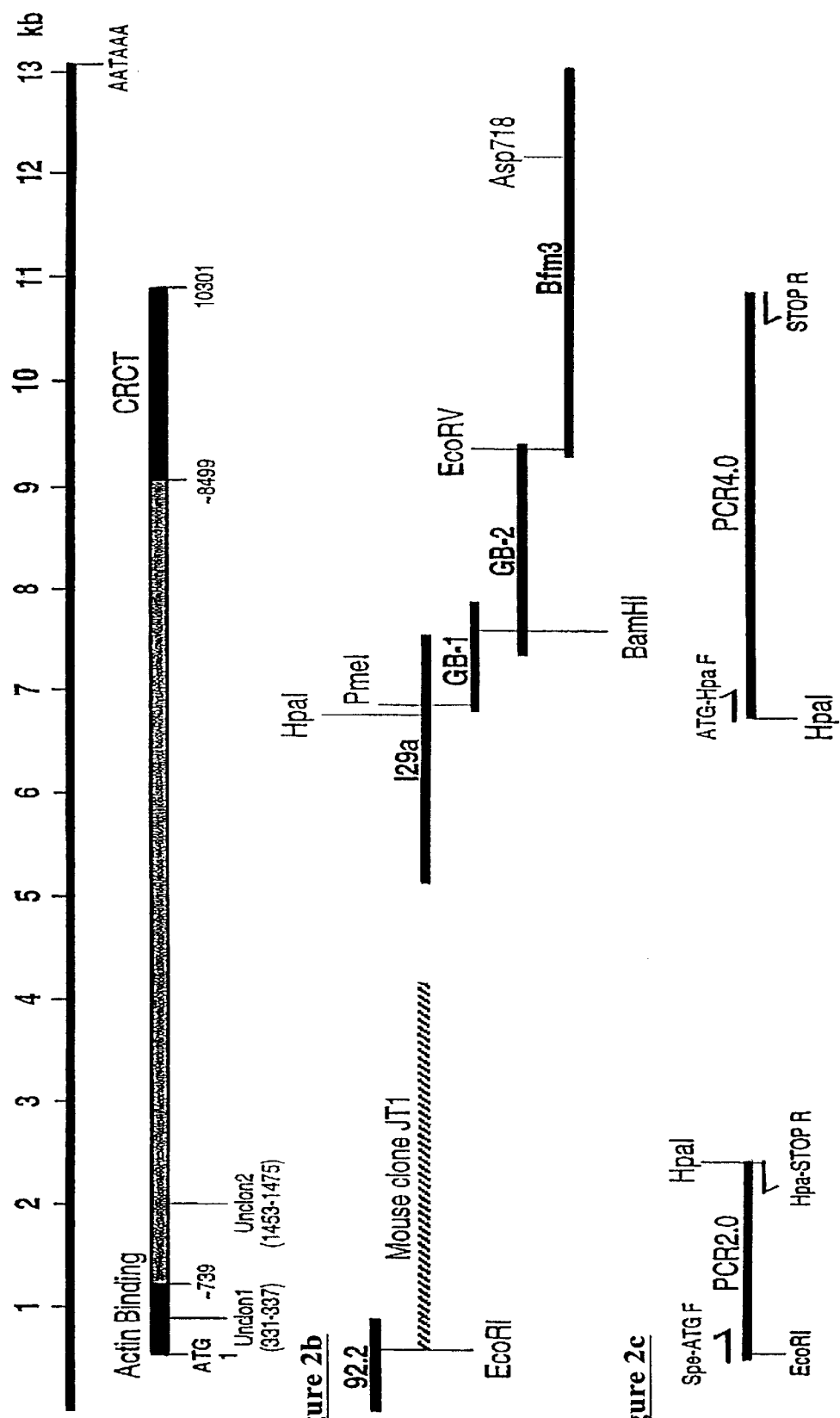

The four cDNAs covering the latter half of the human utrophin transcript were ligated together using overlapping restriction endonuclease sites. The amino-terminal region was reconstructed using the human 92.2 cDNA joined by the common EcoRI restriction site to the stable mouse cDNA clone, JT1. These two constructs were then used as templates for PCR amplification (FIG. 2B). Primers were designed to generate two fragments, PCR2.0 and PCR 4.0, containing no untranslated regions which could be ligated in frame to generate a utrophin minigene containing approximately the first 2 kb and last 4 kb of the utrophin coding sequence (FIG. 2C).

The two PCR fragments were ligated together using the HpaI site. The complete DNA sequence of the 6.0 kb minigene is shown in FIG. 3. The complete 6 kb minigene was excised from the vector and ligated into the eukaryotic expression vectors. SV40-pA consists of the SV40 early promoter linked to exon 1 and part of exon 2 (including the intron) of rabbit β globin to facilitate splicing of any cloned insert. This is of particular importance if the construct is to be used to generate transgenic lines. After a single unique blunt restriction site for cloning inserts into, there is the SV40 small T poly A signal sequence. The SV40 promoter will express the minigene in all tissues. The HSA-pA construct is similar except for the use of the human skeletal α actin promoter and tissue specific regulatory sequences which will direct expression of the minigene product only in skeletal muscle.

Once cloned into the expression vectors the unique HpaI site was used to clone in a PCR generated fragment containing the remainder of the utrophin rod domain. We now have expression vectors containing a truncated and full length utrophin coding sequence.

The unique HpaI restriction site has also been used to clone in a synthetic oligonucleotide coding for the amino acid sequence which is recognised by a specific antibody to the myc protein. This will enable minigene constructs to be localised by virtue of their expression of the myc tag and recognition by the antibody. For utrophin this is a problem as the endogenous gene is expressed in all cell types. The use of the tag will demonstrate the presence of the minigene when delivered in a gene therapy protocol. There are available a number of other tags including the Flag epitope (IBI) and Green Fluorescent Protein (Clontech) which could be used in a similar fashion.

Figure 4:
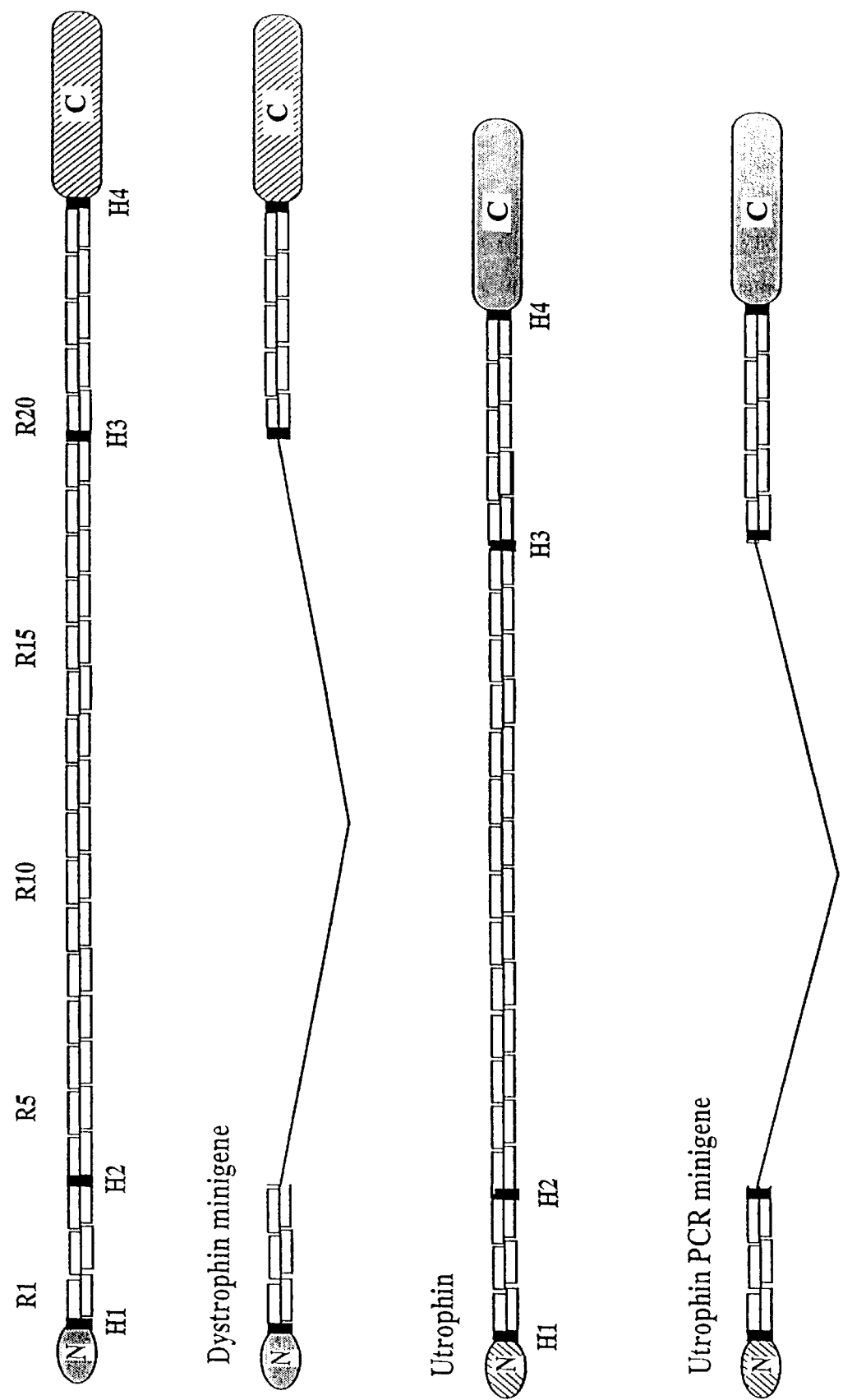
FIG. 4 shows a representation of the dystrophin and utrophin polypeptides, showing the various domains, and "mini-genes" comprising only parts of the full-length molecules.

The utrophin minigene generated consists of the same domains and repeats as the dystrophin minigene (FIG. 4). The dystrophin minigene was originally copied in vitro from a naturally occurring dystrophin mutation which gave rise to a mild Becker muscular dystrophy phenotype. It has been used successfully in a number of viral vectors being designed for potential gene therapy routes and in transgenic lines which ameliorate the abnormal muscle phenotype in mdx mice. Thus the utrophin minigene will be suitable for cloning into viral vectors designed for specific tissue expression in potential gene therapy procedures.

Verification of the Integrity of Minigenes

It was important to screen for the maintenance of an open reading frame in the PCR generated clones given the propensity for Taq thermostable polymerase to introduce mutations. The PCR products were cloned into a vector which had RNA polymerase binding sites allowing the cloned insert to be transcribed and translated generating a radiolabelled protein. If expressed proteins were observed of the correct molecular weight it was inferred that the PCR product had no stop mutations. These products were then western blotted to see if they were recognised by utrophin antibodies. A positive result demonstrated that the expressed protein was in the correct frame to generate the epitopes recognised by the antibodies. Ten different clones both for the PCR2.0 and PCR4.0 were screened in this manner. In all cases full length expression was observed. All PCR2.0 and PCR4.0 clones were detected by MANNUT1 [31] (which recognises the actin binding domain) and MANCHO7 [18] (which recognises the latter half of the carboxy-terminal) respectively.

Two minigenes were constructed from two different PCR2.0 and 4.0 clones which met the criteria above and cloned into the expression vectors. To check the integrity of the completed minigene, COS cells were transiently transfected with both SV40-PCR6.0 minigenes (A4 and B1) and harvested after time points. Expression of the PCR6.0 minigene protein was identified by western blotting using MANNUT1 [31] and MANCH07 [18].

Similar transfections were done using these constructs then the cells fixed and immunostained using MANCH07 [18]. Staining of the minigene appeared to be membrane bound suggesting that the actin binding domain or the CRCT or both are functional in order to explain the staining pattern seen.

The myc tag epitope has also been cloned in frame into the unique HpaI site within the minigene. This construct, SV40-PCR6.0-myc, was also transfected into COS cells and immunolocalised using-the myc tag mouse monoclonal antibody, 9 E10. Again membrane localisation was observed showing that introduction of the 10 amino acids which constitutes the myc tag epitope does not appear to effect the properties of the minigene.

EXAMPLE 2

In Vivo Compensation for Dystrophic Deficiency by Utrophin Expression

We have tested expressing a utrophin transgene in the dystrophin deficient mdx mouse. Our results indicate that high expression of the utrophin transgene in skeletal muscle can reverse the dystrophic pathology. These data suggest that systemic up-regulation of utrophin in DMD patients is a very promising avenue for the development of an effective treatment for this devastating disorder.

A truncated utrophin transgene was modeled on the Becker dystrophin transgene which has been shown to correct the dystrophic phenotype of mdx mice [5,6] (FIG. 5A). In order to generate high levels of muscle expression the utrophin transgene was driven by the human skeletal alpha actin (HSA) promoter (FIG. 5B). A number of transgenic lines expressing the utrophin transgene were generated with differing levels of transgenic expression. Immunoblot analysis of muscle samples from transgenic lines demonstrating high level expression are shown in FIG. 5C. The multiple fainter bands are probably due to the proteolytic breakdown of the highly expressed transgene product [24]. Line 347 also shows weak expression of the transgene in the heart. Analysis of the F-3 line shows no evidence of transgene expression in heart, brain, kidney, lung, liver, intestine, skin or pancreas was observed. To demonstrate that the utrophin transgene localised to the sarcolemma, immunofluorescence of skeletal muscle sections was performed using utrophin and dystrophin specific antibodies. Examination of the sarcolemmal localisation pattern of dystrophin and the utrophin transgene in consecutive muscle sections demonstrated that they are able to co-localise in vivo. The normal localisation of utrophin in adult skeletal muscle is exclusively at the neuromuscular and myotendenous junctions and in the capillaries and nerves [3,31]. Immunostaining of unfixed 8 $\mu$m TA muscle cryosections was done with 1/25 dilution of G3 (anti-utrophin) or 1/400 dilution of P6 (anti-dystrophin [33]) Initially the sections were blocked in 10% heat inactivated foetal calf serum in 50 mM Tris, 150 mM NaCl pH7.5 (TBS), then the primary antibody diluted in TBS added and incubated for 1 h at room temperature. The slides were washed 4× in TBS for 5 min each then incubated for a further hour at room temperature with 1/1000 dilution FITC conjugated sheep anti-rabbit IgG (Sigma) diluted in TBS. Finally the slides were washed as before, mounted with VectaShield (Vector Labs) and photographed using a Leica DMRBE microscope and photomicrograph system.

Although the dystrophin deficient mdx mouse is only mildly affected, histological and physiological analysis reveals a number of muscle defects in common with DMD patients including muscle fibre degeneration giving rise to a dramatic elevation of serum creatine kinase (CK) and evidence of massive myofibre regeneration with most fibres having centrally located nuclei [34]. Thus changes in the levels of serum CK and numbers of centralised nuclei have been used to monitor the pathology of the muscle in a number of transgenic lines expressing dystrophin transgenes in mdx mice [5,6,7,24]. Male transgenic F-3 mice carrying the utrophin transgene were crossed with dystrophin deficient female mdx mice and the resultant offspring analysed (FIG. 2A). The CK levels of 5 week old male transgenic mdx mice had fallen to approximately a quarter of the non transgenic mdx male littermates. Females whether transgenic or not have essentially normal levels of serum CK. The reduction in the serum levels of CK in the transgenic male mdx littermates signifies a change in the muscle pathology of these mice and implies that a significant decrease in muscle degeneration has occurred. FIG. 2B shows the contrast in numbers of centralised nuclei in frozen sections from the soleus and tibialis anteria (TA) muscle of transgenic and non-transgenic male mdx mice. The numbers of centrally nucleated myofibres is markedly reduced in the two muscle types examined showing that the amount of fibre regeneration is decreased. The difference in numbers of central nuclei between the transgenic mdx TA (~10%) and soleus (~30%) is probably explained by the fact that the HSA promoter is expressed at lower levels in the slow twitch fibres which essentially populate the soleus muscle compared to the fast twitch fibres of the TA. This is an important observation as it implies that the levels of utrophin transgene are important for amelioration of the muscle phenotype.

Dystrophin is normally associated with a large oligomeric protein complex (dystrophin protein complex; DPC) embedded in the sarcolemma [3,35]. Loss of dystrophin in DMD patients and mdx mice also results in a dramatic loss of sarcolemmal DPC [36]. In transgenic mdx mice expressing the full length and truncated dystrophin transgenes, re-establishment of components of the DPC at the sarcolemma is an important marker for the restoration of muscle strength by dystrophin transgenes [5,6,7,24]. We looked at the results of immunostaining for components of the DPC in TA muscle from male mdx or mdx expressing the utrophin transgene. This was as described above. The primary antibodies were goat polyclonal sera to α/β-dystroglycan [37] (FP-B, 1/10), rabbit polyclonal sera to α-sarcoglycan [38] (1/5) and sheep polyclonal sera to γ-sarcoglycan [39] (1/10). FITC conjugated secondary antibodies to goat, rabbit and sheep were diluted 1/50, 1/200 and 1/50 respectively. Sarcolemmal staining of all myofibres by utrophin specific antibody was seen in transgenic muscle. However in the non-transgenic mice there is virtually no sarcolemmal staining apart from neuromuscular junctions and regions likely to contain regenerating fibres. In all cases using polyclonal antibodies specific to α-sarcoglycan, γ-sarcoglycan, and α/β-dystroglycan there was a notable increase in the staining at the sarcolemma of transgenic TA muscle indicating an elevation in correctly localised, sarcolemmal bound DPCs. The increase in sarcolemmal staining of these components in the soleus muscle is greater than the non-transgenic mdx males but not as elevated as in the TA. This result suggests that increased utrophin transgene expression correlates with an increase in sarcolemmal bound DPC.

Analysis of the mdx diaphragm has shown that this muscle exhibits a continued pattern of degeneration, fibrosis and functional deficit throughout the life span of the mdx mouse which is comparable to DMD skeletal muscle [40]. Thus for utrophin to be capable of replacing dystrophin, over-expression of utrophin in this muscle has to alter the pathology in a similar way as demonstrated for the dystrophin transgenic mdx mice [5,6,7,24]. Immunostaining of diaphragm sections using a utrophin antibody demonstrates the sarcolemmal localisation of the utrophin transgene expressed in the transgenic mdx mouse (utro-tg mdx) compared to the normal and mdx seen is the re-establishment of α-sarcoglycan at the sarcolemma of the transgenic mdx diaphragm at levels similar to the normal diaphragm. Sarcolemmal staining of the transgenic mdx diaphragm similar to normal is also seen using antibodies specific to α/β-dystroglycan and γ-sarcoglycan (data not shown). Thus, as in skeletal muscle, expression of the utrophin transgene in diaphragm relocalises the DPC to the sarcolemma. Histological analysis of haematoxylin and eosin stained sections of mdx diaphragm shows extensive regions of fibrosis, cellular infiltration and variable myofibre size containing centralised nuclei. However the utrophin transgenic diaphragm looks essentially the same as normal, with no necrosis, regular myofibre size and virtually no centralised nuclei. In the mdx diaphragm, even in regions which have no necrosis so appear more histologically normal, on higher magnification the myofibres are still of variable size often containing centralised nuclei which is indicative of continual regeneration. In the utrophin transgenic diaphragm even at higher magnification, the whole muscle appears normal. A return to normal histology and establishment of the DPC are two important observations, as seen with the dystrophin transgenic mice [5,6,7,24], which predicts a major recovery of the utrophin transgenic diaphragm from a dystrophic phenotype.

We have demonstrated a significant decrease in the dystrophic muscle phenotype of mdx mice by expressing a utrophin transgene at high levels in the skeletal muscle and the diaphragm. These results, for the first time, strongly suggest that utrophin can replace dystrophin in vivo This implies that use of small molecules which increase the normal utrophin muscle expression to compensate and therefore alleviate the consequences of a lack of dystrophin is a promising avenue for DMD therapy. This approach would potentially target all muscles and thus prolong life by conserving the respiratory and cardiac muscles. Utrophin is expressed in many tissues so a generalised upregulation may not have detrimental side effects. In our experimental animal model, the normal mice expressing the utrophin transgene at high levels appear to suffer no deleterious side effects in their skeletal and diaphragm muscles. A precedent for such a gene therapy approach using butyrate to upregulate fetal haemoglobin is having success in clinical trials of sickle cell disease [41,42]. Only 20–30% of the wild type levels of dystrophin are required to significantly reduce the dystrophic phenotype in mdx mice [9,10]. It will be interesting to determine whether similar levels of utrophin will be adequate to compensate for dystrophin loss. In addition, since utrophin is normally expressed in all tissues, including muscle, the use of this utrophin transgene rather than a dystrophin transgene in conventional gene therapy approaches e.g. using viruses or liposomes may avert any potential immunological responses against the transgene.

Muscle from transgenic mdx and mdx mice were stressed in vitro. Essentially the test monitors the high mechanical stress produced by force lengthening during active contraction and measures the decrease in force. The method is essentially described in detail by Deconinck et al [46]. The measure of deterioration is a decrease in the force a muscle can apply. This force drop is irreversible and correlates with the number of damaged muscle fibres. Mdx muscle is particularly sensitive to this test and deteriorates greatly [46].

Our data demonstrate that the force drop in mdx mice is –55%. However, in the utrophin transgenic littermates the force drop was only –20%. Normal mouse muscle usually has a force drop of –15%. Thus the expression of the utrophin transgene in mdx mice considerably decreases the damage caused by large mechanical stress.

Methods

Transgene Construction and Microinjection

The amino- and carboxy-terminal portions of utrophin were cloned as PCR products using overlapping cDNAs as template then ligated together in-frame to produce the truncated utrophin cDNA. The PCR product was then cloned into a vector containing the 2.2 kb human skeletal α-actin (HSA) promoter and regulatory regions [43,44] and SV40 large T poly A site. The cloning sites were such that the transgene was located near the beginning of the second HSA untranslated exon and the Asp718/NotI sites were used to liberate the complete fragment. Transgenic mice were generated by microinjection of the purified HSA transgene insert into the pronucleus of $F_2$ hybrid oocytes from C57BL/

6xCBA/CA parents [45]. Positive transgenic mice were identified by southern blotting using a probe to the central part of the utrophin transgene. A number of founder $F_0$ males were bred to generate more offspring for analysis and breeding.

Protein Analysis

Total muscle extracts were prepared by homogenisation in 1 ml extraction buffer (75 mM Tris pH6.8, 3.8% SDS, 4M Urea, 20% Glycerol, 5% β-mercaptoethanol) then heated 95° C. for 5 min. Usually 50 μg of total protein (quantitated using Biorad DC protein assay kit) was loaded onto 6. polyacrylamide gels and transferred to nitrocellulose. Utrophin transgene expression was detected using a 1/200 dilution of mouse anti-utrophin monoclonal antibody (MANCHO7 [18]) and visualised using anti-mouse IgG-POD and chemiluminescence (Boehringer). For sectioning, skeletal muscle samples were removed and immersed in OCT compound (BDH) and frozen in liquid nitrogen cooled isopentane. Diaphragm was removed, cut in half then rolled longitudinally and sandwiched between Ox liver to facilitate orientation and easier sectioning. The sandwich was then frozen. Immunostaining of unfixed 8 μm cryosections was performed by blocking the sections in 10% heat inactivated foetal calf serum in 50 mM Tris, 150 mM NaCl pH7.5 (TBS), then the primary antibody diluted in TBS added and incubated for 1 h at room temperature. The slides were washed 4× in TBS for 5 min each then incubated for a further hour at room temperature with conjugated second antibody diluted in TBS. Finally the slides were washed as before, mounted with VectaShield (Vector Labs) and photographed using a Leica DMRBE microscope and photomicrograph system.

Antibodies used for Immunofluorescence

Antibodies were used at the following dilutions. Polyclonal rabbit against utrophin (G3, 1/25), dystrophin (P6 [33], 1/400), β1-syntrophin (syn35, 1/50) α-sarcoglycan [38] (1/5). Goat polyclonal against α/β-dystroglycan (FP-B [37], 1/10). FITC conjugated secondary antibody to goat (Sigma) and Cy3 conjugated secondary antibody to rabbit (Jackson Laboratories) were diluted 1/50 and 1/200 respectively.

Creatine Kinase Assay

Serum CK levels from 4–5 week old mice generated from 4 $F_3$ litters resultant from a male transgenic mouse crossed with female mdx were assayed. The tail tips were cut off and DNA prepared for Southern blotting to establish the transgenic status of each mouse. Blood was collected simultaneously, allowed to clot and serum removed. Serum creatine kinase levels were measured using the Boehringer NAC-CK kit and 5 μl of serum. The rate per minute was averaged over 4 min and calculated as U/l.

EXAMPLE 3

To see if expression of utrophin is beneficial to muscle in the process of regenerating, the myc tagged truncated utrophin minigene under the control of the HSA promoter (HSA-PCR6.0-myc) was directly injected into mdx muscle.

Our data demonstrate the sarcolemmal localisation of the utrophin minigene in a proportion of fibres close to the injection site. The utrophin minigene was detected using the antibody 9E10 which is specific to the myc tag epitope. Importantly where 9E10 was localised there was a significant staining of α- and γ-sarcoglycan. The α-sarcoglycan staining was essentially negative in other fibres.

Re-establishment of the dystrophin protein complex has been shown to be an important marker for muscle recovery [5,6,7,24]. This result suggests that even when the disease process has manifested itself, namely the degeneration and regeneration seen in mdx muscle, expression of utrophin is beneficial. This is important when considering that in DMD one third of effected boys are new mutations. Thus only when the first symptoms of DMD manifest themselves after a couple of years after birth can diagnosis be attained.

EXAMPLE 4

Utilising a PCR strategy to generate fragments from human 1 st strand DNA, the remainder of the human utrophin sequences missing from PCR6.0 were cloned. The fragment utilised primers which allowed the rod domain to be cloned into the unique HpaI restriction site (see FIG. 2c) to produce a clone which contained all of the amino acid coding sequence to produce the complete utrophin protein. FIG. 9 shows the DNA sequence of the full length utrophin construct with the amino acid sequence shown above using the standard single letter code.

The utrophin full length construct has been cloned into the human skeletal alpha actin promoter (HSA) expression construct in a similar manner to that shown in FIG. 5b. This full length utrophin expression construct has been used to generate transgenic mice capable of expressing the full length utrophin protein in mouse muscle. Similar experiments may be performed as described in Example 2 to identify any differences in the effectiveness of the full length utrophin protein compared with the truncated utrophin protein in alleviating the muscle pathology in mdx mice.

In order to assess whether high levels of utrophin expression in all tissues is detrimental, to assist in planning therapeutic protocols and in particular choosing between tissue-specific expression or non-specific expression, a mouse model is being developed using the full length utrophin construct. Transgenic mice will be created expressing the full length utrophin protein under the regulation of a promoter which is expressed in all tissues. The promoter chosen for the first experiments is the human Ubiquitin-C promoter which has been shown to express in all tissues. Once these mice are shown to be expressing the full length utrophin transgene they will be monitored to identify any potential side effects caused by abnormally high levels of utrophin.

References

1. Winder et al. (1995) *FEBS Letts* 369: 27–33.
2. Blake et al. (1994) *Trend In Cell Biol* 4: 19–23.
3. Tinsley et al. (1994) *Proc Natl Acad Sci, USA* 91: 8307–8313.
4. England et al. (1990) *Nature* 11: 180–182.
5. Phelps et al. (1995) *Hum Mol Genet* 4: 1251–1258.
6. Wells et al. (1995) *Hum Mol Genet* 4: 1245–1250.
7. Rafael et al. (1994) *Hum Mol Genet* 3: 1725–1733.
8. Dunckley et al. (1993) *Hum Mol Genet* 2: 717–723.
9. Alameddine et al. (1994) *Neuromusc Dis* 4: 193–203.
10. Vincent et al. (1993) *Nat Genet* 5: 130–134.
11. Partridge T A and Davies K E. (1995) *Brit Med Bull* 51: 123–137.
12. Guerette et al. (1995) *Muscle Nerve* 18: 39–51.
13. Huard et al. (1994) *Muscle Nerve* 17: 224–234.
14. Tinsley et al. (1992) *Nature* 360: 591–593.
15. Khurana et al. (1991) *Neuromusc Disord* 1: 185–194.
16. Takemitsu et al. (1991) *Biochem Biophys Res Com* 180: 1179–1186.
17. Clerk et al. (1993) *Histochem* 25: 554–561.
18. Nguyen et al. (1991) *J Cell Biol* 115: 1695–1700.
19. Tanaka et al. (1991) *Histochem* 96: 1–5.
20. Karpati et al. (1993) *J Neuropath Exp Neurology* 52: 119–128.

21. Mizuno et al. (1993) *J Neurol Sci* 1993.
22. Helliwell et al. (1992) *Neuromusc Dis* 3: 177–184.
23. Matsumura et al. (1992) *Nature* 360: 588–591.
24. Cox et al. (1993) *Nature* 364: 725–729.
25. Patridge et al. (1989) *Nature* 337: 176–179.
26. Karpati et al. (1989) *In Cellular and Molecular Biology of Muscle Development* (Alan R. Liss, New York) pp 973–985).
27. Morgan et al. (1990) *J Cell Biol* 111: 2437–2449.
28. Dunckley et al. (1992) *FEBS Letts* 296: 128–134.
29. Stratford-Perricaudet et al. (1992) *J Clin Invest* 90: 626–630.
30. Thierry et al. (1995) *Proc Nat Acad Sci USA* 92: 9742–9746.
31. Ngygen et al. (1995) *FEBS Letts* 358: 262–266.
32. Blake, et al. *Brain Pathology* 6, 37–47 (1996).
33. Sherratt, et al. *Biochem J* 287, 755–759 (1992).
34. Sicinski, et al. *Science* 244, 1578–80 (1989).
35. Matsumara, K. & Campbell, K. P. *Muscle Nerve* 17, 2–15 (1994).
36. Campbell, K. P. *Cell* 80, 675–9 (1995)
37. Ibraghimov-Beskrovnaya, et al. *Nature* 355, 696–702 (1992).
38. Roberds, et al. *Biol. Chem.* 268, 23739–23742 (1993).
39. Jung, et al, *FEBS Letts*. 381, 15–20 (1996).
40. Stedman, et al. *Nature*. 352, 536–539 (1991).
41. Collins, et al. *Blood* 85, 43–9 (1995).
42. Dover, et al. *Blood* 84, 339–43 (1994).
43. Brennan, K. J. & Hardeman, E. C. *J. Biol. Chem.* 268, 719–725 (1993).
44. Muscat, G. O. & Kedes, L. Mol. *Cell Biol*. 7, 4089–4099 (1987).
45. Hogan, et al. *Manipulating the mouse embryo: A laboratory manual* (Cold Spring Harbour Laboratory Press, New York, 1986).
46. Deconinck, et al. *Proc. Natl. Acad. Sci. USA* 93, 3570–3574 (1996).

What is claimed is:

1. An isolated nucleic acid encoding the polypeptide with the amino acid sequence of FIG. 3 (SEQ ID NO:8) and which on expression in a host cell produces the polypeptide.

2. The isolated nucleic acid according to claim 1 wherein the nucleotide sequence of the nucleic acid encoding the polypeptide with the amino acid sequence of FIG. 3 (SEQ ID NO:8) is the coding nucleotide sequence shown in FIG. 3 (SEQ ID NO:7).

3. The isolated nucleic acid according to claim 1 wherein the nucleotide sequence of the nucleic acid encoding the polypeptide with the amino acid sequence of FIG. 3 (SEQ ID NO:8) differs from the coding nucleotide sequence shown in FIG. 3 (SEQ ID NO:7).

4. A vector comprising the nucleic acid according to claim 1.

5. The vector according to claim 4 wherein said vector is an expression vector.

6. A composition including the nucleic acid according to claim 1 and a pharmaceutically acceptable excipient.

7. A cell containing the nucleic acid according to claim 1, which nucleic acid is heterologous to the cell.

8. A cell according to claim 7 which is a muscle cell.

9. A cell according to claim 7 wherein said polypeptide is expressed.

10. A method comprising introducing the nucleic acid according to claim 1 into a cell.

11. A method according to claim 10 wherein said cell is a muscle cell.

12. A method according to claim 10 comprising introducing said nucleic acid into said cell in vitro.

13. A method which comprises expressing the coding nucleotide sequence of the nucleic acid according to claim 1 in a cell, which nucleic acid is heterologous to the cell.

14. The method according to claim 13 wherein said polypeptide is produced, and is then purified or isolated.

15. The method according to claim 14 wherein the polypeptide is formulated into a composition which comprises a pharmaceutically acceptable excipient, following purification or isolation of the polypeptide.

16. A method for treating muscular dystrophy in a mammal, the method comprising providing cells of the mammal with a polypeptide encoded by the nucleic acid according to claim 1 under conditions such that said treatment is effected.

17. A method according to claim 16 wherein the polypeptide is provided to the cells by expression from encoding nucleic acid administered to the mammal.

18. An isolated nucleic acid encoding a polypeptide different from the polypeptide of which the amino acid sequence is shown in FIG. 3 (SEQ ID NO:8), wherein the polypeptide:

has an actin-binding-domain which has at least 90% amino acid sequence identity with the actin-binding domain of the polypeptide of which the amino acid sequence is shown in FIG. 3 (SEQ ID NO:8), and has a dystrophin-protein-complex-binding-domain which has at least 90% amino acid sequence identity with the dystrophin-protein-complex-binding domain of the polypeptide of which the amino acid sequence is shown in FIG. 3 (SEQ ID NO:8), wherein the nucleotide sequence of the nucleic acid encoding the polypeptide comprises nucleotides 342 to 348 and 1462 to 1486 of FIG. 3 (SEQ ID NO:7), and on expression in a host cell prodces the polypeptide.

19. The isolated nucleic acid according to claim 18 wherein the amino acid sequence of the polypeptide is that shown in FIG. 9 (SEQ ID NO:10).

20. The isolated nucleic acid according to claim 19 wherein the nucleotide sequence of the nucleic acid encoding the polypeptide is the coding nucleotide sequence of FIG. 9 (SEQ ID NO:9).

21. The isolated nucleic acid according to claim 19 wherein the nucleotide sequence of the nucleic acid encoding the polypeptide differs from the coding nucleotide sequence shown in FIG. 9 (SEQ ID NO:9).

22. A vector comprising the nucleic acid according to claim 1.

23. The vector according to claim 22 wherein said vector is an expression vector.

24. A composition comprising the nucleic acid according to claim 18 and a pharmaceutically acceptable excipient.

25. A cell containing the nucleic acid according to claim 18, which nucleic acid is heterologous to the cell.

26. A cell according to claim 25 which is a muscle cell.

27. A cell according to claim 25 wherein said polypeptide is expressed.

28. A method comprising introducing the nucleic acid according to claim 18 into a cell.

29. A method according to claim 28 wherein said cell is a muscle cell.

30. A method according to claim 28 comprising introducing said nucleic acid into said cell in vitro.

31. A method which includes expressing the coding nucleotide sequence of the nucleic acid according to claim 18 in a cell, which nucleic acid is heterologous to the cell.

32. The method according to claim 31 wherein said polypeptide is produced, and is then purified or isolated.

33. The method according to claim 32 wherein the polypeptide is formulated into a composition which comprising a pharmaceutically acceptable excipient, following purification or isolation of the polypeptide.

34. A method for treating muscular dystrophy in a mammal, the method comprising providing cells of the mammal with a polypeptide encoded by the nucleic acid according to claim 18 under conditions such that said treatment is effected.

35. A method for treating muscular dystrophy in a mammal, the method comprising providing cells of the mammal with a polypeptide according to claim 19 under conditions such that said treatment is effected.

* * * * *

SEQUENCE LISTING

<160> NUMBER OF SEQ ID NOS: 15

<210> SEQ ID NO 1
<211> LENGTH: 710
<212> TYPE: DNA
<213> ORGANISM: Mus sp.

<400> SEQUENCE: 1

```
atggccaagt atggggacct tgaagcctgg cctgatgggc agatcgaatt cagtgacatc       60
attgagtcca gatctgatga acacaatgat gtacagaaga aaacctttac caaatggata      120
aacgctcgat tttccaagag tgggaaacca cccatcagtg atatgttctc agacctcaaa      180
gatgggagaa agctcttgga tcttctcgaa ggcctcacag gaacatcatt gccaaaggaa      240
cgtggttcca caagggtgca tgccttaaac aatgtcaacc gagtgctaca ggttttacat      300
cagaacaatg tggacttggt gaatattgga ggcacggaca ttgtggatgg aaatcccaag      360
ctgactttag ggttactctg gagcatcatt ctgcactggc aggtgaagga tgtcatgaaa      420
gatatcatgt cagacctgca gcagacaaac agcgagaaga tcctgctgag ctgggtgcgg      480
cagaccacca ggccctacag tcaagtcaac gtcctcaact tcaccaccag ctggaccgat      540
ggactcgcgt tcaacgccgt gctccaccgg cacaaaccag atctcttcag ctgggacaga      600
gtggtcaaaa tgtccccaat tgagagactt gaacatgctt ttagcaaggc ccacacttat      660
ttgggaattg aaaagcttct agatcctgaa gatgttgctg tgcatctccc                710
```

<210> SEQ ID NO 2
<211> LENGTH: 713
<212> TYPE: DNA
<213> ORGANISM: Rattus sp.

<400> SEQUENCE: 2

```
atggccaagt acgggcacct tgaagccagc cctgatgatg ggcagaatca gttcagtgat       60
atcattaagt ccagatctga tgaacacaac gatgtacaga agaaaacctt taccaaatgg      120
ataaacgctc gattttcaaa gagtgggaaa ccacccatca atgatatgtt ctcagacctc      180
aaagatggga gaaagctctt ggatcttcta gaaggcctca caggaacatc attgccaaag      240
gaacgtggtt ccacaagggt gcatgcctta aataatgtca accgggtgct gcaggtttta      300
catcagaaca atgtggagct ggtgaatatc ggaggcactg acattgtgga tggaaatccc      360
```

```
aagctgacgc tgggtttgct gtggagtatt attctgcact ggcaggtgaa ggatgtcatg      420
aaagatatca tgtcagacct gcagcagacg aacagcgaga agatcctgct gagctgggta      480
cggcagacca ccaggcccta cagccaagtc aacgtcctca acttcaccac cagctggaca      540
gatggactcg cattcaacgc cgtgctccac cggcacaaac cagatctctt cagctgggac      600
agagtggtca aaatgtcccc aactgagaga cttgaacatg cttttagcaa ggcccatact      660
tatttgggga ttgaaaaact tctggatcct gaagatgttg ccgtgcagct ccc            713
```

```
<210> SEQ ID NO 3
<211> LENGTH: 713
<212> TYPE: DNA
<213> ORGANISM: Homo sapiens

<400> SEQUENCE: 3
atggccaagt atgagaaca tgaagccagt cctgacaatg gcagaacga attcagtgat       60 atcattaagt ccagatctga tgaacacaat gacgtacaga agaaaaacctt taccaaatgg   120 ataaatgctc gattttcaaa gagtgggaaa ccacccatca atgatatgtt cacagacctc    180
aaagatggaa ggaagctatt ggatcttcta gaaggcctca caggaacatc actgccaaag    240
gaacgtggtt ccacaagggt acatgcctta ataacgtca acagagtgct gcaggtttta    300
catcagaaca atgtggaatt agtgaatata ggggaactg acattgtgga tggaaatcac    360
aaactgactt ggggttact ttggagcatc attttgcact ggcaggtgaa agatgtcatg     420
aaggatgtca tgtcggacct gcagcagacg aacagtgaga agatcctgct cagctgggtg   480
cgtcagacca ccaggcccta cagccaagtc aacgtcctca acttcaccac cagctggaca   540
gatggactcg cctttaatgc tgtcctccac cgacataaac ctgatctctt cagctgggat   600
aaagttgtca aaatgtcacc aattgagaga cttgaacatg ccttcagcaa ggctcaaact   660
tatttgggaa ttgaaaagct gttagatcct gaagatgttg ccgttcggct tcc           713
```

```
<210> SEQ ID NO 4
<211> LENGTH: 200
<212> TYPE: DNA
<213> ORGANISM: Mus sp.

<400> SEQUENCE: 4
tgatgacctg ccctccctgc agaagctgct tcaagaacat aaaagtttgc aaaatgacct     60
tgaagctgaa caggtgaagg taaattcctt aactcacatg gtggtgattg tggatgaaaa   120
cagtggggag agtgccacag ctcttctgga agatcagtta cagaaactgg gtgagcgctg   180
gacagctgta tgccgctgga                                                200
```

```
<210> SEQ ID NO 5
<211> LENGTH: 200
<212> TYPE: DNA
<213> ORGANISM: Rattus sp.

<400> SEQUENCE: 5
tgacgaccta ccctccctgc aaaacctgct tgaagaacat aaaagtttgc aaagtgacct     60
cgaagctgag caggtgaagg tgaattcctt aactcatatg gtggtgattg tggatgaaaa   120
cagtggggag agcgccacag ctgttttgga agatcagtta cagaaactgg gtgagcgctg   180
gacagctgta tgccgctgga                                                200
```

```
<210> SEQ ID NO 6
```

-continued

```
<211> LENGTH: 200
<212> TYPE: DNA
<213> ORGANISM: Homo sapiens

<400> SEQUENCE: 6
tgatgatgtg aaatctctac aaaagctgct agaagaacat aaaagtttgc aaagtgatct        60
tgaggctgaa caggtgaaag taaattcact aactcacatg gtggtcattg ttgatgaaaa       120
cagtggtgag agcgctacag ctatcctaga agaccagtta cagaaacttg gtgagcgctg       180
gacagcagta tgccgttgga                                                   200

<210> SEQ ID NO 7
<211> LENGTH: 6045
<212> TYPE: DNA
<213> ORGANISM: Artificial Sequence
<220> FEATURE:
<221> NAME/KEY: CDS
<222> LOCATION: (11)..(6037)
<220> FEATURE:
<223> OTHER INFORMATION: Description of Artificial Sequence: Chimeric
<220> FEATURE:
<221> NAME/KEY: misc_feature
<222> LOCATION: (724)..(758)
<223> OTHER INFORMATION: Precise residue is left open

<400> SEQUENCE: 7
actagtcaag atg gcc aag tat gga gaa cat gaa gcc agt cct gac aat         49
            Met Ala Lys Tyr Gly Glu His Glu Ala Ser Pro Asp Asn
              1               5                  10 ggg cag aac gaa ttc agt gac atc att gag tcc aga tct gat gaa cac        97
Gly Gln Asn Glu Phe Ser Asp Ile Ile Glu Ser Arg Ser Asp Glu His
 15                  20                  25 aat gat gta cag aag aaa acc ttt acc aaa tgg ata aac gct cga ttt       145
Asn Asp Val Gln Lys Lys Thr Phe Thr Lys Trp Ile Asn Ala Arg Phe
 30                  35                  40                  45 tcc aag agt ggg aaa cca ccc atc agt gat atg ttc tca gac ctc aaa       193
Ser Lys Ser Gly Lys Pro Pro Ile Ser Asp Met Phe Ser Asp Leu Lys
                 50                  55                  60 gat ggg aga aag ctc ttg gat ctt ctc gaa ggc ctc aca gga aca tca       241
Asp Gly Arg Lys Leu Leu Asp Leu Leu Glu Gly Leu Thr Gly Thr Ser
             65                  70                  75 ttg cca aag gaa cgt ggt tcc aca agg gtg cat gcc tta aac aat gtc       289
Leu Pro Lys Glu Arg Gly Ser Thr Arg Val His Ala Leu Asn Asn Val
         80                  85                  90 aac cga gtg cta cag gtt tta cat cag aac aat gtg gac ttg gtg aat       337
Asn Arg Val Leu Gln Val Leu His Gln Asn Asn Val Asp Leu Val Asn
     95                 100                 105 att gga ggc acg gac att gtg gat gga aat ccc aag ctg act tta ggg       385
Ile Gly Gly Thr Asp Ile Val Asp Gly Asn Pro Lys Leu Thr Leu Gly
110                 115                 120                 125 tta ctc tgg agc atc att ctg cac tgg cag gtg aag gat gtc atg aaa       433
Leu Leu Trp Ser Ile Ile Leu His Trp Gln Val Lys Asp Val Met Lys
                130                 135                 140 gat atc atg tca gac ctg cag cag aca aac agc gag aag atc ctg ctg       481
Asp Ile Met Ser Asp Leu Gln Gln Thr Asn Ser Glu Lys Ile Leu Leu
            145                 150                 155 agc tgg gtg cgg cag acc acc agg ccc tac agt caa gtc aac gtc ctc       529
Ser Trp Val Arg Gln Thr Thr Arg Pro Tyr Ser Gln Val Asn Val Leu
        160                 165                 170 aac ttc acc acc agc tgg acc gat gga ctc gcg ttc aac gcc gtg ctc       577
Asn Phe Thr Thr Ser Trp Thr Asp Gly Leu Ala Phe Asn Ala Val Leu
    175                 180                 185
```

| | | |
|---|---|---|
| cac cgg cac aaa cca gat ctc ttc agc tgg gac aga gtg gtc aaa atg<br>His Arg His Lys Pro Asp Leu Phe Ser Trp Asp Arg Val Val Lys Met<br>190                             195                       200                      205 | 625 |
| tcc cca att gag aga ctt gaa cat gct ttt agc aag gcc cac act tat<br>Ser Pro Ile Glu Arg Leu Glu His Ala Phe Ser Lys Ala His Thr Tyr<br>                        210                       215                       220 | 673 |
| ttg gga att gaa aag ctt cta gat cct gaa gat gtt gct gtg cat ctc<br>Leu Gly Ile Glu Lys Leu Leu Asp Pro Glu Asp Val Ala Val His Leu<br>               225                       230                       235 | 721 |
| ccn nnn nnn nnn nnn nnn nnn nnn nnn nnn nnn ncc gtt gag gtg<br>Pro Xaa Xaa Xaa Xaa Xaa Xaa Xaa Xaa Xaa Xaa Xaa Val Glu Val<br>         240                       245                       250 | 769 |
| ctt cct cag caa gtc acg ata gat gcc atc cga gag gtg gag act ctc<br>Leu Pro Gln Gln Val Thr Ile Asp Ala Ile Arg Glu Val Glu Thr Leu<br>255                       260                       265 | 817 |
| cca agg aag tat aag aaa gaa tgt gaa gag gaa gaa att cat atc cag<br>Pro Arg Lys Tyr Lys Lys Glu Cys Glu Glu Glu Glu Ile His Ile Gln<br>270                       275                       280                       285 | 865 |
| agt gca gtg ctg gca gag gaa ggc cag agt ccc cga gct gag acc cct<br>Ser Ala Val Leu Ala Glu Glu Gly Gln Ser Pro Arg Ala Glu Thr Pro<br>                        290                       295                       300 | 913 |
| agc acc gtc act gaa gtg gac atg gat ttg gac agc tac cag ata gcg<br>Ser Thr Val Thr Glu Val Asp Met Asp Leu Asp Ser Tyr Gln Ile Ala<br>               305                       310                       315 | 961 |
| cta gag gaa gtg ctg acg tgg ctg ctg tcc gcg gag gac acg ttc cag<br>Leu Glu Glu Val Leu Thr Trp Leu Leu Ser Ala Glu Asp Thr Phe Gln<br>         320                       325                       330 | 1009 |
| gag caa gat gac att tct gat gat gtc gaa gaa gtc aaa gag cag ttt<br>Glu Gln Asp Asp Ile Ser Asp Asp Val Glu Glu Val Lys Glu Gln Phe<br>335                       340                       345 | 1057 |
| gct acc cat gaa act ttt atg atg gag ctg aca gca cac cag agc agc<br>Ala Thr His Glu Thr Phe Met Met Glu Leu Thr Ala His Gln Ser Ser<br>350                       355                       360                       365 | 1105 |
| gtg ggg agc gtc ctg cag gct ggc aac cag ctg atg aca caa ggg act<br>Val Gly Ser Val Leu Gln Ala Gly Asn Gln Leu Met Thr Gln Gly Thr<br>                        370                       375                       380 | 1153 |
| ctg tca gag gag gag gag ttt gag atc cag gaa cag atg acc ttg ctg<br>Leu Ser Glu Glu Glu Glu Phe Glu Ile Gln Glu Gln Met Thr Leu Leu<br>               385                       390                       395 | 1201 |
| aat gca agg tgg gag gcg ctc cgg gtg gag agc atg gag agg cag tcc<br>Asn Ala Arg Trp Glu Ala Leu Arg Val Glu Ser Met Glu Arg Gln Ser<br>         400                       405                       410 | 1249 |
| cgg ctg cac gac gct ctg atg gag ctg cag aag aaa cag ctg cag cag<br>Arg Leu His Asp Ala Leu Met Glu Leu Gln Lys Lys Gln Leu Gln Gln<br>               415                       420                       425 | 1297 |
| ctc tca agc tgg ctg gcc ctc aca gaa gag cgc att cag aag atg gag<br>Leu Ser Ser Trp Leu Ala Leu Thr Glu Glu Arg Ile Gln Lys Met Glu<br>430                       435                       440                       445 | 1345 |
| agc cct ccg ctg ggt gat gac ctg ccc tcc ctg cag aag ctg ctt caa<br>Ser Pro Pro Leu Gly Asp Asp Leu Pro Ser Leu Gln Lys Leu Leu Gln<br>                        450                       455                       460 | 1393 |
| gaa cat aaa agt ttg caa aat gac ctt gaa gct gaa cag gtg aag gta<br>Glu His Lys Ser Leu Gln Asn Asp Leu Glu Ala Glu Gln Val Lys Val<br>               465                       470                       475 | 1441 |
| aat tcc tta act cac atg gtg gtg att gtg gat gaa aac agt ggg gag<br>Asn Ser Leu Thr His Met Val Val Ile Val Asp Glu Asn Ser Gly Glu<br>         480                       485                       490 | 1489 |
| agt gcc aca gct ctt ctg gaa gat cag tta cag aaa ctg ggt gag cgc<br>Ser Ala Thr Ala Leu Leu Glu Asp Gln Leu Gln Lys Leu Gly Glu Arg<br>495                       500                       505 | 1537 |

```
tgg aca gct gta tgc cgc tgg act gaa gaa cgt tgg aac agg ttg caa      1585
Trp Thr Ala Val Cys Arg Trp Thr Glu Glu Arg Trp Asn Arg Leu Gln
510             515                 520                 525 gaa atc agt att ctg tgg cag gaa tta ttg gaa gag cag tgt ctg ttg      1633
Glu Ile Ser Ile Leu Trp Gln Glu Leu Leu Glu Glu Gln Cys Leu Leu
                530                 535                 540 gag gct tgg ctc acc gaa aag gaa gag gct ttg aat aaa gtt caa acc      1681
Glu Ala Trp Leu Thr Glu Lys Glu Glu Ala Leu Asn Lys Val Gln Thr
            545                 550                 555 agc aac ttt aaa gac cag aag gaa cta agt gtc agt gtc cgg cgt ctg      1729
Ser Asn Phe Lys Asp Gln Lys Glu Leu Ser Val Ser Val Arg Arg Leu
        560                 565                 570 gct ata ttg aag gaa gac atg gaa atg aag agg cag act ctg gat caa      1777
Ala Ile Leu Lys Glu Asp Met Glu Met Lys Arg Gln Thr Leu Asp Gln
    575                 580                 585 ctg agt gag att ggc cag gat gtg ggc caa tta ctc agt aat ccc aag      1825
Leu Ser Glu Ile Gly Gln Asp Val Gly Gln Leu Leu Ser Asn Pro Lys
590                 595                 600                 605 gca tct aag aag atg aac agt gac tct gag gag cta aca cag aga tgg      1873
Ala Ser Lys Lys Met Asn Ser Asp Ser Glu Glu Leu Thr Gln Arg Trp
                610                 615                 620 gat tct ctg gtt cag aga ctc gaa gac tct tct aac cag gtg act cag      1921
Asp Ser Leu Val Gln Arg Leu Glu Asp Ser Ser Asn Gln Val Thr Gln
            625                 630                 635 gcg gta gcg aag ctc ggc atg tcc cag att cca cag aag gac cta ttg      1969
Ala Val Ala Lys Leu Gly Met Ser Gln Ile Pro Gln Lys Asp Leu Leu
        640                 645                 650 gag acc gtt cat gtg aga gaa aaa ggg atg gtg aag aag ccc aag cag      2017
Glu Thr Val His Val Arg Glu Lys Gly Met Val Lys Lys Pro Lys Gln
    655                 660                 665 gaa ctg cct cct ccg tta aca aag gct gag cat gct atg caa aag aga      2065
Glu Leu Pro Pro Pro Leu Thr Lys Ala Glu His Ala Met Gln Lys Arg
670                 675                 680                 685 tca acc acc gaa ttg gga gaa aac ctg caa gaa tta aga gac tta act      2113
Ser Thr Thr Glu Leu Gly Glu Asn Leu Gln Glu Leu Arg Asp Leu Thr
                690                 695                 700 caa gaa atg gaa gta cat gct gaa aaa ctc aaa tgg ctg aat aga act      2161
Gln Glu Met Glu Val His Ala Glu Lys Leu Lys Trp Leu Asn Arg Thr
            705                 710                 715 gaa ttg gag atg ctt tca gat aaa agt ctg agt tta cct gaa agg gat      2209
Glu Leu Glu Met Leu Ser Asp Lys Ser Leu Ser Leu Pro Glu Arg Asp
        720                 725                 730 aaa att tca gaa agc tta agg act gta aat atg aca tgg aat aag att      2257
Lys Ile Ser Glu Ser Leu Arg Thr Val Asn Met Thr Trp Asn Lys Ile
    735                 740                 745 tgc aga gag gtg cct acc acc ctg aag gaa tgc atc cag gag ccc agt      2305
Cys Arg Glu Val Pro Thr Thr Leu Lys Glu Cys Ile Gln Glu Pro Ser
750                 755                 760                 765 tct gtt tca cag aca agg att gct gct cat cct aat gtc caa aag gtg      2353
Ser Val Ser Gln Thr Arg Ile Ala Ala His Pro Asn Val Gln Lys Val
                770                 775                 780 gtg cta gta tca tct gcg tca gat att cct gtt cag tct cat cgt act      2401
Val Leu Val Ser Ser Ala Ser Asp Ile Pro Val Gln Ser His Arg Thr
            785                 790                 795 tcg gaa att tca att cct gct gat ctt gat aaa act ata aca gaa cta      2449
Ser Glu Ile Ser Ile Pro Ala Asp Leu Asp Lys Thr Ile Thr Glu Leu
        800                 805                 810 gcc gac tgg ctg gta tta atc gac cag atg ctg aag tcc aac att gtc      2497
Ala Asp Trp Leu Val Leu Ile Asp Gln Met Leu Lys Ser Asn Ile Val
```

```
            815                 820                 825
act gtt ggg gat gta gaa gag atc aat aag acc gtt tcc cga atg aaa    2545
Thr Val Gly Asp Val Glu Glu Ile Asn Lys Thr Val Ser Arg Met Lys
830                 835                 840                 845 att aca aag gct gac tta gaa cag cgc cat cct cag ctg gat tat gtt    2593
Ile Thr Lys Ala Asp Leu Glu Gln Arg His Pro Gln Leu Asp Tyr Val
            850                 855                 860 ttt aca ttg gca cag aat ttg aaa aat aaa gct tcc agt tca gat atg    2641
Phe Thr Leu Ala Gln Asn Leu Lys Asn Lys Ala Ser Ser Ser Asp Met
        865                 870                 875 aga aca gca att aca gaa aaa ttg gaa agg gtc aag aac cag tgg gat    2689
Arg Thr Ala Ile Thr Glu Lys Leu Glu Arg Val Lys Asn Gln Trp Asp
    880                 885                 890 ggc acc cag cat ggc gtt gag cta aga cag cag cag ctt gag gac atg    2737
Gly Thr Gln His Gly Val Glu Leu Arg Gln Gln Gln Leu Glu Asp Met
895                 900                 905 att att gac agt ctt cag tgg gat gac cat agg gag gag act gaa gaa    2785
Ile Ile Asp Ser Leu Gln Trp Asp Asp His Arg Glu Glu Thr Glu Glu
910                 915                 920                 925 ctg atg aga aaa tat gag gct cga ctc tat att ctt cag caa gcc cga    2833
Leu Met Arg Lys Tyr Glu Ala Arg Leu Tyr Ile Leu Gln Gln Ala Arg
            930                 935                 940 cgg gat cca ctc acc aaa caa att tct gat aac caa ata ctg ctt caa    2881
Arg Asp Pro Leu Thr Lys Gln Ile Ser Asp Asn Gln Ile Leu Leu Gln
        945                 950                 955 gaa ctg ggt cct gga gat ggt atc gtc atg gcg ttc gat aac gtc ctg    2929
Glu Leu Gly Pro Gly Asp Gly Ile Val Met Ala Phe Asp Asn Val Leu
    960                 965                 970 cag aaa ctc ctg gag gaa tat ggg agt gat gac aca agg aat gtg aaa    2977
Gln Lys Leu Leu Glu Glu Tyr Gly Ser Asp Asp Thr Arg Asn Val Lys
975                 980                 985 gaa acc aca gag tac tta aaa aca tca tgg atc aat ctc aaa caa agt    3025
Glu Thr Thr Glu Tyr Leu Lys Thr Ser Trp Ile Asn Leu Lys Gln Ser
990                 995                 1000                1005 att gct gac aga cag aac gcc ttg gag gct gag tgg agg acg gtg cag    3073
Ile Ala Asp Arg Gln Asn Ala Leu Glu Ala Glu Trp Arg Thr Val Gln
            1010                1015                1020 gcc tct cgc aga gat ctg gaa aac ttc ctg aag tgg atc caa gaa gca    3121
Ala Ser Arg Arg Asp Leu Glu Asn Phe Leu Lys Trp Ile Gln Glu Ala
        1025                1030                1035 gag acc aca gtg aat gtg ctt gtg gat gcc tct cat cgg gag aat gct    3169
Glu Thr Thr Val Asn Val Leu Val Asp Ala Ser His Arg Glu Asn Ala
    1040                1045                1050 ctt cag gat agt atc ttg gcc agg gaa ctc aaa cag cag atg cag gac    3217
Leu Gln Asp Ser Ile Leu Ala Arg Glu Leu Lys Gln Gln Met Gln Asp
1055                1060                1065 atc cag gca gaa att gat gcc cac aat gac ata ttt aaa agc att gac    3265
Ile Gln Ala Glu Ile Asp Ala His Asn Asp Ile Phe Lys Ser Ile Asp
1070                1075                1080                1085 gga aac agg cag aag atg gta aaa gct ttg gga aat tct gaa gag gct    3313
Gly Asn Arg Gln Lys Met Val Lys Ala Leu Gly Asn Ser Glu Glu Ala
            1090                1095                1100 act atg ctt caa cat cga ctg gat gat atg aac caa aga tgg aat gac    3361
Thr Met Leu Gln His Arg Leu Asp Asp Met Asn Gln Arg Trp Asn Asp
        1105                1110                1115 tta aaa gca aaa tct gct agc atc agg gcc cat ttg gag gcc agc gct    3409
Leu Lys Ala Lys Ser Ala Ser Ile Arg Ala His Leu Glu Ala Ser Ala
    1120                1125                1130 gag aag tgg aac agg ttg ctg atg tcc tta gaa gaa ctg atc aaa tgg    3457
```

```
                                                            -continued

Glu Lys Trp Asn Arg Leu Leu Met Ser Leu Glu Glu Leu Ile Lys Trp
    1135                1140                1145 ctg aat atg aaa gat gaa gag ctt aag aaa caa atg cct att gga gga              3505
Leu Asn Met Lys Asp Glu Glu Leu Lys Lys Gln Met Pro Ile Gly Gly
1150                1155                1160                1165 gat gtt cca gcc tta cag ctc cag tat gac cat tgt aag gcc ctg aga              3553
Asp Val Pro Ala Leu Gln Leu Gln Tyr Asp His Cys Lys Ala Leu Arg
            1170                1175                1180 cgg gag tta aag gag aaa gaa tat tct gtc ctg aat gct gtc gac cag              3601
Arg Glu Leu Lys Glu Lys Glu Tyr Ser Val Leu Asn Ala Val Asp Gln
        1185                1190                1195 gcc cga gtt ttc ttg gct gat cag cca att gag gcc cct gaa gag cca              3649
Ala Arg Val Phe Leu Ala Asp Gln Pro Ile Glu Ala Pro Glu Glu Pro
    1200                1205                1210 aga aga aac cta caa tca aaa aca gaa tta act cct gag gag aga gcc              3697
Arg Arg Asn Leu Gln Ser Lys Thr Glu Leu Thr Pro Glu Glu Arg Ala
1215                1220                1225 caa aag att gcc aaa gcc atg cgc aaa cag tct tct gaa gtc aaa gaa              3745
Gln Lys Ile Ala Lys Ala Met Arg Lys Gln Ser Ser Glu Val Lys Glu
1230                1235                1240                1245 aaa tgg gaa agt cta aat gct gta act agc aat tgg caa aag caa gtg              3793
Lys Trp Glu Ser Leu Asn Ala Val Thr Ser Asn Trp Gln Lys Gln Val
            1250                1255                1260 gac aag gca ttg gag aaa ctc aga gac ctg cag gga gct atg gat gac              3841
Asp Lys Ala Leu Glu Lys Leu Arg Asp Leu Gln Gly Ala Met Asp Asp
        1265                1270                1275 ctg gac gct gac atg aag gag gca gag tcc gtg cgg aat ggc tgg aag              3889
Leu Asp Ala Asp Met Lys Glu Ala Glu Ser Val Arg Asn Gly Trp Lys
    1280                1285                1290 ccc gtg gga gac tta ctc att gac tcg ctg cag gat cac att gaa aaa              3937
Pro Val Gly Asp Leu Leu Ile Asp Ser Leu Gln Asp His Ile Glu Lys
1295                1300                1305 atc atg gca ttt aga gaa gaa att gca cca atc aac ttt aaa gtt aaa              3985
Ile Met Ala Phe Arg Glu Glu Ile Ala Pro Ile Asn Phe Lys Val Lys
1310                1315                1320                1325 acg gtg aat gat tta tcc agt cag ctg tct cca ctt gac ctg cat ccc              4033
Thr Val Asn Asp Leu Ser Ser Gln Leu Ser Pro Leu Asp Leu His Pro
            1330                1335                1340 tct cta aag atg tct cgc cag cta gat gac ctt aat atg cga tgg aaa              4081
Ser Leu Lys Met Ser Arg Gln Leu Asp Asp Leu Asn Met Arg Trp Lys
        1345                1350                1355 ctt tta cag gtt tct gtg gat gat cgc ctt aaa cag ctt cag gaa gcc              4129
Leu Leu Gln Val Ser Val Asp Asp Arg Leu Lys Gln Leu Gln Glu Ala
    1360                1365                1370 cac aga gat ttt gga cca tcc tct cag cat ttt ctc tct acg tca gtc              4177
His Arg Asp Phe Gly Pro Ser Ser Gln His Phe Leu Ser Thr Ser Val
1375                1380                1385 cag ctg ccg tgg caa aga tcc att tca cat aat aaa gtg ccc tat tac              4225
Gln Leu Pro Trp Gln Arg Ser Ile Ser His Asn Lys Val Pro Tyr Tyr
1390                1395                1400                1405 atc aac cat caa aca cag acc acc tgt tgg gac cat cct aaa atg acc              4273
Ile Asn His Gln Thr Gln Thr Thr Cys Trp Asp His Pro Lys Met Thr
            1410                1415                1420 gaa ctc ttt caa tcc ctt gct gac ctg aat aat gta cgt ttt tct gcc              4321
Glu Leu Phe Gln Ser Leu Ala Asp Leu Asn Asn Val Arg Phe Ser Ala
        1425                1430                1435 tac cgt aca gca atc aaa atc cga aga cta caa aaa gca cta tgt ttg              4369
Tyr Arg Thr Ala Ile Lys Ile Arg Arg Leu Gln Lys Ala Leu Cys Leu
    1440                1445                1450
```

-continued

```
gat ctc tta gag ttg agt aca aca aat gaa att ttc aaa cag cac aag     4417
Asp Leu Leu Glu Leu Ser Thr Thr Asn Glu Ile Phe Lys Gln His Lys
    1455                1460                1465 ttg aac caa aat gac cag ctc ctc agt gtt cca gat gtc atc aac tgt     4465
Leu Asn Gln Asn Asp Gln Leu Leu Ser Val Pro Asp Val Ile Asn Cys
1470                1475                1480                1485 ctg aca aca act tat gat gga ctt gag caa atg cat aag gac ctg gtc     4513
Leu Thr Thr Thr Tyr Asp Gly Leu Glu Gln Met His Lys Asp Leu Val
                1490                1495                1500 aac gtt cca ctc tgt gtt gat atg tgt ctc aat tgg ttg ctc aat gtc     4561
Asn Val Pro Leu Cys Val Asp Met Cys Leu Asn Trp Leu Leu Asn Val
            1505                1510                1515 tat gac acg ggt cga act gga aaa att aga gtg cag agt ctg aag att     4609
Tyr Asp Thr Gly Arg Thr Gly Lys Ile Arg Val Gln Ser Leu Lys Ile
        1520                1525                1530 gga tta atg tct ctc tcc aaa ggt ctc ttg gaa gaa aaa tac aga tat     4657
Gly Leu Met Ser Leu Ser Lys Gly Leu Leu Glu Glu Lys Tyr Arg Tyr
    1535                1540                1545 ctc ttt aag gaa gtt gcg ggg ccg aca gaa atg tgt gac cag agg cag     4705
Leu Phe Lys Glu Val Ala Gly Pro Thr Glu Met Cys Asp Gln Arg Gln
1550                1555                1560                1565 ctg ggc ctg tta ctt cat gat gcc atc cag atc ccc cgg cag cta ggt     4753
Leu Gly Leu Leu Leu His Asp Ala Ile Gln Ile Pro Arg Gln Leu Gly
                1570                1575                1580 gaa gta gca gct ttt gga ggc agt aat att gag cct agt gtt cgc agc     4801
Glu Val Ala Ala Phe Gly Gly Ser Asn Ile Glu Pro Ser Val Arg Ser
            1585                1590                1595 tgc ttc caa cag aat aac aat aaa cca gaa ata agt gtg aaa gag ttt     4849
Cys Phe Gln Gln Asn Asn Asn Lys Pro Glu Ile Ser Val Lys Glu Phe
        1600                1605                1610 ata gat tgg atg cat ttg gaa cca cag tcc atg gtt tgg ctc cca gtt     4897
Ile Asp Trp Met His Leu Glu Pro Gln Ser Met Val Trp Leu Pro Val
    1615                1620                1625 tta cat cga gtg gca gca gcg gag act gca aaa cat cag gcc aaa tgc     4945
Leu His Arg Val Ala Ala Ala Glu Thr Ala Lys His Gln Ala Lys Cys
1630                1635                1640                1645 aac atc tgt aaa gaa tgt cca att gtc ggg ttc agg tat aga agc ctt     4993
Asn Ile Cys Lys Glu Cys Pro Ile Val Gly Phe Arg Tyr Arg Ser Leu
                1650                1655                1660 aag cat ttt aac tat gat gtc tgc cag agt tgt ttc ttt tcg ggt cga     5041
Lys His Phe Asn Tyr Asp Val Cys Gln Ser Cys Phe Phe Ser Gly Arg
            1665                1670                1675 aca gca aaa ggt cac aaa tta cat tac cca atg gtg gaa tat tgt ata     5089
Thr Ala Lys Gly His Lys Leu His Tyr Pro Met Val Glu Tyr Cys Ile
        1680                1685                1690 cct aca aca tct ggg gaa gat gta cga gac ttc aca aag gta ctt aag     5137
Pro Thr Thr Ser Gly Glu Asp Val Arg Asp Phe Thr Lys Val Leu Lys
    1695                1700                1705 aac aag ttc agg tcg aag aag tac ttt gcc aaa cac cct cga ctt ggt     5185
Asn Lys Phe Arg Ser Lys Lys Tyr Phe Ala Lys His Pro Arg Leu Gly
1710                1715                1720                1725 tac ctg cct gtc cag aca gtt ctt gaa ggt gac aac tta gag act cct     5233
Tyr Leu Pro Val Gln Thr Val Leu Glu Gly Asp Asn Leu Glu Thr Pro
                1730                1735                1740 atc aca ctc atc agt atg tgg cca gag cac tat gac ccc tca caa tct     5281
Ile Thr Leu Ile Ser Met Trp Pro Glu His Tyr Asp Pro Ser Gln Ser
            1745                1750                1755 cct caa ctg ttt cat gat gac acc cat tca aga ata gaa caa tat gcc     5329
Pro Gln Leu Phe His Asp Asp Thr His Ser Arg Ile Glu Gln Tyr Ala
        1760                1765                1770
```

-continued

```
aca cga ctg gcc cag atg gaa agg act aat ggg tct ttt ctc act gat      5377
Thr Arg Leu Ala Gln Met Glu Arg Thr Asn Gly Ser Phe Leu Thr Asp
    1775                1780                1785 agc agc tcc acc aca gga agt gtg gaa gac gag cac gcc ctc atc cag      5425
Ser Ser Ser Thr Thr Gly Ser Val Glu Asp Glu His Ala Leu Ile Gln
1790                1795                1800                1805 cag tat tgc caa aca ctc gga gga gag tcc cca gtg agc cag ccg cag      5473
Gln Tyr Cys Gln Thr Leu Gly Gly Glu Ser Pro Val Ser Gln Pro Gln
            1810                1815                1820 agc cca gct cag atc ctg aag tca gta gag agg gaa gaa cgt gga gaa      5521
Ser Pro Ala Gln Ile Leu Lys Ser Val Glu Arg Glu Glu Arg Gly Glu
                1825                1830                1835 ctg gag agg atc att gct gac ctg gag gaa gaa caa aga aat cta cag      5569
Leu Glu Arg Ile Ile Ala Asp Leu Glu Glu Glu Gln Arg Asn Leu Gln
        1840                1845                1850 gtg gag tat gag cag ctg aag gac cag cac ctc cga agg ggg ctc cct      5617
Val Glu Tyr Glu Gln Leu Lys Asp Gln His Leu Arg Arg Gly Leu Pro
    1855                1860                1865 gtc ggt tca ccg cca gag tcg att ata tct ccc cat cac acg tct gag      5665
Val Gly Ser Pro Pro Glu Ser Ile Ile Ser Pro His His Thr Ser Glu
1870                1875                1880                1885 gat tca gaa ctt ata gca gaa gca aaa ctc ctc agg cag cac aaa ggt      5713
Asp Ser Glu Leu Ile Ala Glu Ala Lys Leu Leu Arg Gln His Lys Gly
            1890                1895                1900 cgg ctg gag gct agg atg cag att tta gaa gat cac aat aaa cag ctg      5761
Arg Leu Glu Ala Arg Met Gln Ile Leu Glu Asp His Asn Lys Gln Leu
                1905                1910                1915 gag tct cag ctc cac cgc ctc cga cag ctg ctg gag cag cct gaa tct      5809
Glu Ser Gln Leu His Arg Leu Arg Gln Leu Leu Glu Gln Pro Glu Ser
        1920                1925                1930 gat tcc cga atc aat ggt gtt tcc cca tgg gct tct cct cag cat tct      5857
Asp Ser Arg Ile Asn Gly Val Ser Pro Trp Ala Ser Pro Gln His Ser
    1935                1940                1945 gca ctg agc tac tcg ctt gat cca gat gcc tcc ggc cca cag ttc cac      5905
Ala Leu Ser Tyr Ser Leu Asp Pro Asp Ala Ser Gly Pro Gln Phe His
1950                1955                1960                1965 cag gca gcg gga gag gac ctg ctg gcc cca ccg cac gac acc agc acg      5953
Gln Ala Ala Gly Glu Asp Leu Leu Ala Pro Pro His Asp Thr Ser Thr
            1970                1975                1980 gat ctc acg gag gtc atg gag cag att cac agc acg ttt cca tct tgc      6001
Asp Leu Thr Glu Val Met Glu Gln Ile His Ser Thr Phe Pro Ser Cys
                1985                1990                1995 tgc cca aat gtt ccc agc agg cca cag gca atg taa tcactagt             6045
Cys Pro Asn Val Pro Ser Arg Pro Gln Ala Met
        2000                2005
```

<210> SEQ ID NO 8
<211> LENGTH: 2008
<212> TYPE: PRT
<213> ORGANISM: Artificial Sequence
<220> FEATURE:
<221> NAME/KEY: misc_feature
<222> LOCATION: (239) ... (250)
<223> OTHER INFORMATION: Description of Artificial Sequence: Chimeric;
      Xaa = Unknown

<400> SEQUENCE: 8

```
Met Ala Lys Tyr Gly Glu His Glu Ala Ser Pro Asp Asn Gly Gln Asn
 1               5                  10                  15

Glu Phe Ser Asp Ile Ile Glu Ser Arg Ser Asp Glu His Asn Asp Val
            20                  25                  30
```

```
Gln Lys Lys Thr Phe Thr Lys Trp Ile Asn Ala Arg Phe Ser Lys Ser
     35                  40                  45

Gly Lys Pro Pro Ile Ser Asp Met Phe Ser Asp Leu Lys Asp Gly Arg
     50                  55                  60

Lys Leu Asp Leu Leu Glu Gly Leu Thr Gly Thr Ser Leu Pro Lys
 65              70                  75                  80

Glu Arg Gly Ser Thr Arg Val His Ala Leu Asn Asn Val Asn Arg Val
                 85                  90                  95

Leu Gln Val Leu His Gln Asn Asn Val Asp Leu Val Asn Ile Gly Gly
            100                 105                 110

Thr Asp Ile Val Asp Gly Asn Pro Lys Leu Thr Leu Gly Leu Leu Trp
            115                 120                 125

Ser Ile Ile Leu His Trp Gln Val Lys Asp Val Met Lys Asp Ile Met
130                 135                 140

Ser Asp Leu Gln Gln Thr Asn Ser Glu Lys Ile Leu Leu Ser Trp Val
145                 150                 155                 160

Arg Gln Thr Thr Arg Pro Tyr Ser Gln Val Asn Val Leu Asn Phe Thr
                165                 170                 175

Thr Ser Trp Thr Asp Gly Leu Ala Phe Asn Ala Val Leu His Arg His
            180                 185                 190

Lys Pro Asp Leu Phe Ser Trp Asp Arg Val Val Lys Met Ser Pro Ile
            195                 200                 205

Glu Arg Leu Glu His Ala Phe Ser Lys Ala His Thr Tyr Leu Gly Ile
            210                 215                 220

Glu Lys Leu Leu Asp Pro Glu Asp Val Ala Val His Leu Pro Xaa Xaa
225                 230                 235                 240

Xaa Xaa Xaa Xaa Xaa Xaa Xaa Xaa Xaa Val Glu Val Leu Pro Gln
                245                 250                 255

Gln Val Thr Ile Asp Ala Ile Arg Glu Val Thr Leu Pro Arg Lys
            260                 265                 270

Tyr Lys Lys Glu Cys Glu Glu Glu Ile His Ile Gln Ser Ala Val
            275                 280                 285

Leu Ala Glu Glu Gly Gln Ser Pro Arg Ala Glu Thr Pro Ser Thr Val
290                 295                 300

Thr Glu Val Asp Met Asp Leu Asp Ser Tyr Gln Ile Ala Leu Glu Glu
305                 310                 315                 320

Val Leu Thr Trp Leu Leu Ser Ala Glu Asp Thr Phe Gln Glu Gln Asp
                325                 330                 335

Asp Ile Ser Asp Asp Val Glu Glu Val Lys Glu Gln Phe Ala Thr His
            340                 345                 350

Glu Thr Phe Met Met Glu Leu Thr Ala His Gln Ser Ser Val Gly Ser
            355                 360                 365

Val Leu Gln Ala Gly Asn Gln Leu Met Thr Gln Gly Thr Leu Ser Glu
    370                 375                 380

Glu Glu Glu Phe Glu Ile Gln Glu Gln Met Thr Leu Leu Asn Ala Arg
385                 390                 395                 400

Trp Glu Ala Leu Arg Val Glu Ser Met Glu Arg Gln Ser Arg Leu His
                405                 410                 415

Asp Ala Leu Met Glu Leu Gln Lys Lys Gln Leu Gln Gln Leu Ser Ser
            420                 425                 430

Trp Leu Ala Leu Thr Glu Glu Arg Ile Gln Lys Met Glu Ser Pro Pro
            435                 440                 445
```

-continued

```
Leu Gly Asp Asp Leu Pro Ser Leu Gln Lys Leu Leu Gln Glu His Lys
    450                 455                 460

Ser Leu Gln Asn Asp Leu Glu Ala Glu Gln Val Lys Val Asn Ser Leu
465                 470                 475                 480

Thr His Met Val Val Ile Val Asp Glu Asn Ser Gly Glu Ser Ala Thr
                    485                 490                 495

Ala Leu Leu Glu Asp Gln Leu Gln Lys Leu Gly Glu Arg Trp Thr Ala
                500                 505                 510

Val Cys Arg Trp Thr Glu Glu Arg Trp Asn Arg Leu Gln Glu Ile Ser
            515                 520                 525

Ile Leu Trp Gln Glu Leu Leu Glu Glu Gln Cys Leu Leu Glu Ala Trp
        530                 535                 540

Leu Thr Glu Lys Glu Glu Ala Leu Asn Lys Val Gln Thr Ser Asn Phe
545                 550                 555                 560

Lys Asp Gln Lys Glu Leu Ser Val Ser Val Arg Arg Leu Ala Ile Leu
                    565                 570                 575

Lys Glu Asp Met Glu Met Lys Arg Gln Thr Leu Asp Gln Leu Ser Glu
                580                 585                 590

Ile Gly Gln Asp Val Gly Gln Leu Leu Ser Asn Pro Lys Ala Ser Lys
            595                 600                 605

Lys Met Asn Ser Asp Ser Glu Glu Leu Thr Gln Arg Trp Asp Ser Leu
        610                 615                 620

Val Gln Arg Leu Glu Asp Ser Ser Asn Gln Val Thr Gln Ala Val Ala
625                 630                 635                 640

Lys Leu Gly Met Ser Gln Ile Pro Gln Lys Asp Leu Leu Glu Thr Val
                    645                 650                 655

His Val Arg Glu Lys Gly Met Val Lys Lys Pro Lys Gln Glu Leu Pro
                660                 665                 670

Pro Pro Leu Thr Lys Ala Glu His Ala Met Gln Lys Arg Ser Thr Thr
            675                 680                 685

Glu Leu Gly Glu Asn Leu Gln Glu Leu Arg Asp Leu Thr Gln Glu Met
        690                 695                 700

Glu Val His Ala Glu Lys Leu Lys Trp Leu Asn Arg Thr Glu Leu Glu
705                 710                 715                 720

Met Leu Ser Asp Lys Ser Leu Ser Leu Pro Glu Arg Asp Lys Ile Ser
                    725                 730                 735

Glu Ser Leu Arg Thr Val Asn Met Thr Trp Asn Lys Ile Cys Arg Glu
                740                 745                 750

Val Pro Thr Thr Leu Lys Glu Cys Ile Gln Glu Pro Ser Ser Val Ser
            755                 760                 765

Gln Thr Arg Ile Ala Ala His Pro Asn Val Gln Lys Val Val Leu Val
        770                 775                 780

Ser Ser Ala Ser Asp Ile Pro Val Gln Ser His Arg Thr Ser Glu Ile
785                 790                 795                 800

Ser Ile Pro Ala Asp Leu Asp Lys Thr Ile Thr Glu Leu Ala Asp Trp
                    805                 810                 815

Leu Val Leu Ile Asp Gln Met Leu Lys Ser Asn Ile Val Thr Val Gly
                820                 825                 830

Asp Val Glu Glu Ile Asn Lys Thr Val Ser Arg Met Lys Ile Thr Lys
            835                 840                 845

Ala Asp Leu Glu Gln Arg His Pro Gln Leu Asp Tyr Val Phe Thr Leu
        850                 855                 860

Ala Gln Asn Leu Lys Asn Lys Ala Ser Ser Ser Asp Met Arg Thr Ala
```

-continued

```
            865                 870                 875                 880
        Ile Thr Glu Lys Leu Glu Arg Val Lys Asn Gln Trp Asp Gly Thr Gln
                        885                 890                 895
        His Gly Val Glu Leu Arg Gln Gln Leu Glu Asp Met Ile Ile Asp
                    900                 905                 910
        Ser Leu Gln Trp Asp Asp His Arg Glu Glu Thr Glu Leu Met Arg
                    915                 920                 925
        Lys Tyr Glu Ala Arg Leu Tyr Ile Leu Gln Gln Ala Arg Arg Asp Pro
                    930                 935                 940
        Leu Thr Lys Gln Ile Ser Asp Asn Gln Ile Leu Leu Gln Glu Leu Gly
        945                 950                 955                 960
        Pro Gly Asp Gly Ile Val Met Ala Phe Asp Asn Val Leu Gln Lys Leu
                            965                 970                 975
        Leu Glu Glu Tyr Gly Ser Asp Asp Thr Arg Asn Val Lys Glu Thr Thr
                        980                 985                 990
        Glu Tyr Leu Lys Thr Ser Trp Ile Asn Leu Lys Gln Ser Ile Ala Asp
                    995                 1000                1005
        Arg Gln Asn Ala Leu Glu Ala Glu Trp Arg Thr Val Gln Ala Ser Arg
            1010                1015                1020
        Arg Asp Leu Glu Asn Phe Leu Lys Trp Ile Gln Glu Ala Glu Thr Thr
        1025                1030                1035                1040
        Val Asn Val Leu Val Asp Ala Ser His Arg Glu Asn Ala Leu Gln Asp
                            1045                1050                1055
        Ser Ile Leu Ala Arg Glu Leu Lys Gln Gln Met Gln Asp Ile Gln Ala
                        1060                1065                1070
        Glu Ile Asp Ala His Asn Asp Ile Phe Lys Ser Ile Asp Gly Asn Arg
                        1075                1080                1085
        Gln Lys Met Val Lys Ala Leu Gly Asn Ser Glu Glu Ala Thr Met Leu
                        1090                1095                1100
        Gln His Arg Leu Asp Asp Met Asn Gln Arg Trp Asn Asp Leu Lys Ala
        1105                1110                1115                1120
        Lys Ser Ala Ser Ile Arg Ala His Leu Glu Ala Ser Ala Glu Lys Trp
                        1125                1130                1135
        Asn Arg Leu Leu Met Ser Leu Glu Glu Leu Ile Lys Trp Leu Asn Met
                        1140                1145                1150
        Lys Asp Glu Glu Leu Lys Lys Gln Met Pro Ile Gly Gly Asp Val Pro
                        1155                1160                1165
        Ala Leu Gln Leu Gln Tyr Asp His Cys Lys Ala Leu Arg Arg Glu Leu
        1170                1175                1180
        Lys Glu Lys Glu Tyr Ser Val Leu Asn Ala Val Asp Gln Ala Arg Val
        1185                1190                1195                1200
        Phe Leu Ala Asp Gln Pro Ile Glu Ala Pro Glu Glu Pro Arg Arg Asn
                        1205                1210                1215
        Leu Gln Ser Lys Thr Glu Leu Thr Pro Glu Glu Arg Ala Gln Lys Ile
                    1220                1225                1230
        Ala Lys Ala Met Arg Lys Gln Ser Ser Glu Val Lys Glu Lys Trp Glu
                    1235                1240                1245
        Ser Leu Asn Ala Val Thr Ser Asn Trp Gln Lys Gln Val Asp Lys Ala
        1250                1255                1260
        Leu Glu Lys Leu Arg Asp Leu Gln Gly Ala Met Asp Asp Leu Asp Ala
        1265                1270                1275                1280
        Asp Met Lys Glu Ala Glu Ser Val Arg Asn Gly Trp Lys Pro Val Gly
                    1285                1290                1295
```

-continued

Asp Leu Leu Ile Asp Ser Leu Gln Asp His Ile Glu Lys Ile Met Ala
            1300                1305                1310
Phe Arg Glu Glu Ile Ala Pro Ile Asn Phe Lys Val Lys Thr Val Asn
        1315                1320                1325
Asp Leu Ser Ser Gln Leu Ser Pro Leu Asp Leu His Pro Ser Leu Lys
    1330                1335                1340
Met Ser Arg Gln Leu Asp Asp Leu Asn Met Arg Trp Lys Leu Leu Gln
1345                1350                1355                1360
Val Ser Val Asp Asp Arg Leu Lys Gln Leu Gln Glu Ala His Arg Asp
            1365                1370                1375
Phe Gly Pro Ser Ser Gln His Phe Leu Ser Thr Ser Val Gln Leu Pro
        1380                1385                1390
Trp Gln Arg Ser Ile Ser His Asn Lys Val Pro Tyr Tyr Ile Asn His
    1395                1400                1405
Gln Thr Gln Thr Thr Cys Trp Asp His Pro Lys Met Thr Glu Leu Phe
    1410                1415                1420
Gln Ser Leu Ala Asp Leu Asn Asn Val Arg Phe Ser Ala Tyr Arg Thr
1425                1430                1435                1440
Ala Ile Lys Ile Arg Arg Leu Gln Lys Ala Leu Cys Leu Asp Leu Leu
            1445                1450                1455
Glu Leu Ser Thr Thr Asn Glu Ile Phe Lys Gln His Lys Leu Asn Gln
        1460                1465                1470
Asn Asp Gln Leu Leu Ser Val Pro Asp Val Ile Asn Cys Leu Thr Thr
    1475                1480                1485
Thr Tyr Asp Gly Leu Glu Gln Met His Lys Asp Leu Val Asn Val Pro
    1490                1495                1500
Leu Cys Val Asp Met Cys Leu Asn Trp Leu Leu Asn Val Tyr Asp Thr
1505                1510                1515                1520
Gly Arg Thr Gly Lys Ile Arg Val Gln Ser Leu Lys Ile Gly Leu Met
            1525                1530                1535
Ser Leu Ser Lys Gly Leu Leu Glu Glu Lys Tyr Arg Tyr Leu Phe Lys
        1540                1545                1550
Glu Val Ala Gly Pro Thr Glu Met Cys Asp Gln Arg Gln Leu Gly Leu
    1555                1560                1565
Leu Leu His Asp Ala Ile Gln Ile Pro Arg Gln Leu Gly Glu Val Ala
    1570                1575                1580
Ala Phe Gly Gly Ser Asn Ile Glu Pro Ser Val Arg Ser Cys Phe Gln
1585                1590                1595                1600
Gln Asn Asn Asn Lys Pro Glu Ile Ser Val Lys Glu Phe Ile Asp Trp
            1605                1610                1615
Met His Leu Glu Pro Gln Ser Met Val Trp Leu Pro Val Leu His Arg
        1620                1625                1630
Val Ala Ala Ala Glu Thr Ala Lys His Gln Ala Lys Cys Asn Ile Cys
    1635                1640                1645
Lys Glu Cys Pro Ile Val Gly Phe Arg Tyr Arg Ser Leu Lys His Phe
    1650                1655                1660
Asn Tyr Asp Val Cys Gln Ser Cys Phe Phe Ser Gly Arg Thr Ala Lys
1665                1670                1675                1680
Gly His Lys Leu His Tyr Pro Met Val Glu Tyr Cys Ile Pro Thr Thr
            1685                1690                1695
Ser Gly Glu Asp Val Arg Asp Phe Thr Lys Val Leu Lys Asn Lys Phe
    1700                1705                1710

-continued

Arg Ser Lys Lys Tyr Phe Ala Lys His Pro Arg Leu Gly Tyr Leu Pro
    1715                1720                1725

Val Gln Thr Val Leu Glu Gly Asp Asn Leu Glu Thr Pro Ile Thr Leu
1730                1735                1740

Ile Ser Met Trp Pro Glu His Tyr Asp Pro Ser Gln Ser Pro Gln Leu
1745                1750                1755                1760

Phe His Asp Asp Thr His Ser Arg Ile Glu Gln Tyr Ala Thr Arg Leu
            1765                1770                1775

Ala Gln Met Glu Arg Thr Asn Gly Ser Phe Leu Thr Asp Ser Ser Ser
        1780                1785                1790

Thr Thr Gly Ser Val Glu Asp Glu His Ala Leu Ile Gln Gln Tyr Cys
    1795                1800                1805

Gln Thr Leu Gly Gly Glu Ser Pro Val Ser Gln Pro Gln Ser Pro Ala
1810                1815                1820

Gln Ile Leu Lys Ser Val Glu Arg Glu Glu Arg Gly Glu Leu Glu Arg
1825                1830                1835                1840

Ile Ile Ala Asp Leu Glu Glu Glu Gln Arg Asn Leu Gln Val Glu Tyr
            1845                1850                1855

Glu Gln Leu Lys Asp Gln His Leu Arg Arg Gly Leu Pro Val Gly Ser
        1860                1865                1870

Pro Pro Glu Ser Ile Ile Ser Pro His His Thr Ser Glu Asp Ser Glu
    1875                1880                1885

Leu Ile Ala Glu Ala Lys Leu Leu Arg Gln His Lys Gly Arg Leu Glu
    1890                1895                1900

Ala Arg Met Gln Ile Leu Glu Asp His Asn Lys Gln Leu Glu Ser Gln
1905                1910                1915                1920

Leu His Arg Leu Arg Gln Leu Leu Glu Gln Pro Glu Ser Asp Ser Arg
        1925                1930                1935

Ile Asn Gly Val Ser Pro Trp Ala Ser Pro Gln His Ser Ala Leu Ser
            1940                1945                1950

Tyr Ser Leu Asp Pro Asp Ala Ser Gly Pro Gln Phe His Gln Ala Ala
        1955                1960                1965

Gly Glu Asp Leu Leu Ala Pro Pro His Asp Thr Ser Thr Asp Leu Thr
    1970                1975                1980

Glu Val Met Glu Gln Ile His Ser Thr Phe Pro Ser Cys Cys Pro Asn
1985                1990                1995                2000

Val Pro Ser Arg Pro Gln Ala Met
            2005

<210> SEQ ID NO 9
<211> LENGTH: 10320
<212> TYPE: DNA
<213> ORGANISM: Artificial Sequence
<220> FEATURE:
<221> NAME/KEY: CDS
<222> LOCATION: (11)..(10312)
<220> FEATURE:
<223> OTHER INFORMATION: Description of Artificial Sequence: Full length
      utrophin construct
<220> FEATURE:
<221> NAME/KEY: misc_feature
<222> LOCATION: (724)..(758)
<223> OTHER INFORMATION: Precise residue is left open

<400> SEQUENCE: 9
actagtcaag atg gcc aag tat gga gaa cat gaa gcc agt cct gac aat         49
           Met Ala Lys Tyr Gly Glu His Glu Ala Ser Pro Asp Asn
           1               5                   10

-continued

| | |
|---|---|
| ggg cag aac gaa ttc agt gac atc att gag tcc aga tct gat gaa cac<br>Gly Gln Asn Glu Phe Ser Asp Ile Ile Glu Ser Arg Ser Asp Glu His<br>15                    20                    25 | 97 |
| aat gat gta cag aag aaa acc ttt acc aaa tgg ata aac gct cga ttt<br>Asn Asp Val Gln Lys Lys Thr Phe Thr Lys Trp Ile Asn Ala Arg Phe<br>30                    35                    40                    45 | 145 |
| tcc aag agt ggg aaa cca ccc atc agt gat atg ttc tca gac ctc aaa<br>Ser Lys Ser Gly Lys Pro Pro Ile Ser Asp Met Phe Ser Asp Leu Lys<br>                  50                    55                    60 | 193 |
| gat ggg aga aag ctc ttg gat ctt ctc gaa ggc ctc aca gga aca tca<br>Asp Gly Arg Lys Leu Leu Asp Leu Leu Glu Gly Leu Thr Gly Thr Ser<br>65                    70                    75 | 241 |
| ttg cca aag gaa cgt ggt tcc aca agg gtg cat gcc tta aac aat gtc<br>Leu Pro Lys Glu Arg Gly Ser Thr Arg Val His Ala Leu Asn Asn Val<br>        80                    85                    90 | 289 |
| aac cga gtg cta cag gtt tta cat cag aac aat gtg gac ttg gtg aat<br>Asn Arg Val Leu Gln Val Leu His Gln Asn Asn Val Asp Leu Val Asn<br>95                    100                   105 | 337 |
| att gga ggc acg gac att gtg gat gga aat ccc aag ctg act tta ggg<br>Ile Gly Gly Thr Asp Ile Val Asp Gly Asn Pro Lys Leu Thr Leu Gly<br>110                   115                    120                  125 | 385 |
| tta ctc tgg agc atc att ctg cac tgg cag gtg aag gat gtc atg aaa<br>Leu Leu Trp Ser Ile Ile Leu His Trp Gln Val Lys Asp Val Met Lys<br>                  130                    135                    140 | 433 |
| gat atc atg tca gac ctg cag cag aca aac agc gag aag atc ctg ctg<br>Asp Ile Met Ser Asp Leu Gln Gln Thr Asn Ser Glu Lys Ile Leu Leu<br>145                   150                    155 | 481 |
| agc tgg gtg cgg cag acc acc agg ccc tac agt caa gtc aac gtc ctc<br>Ser Trp Val Arg Gln Thr Thr Arg Pro Tyr Ser Gln Val Asn Val Leu<br>                160                    165                    170 | 529 |
| aac ttc acc acc agc tgg acc gat gga ctc gcg ttc aac gcc gtg ctc<br>Asn Phe Thr Thr Ser Trp Thr Asp Gly Leu Ala Phe Asn Ala Val Leu<br>175                   180                    185 | 577 |
| cac cgg cac aaa cca gat ctc ttc agc tgg gac aga gtg gtc aaa atg<br>His Arg His Lys Pro Asp Leu Phe Ser Trp Asp Arg Val Val Lys Met<br>190                   195                    200                  205 | 625 |
| tcc cca att gag aga ctt gaa cat gct ttt agc aag gcc cac act tat<br>Ser Pro Ile Glu Arg Leu Glu His Ala Phe Ser Lys Ala His Thr Tyr<br>                210                    215                    220 | 673 |
| ttg gga att gaa aag ctt cta gat cct gaa gat gtt gct gtg cat ctc<br>Leu Gly Ile Glu Lys Leu Leu Asp Pro Glu Asp Val Ala Val His Leu<br>                225                    230                    235 | 721 |
| ccn nnn nnn nnn nnn nnn nnn nnn nnn nnn nnn ncc gtt gag gtg<br>Pro Xaa Xaa Xaa Xaa Xaa Xaa Xaa Xaa Xaa Xaa Xaa Val Glu Val<br>      240                    245                    250 | 769 |
| ctt cct cag caa gtc acg ata gat gcc atc cga gag gtg gag act ctc<br>Leu Pro Gln Gln Val Thr Ile Asp Ala Ile Arg Glu Val Glu Thr Leu<br>255                   260                    265 | 817 |
| cca agg aag tat aag aaa gaa tgt gaa gag gaa gaa att cat atc cag<br>Pro Arg Lys Tyr Lys Lys Glu Cys Glu Glu Glu Glu Ile His Ile Gln<br>270                   275                    280                  285 | 865 |
| agt gca gtg ctg gca gag gaa ggc cag agt ccc cga gct gag acc cct<br>Ser Ala Val Leu Ala Glu Glu Gly Gln Ser Pro Arg Ala Glu Thr Pro<br>                290                    295                    300 | 913 |
| agc acc gtc act gaa gtg gac atg gat ttg gac agc tac cag ata gcg<br>Ser Thr Val Thr Glu Val Asp Met Asp Leu Asp Ser Tyr Gln Ile Ala<br>                305                    310                    315 | 961 |
| cta gag gaa gtg ctg acg tgg ctg ctg tcc gcg gag gac acg ttc cag<br>Leu Glu Glu Val Leu Thr Trp Leu Leu Ser Ala Glu Asp Thr Phe Gln<br>320                   325                    330 | 1009 |

```
gag caa gat gac att tct gat gat gtc gaa gaa gtc aaa gag cag ttt      1057
Glu Gln Asp Asp Ile Ser Asp Asp Val Glu Glu Val Lys Glu Gln Phe
        335                 340                 345 gct acc cat gaa act ttt atg atg gag ctg aca gca cac cag agc agc      1105
Ala Thr His Glu Thr Phe Met Met Glu Leu Thr Ala His Gln Ser Ser
350                 355                 360                 365 gtg ggg agc gtc ctg cag gct ggc aac cag ctg atg aca caa ggg act      1153
Val Gly Ser Val Leu Gln Ala Gly Asn Gln Leu Met Thr Gln Gly Thr
                370                 375                 380 ctg tca gag gag gag gag ttt gag atc cag gaa cag atg acc ttg ctg      1201
Leu Ser Glu Glu Glu Glu Phe Glu Ile Gln Glu Gln Met Thr Leu Leu
            385                 390                 395 aat gca agg tgg gag gcg ctc cgg gtg gag agc atg gag agg cag tcc      1249
Asn Ala Arg Trp Glu Ala Leu Arg Val Glu Ser Met Glu Arg Gln Ser
        400                 405                 410 cgg ctg cac gac gct ctg atg gag ctg cag aag aaa cag ctg cag cag      1297
Arg Leu His Asp Ala Leu Met Glu Leu Gln Lys Lys Gln Leu Gln Gln
    415                 420                 425 ctc tca agc tgg ctg gcc ctc aca gaa gag cgc att cag aag atg gag      1345
Leu Ser Ser Trp Leu Ala Leu Thr Glu Glu Arg Ile Gln Lys Met Glu
430                 435                 440                 445 agc cct ccg ctg ggt gat gac ctg ccc tcc ctg cag aag ctg ctt caa      1393
Ser Pro Pro Leu Gly Asp Asp Leu Pro Ser Leu Gln Lys Leu Leu Gln
                450                 455                 460 gaa cat aaa agt ttg caa aat gac ctt gaa gct gaa cag gtg aag gta      1441
Glu His Lys Ser Leu Gln Asn Asp Leu Glu Ala Glu Gln Val Lys Val
            465                 470                 475 aat tcc tta act cac atg gtg gtg att gtg gat gaa aac agt ggg gag      1489
Asn Ser Leu Thr His Met Val Val Ile Val Asp Glu Asn Ser Gly Glu
        480                 485                 490 agt gcc aca gct ctt ctg gaa gat cag tta cag aaa ctg ggt gag cgc      1537
Ser Ala Thr Ala Leu Leu Glu Asp Gln Leu Gln Lys Leu Gly Glu Arg
    495                 500                 505 tgg aca gct gta tgc cgc tgg act gaa gaa cgt tgg aac agg ttg caa      1585
Trp Thr Ala Val Cys Arg Trp Thr Glu Glu Arg Trp Asn Arg Leu Gln
510                 515                 520                 525 gaa atc agt att ctg tgg cag gaa tta ttg gaa gag cag tgt ctg ttg      1633
Glu Ile Ser Ile Leu Trp Gln Glu Leu Leu Glu Glu Gln Cys Leu Leu
                530                 535                 540 gag gct tgg ctc acc gaa aag gaa gag gct ttg aat aaa gtt caa acc      1681
Glu Ala Trp Leu Thr Glu Lys Glu Glu Ala Leu Asn Lys Val Gln Thr
            545                 550                 555 agc aac ttt aaa gac cag aag gaa cta agt gtc agt gtc cgg cgt ctg      1729
Ser Asn Phe Lys Asp Gln Lys Glu Leu Ser Val Ser Val Arg Arg Leu
        560                 565                 570 gct ata ttg aag gaa gac atg gaa atg aag agg cag act ctg gat caa      1777
Ala Ile Leu Lys Glu Asp Met Glu Met Lys Arg Gln Thr Leu Asp Gln
    575                 580                 585 ctg agt gag att ggc cag gat gtg ggc caa tta ctc agt aat ccc aag      1825
Leu Ser Glu Ile Gly Gln Asp Val Gly Gln Leu Leu Ser Asn Pro Lys
590                 595                 600                 605 gca tct aag aag atg aac agt gac tct gag gag cta aca cag aga tgg      1873
Ala Ser Lys Lys Met Asn Ser Asp Ser Glu Glu Leu Thr Gln Arg Trp
                610                 615                 620 gat tct ctg gtt cag aga ctc gaa gac tct tct aac cag gtg act cag      1921
Asp Ser Leu Val Gln Arg Leu Glu Asp Ser Ser Asn Gln Val Thr Gln
            625                 630                 635 gcg gta gcg aag ctc ggc atg tcc cag att cca cag aag gac cta ttg      1969
Ala Val Ala Lys Leu Gly Met Ser Gln Ile Pro Gln Lys Asp Leu Leu
```

-continued

| | |
|---|---|
| gag acc gtt cat gtg aga gaa aaa ggg atg gtg aag aag ccc aag cag<br>Glu Thr Val His Val Arg Glu Lys Gly Met Val Lys Lys Pro Lys Gln<br>655                        660                        665 | 2017 |
| gaa ctg cct cct ccg ttg ggc cca aag aag aga cag atc cat gtg gat<br>Glu Leu Pro Pro Pro Leu Gly Pro Lys Lys Arg Gln Ile His Val Asp<br>670                        675                        680                        685 | 2065 |
| att gaa gct aag aaa aag ttt gat gct ata agt gca gag ctg ttg aac<br>Ile Glu Ala Lys Lys Lys Phe Asp Ala Ile Ser Ala Glu Leu Leu Asn<br>                    690                        695                        700 | 2113 |
| tgg att ttg aaa tgg aaa act gcc att cag acc aca gag ata aaa gag<br>Trp Ile Leu Lys Trp Lys Thr Ala Ile Gln Thr Thr Glu Ile Lys Glu<br>705                        710                        715 | 2161 |
| tat atg aag atg caa gac act tcc gaa atg aaa aag aag ttg aag gca<br>Tyr Met Lys Met Gln Asp Thr Ser Glu Met Lys Lys Lys Leu Lys Ala<br>                    720                        725                        730 | 2209 |
| tta gaa aaa gaa cag aga gaa aga atc ccc aga gca gat gaa tta aac<br>Leu Glu Lys Glu Gln Arg Glu Arg Ile Pro Arg Ala Asp Glu Leu Asn<br>735                        740                        745 | 2257 |
| caa act gga caa atc ctt gtg gag caa atg gga aaa gaa ggc ctt cct<br>Gln Thr Gly Gln Ile Leu Val Glu Gln Met Gly Lys Glu Gly Leu Pro<br>750                        755                        760                        765 | 2305 |
| act gaa gaa ata aaa aat gtt ctg gag aag gtt tca tca gaa tgg aag<br>Thr Glu Glu Ile Lys Asn Val Leu Glu Lys Val Ser Ser Glu Trp Lys<br>                    770                        775                        780 | 2353 |
| aat gta tct caa cat ttg gaa gat cta gaa aga aag att cag cta cag<br>Asn Val Ser Gln His Leu Glu Asp Leu Glu Arg Lys Ile Gln Leu Gln<br>785                        790                        795 | 2401 |
| gaa gat ata aat gct tat ttc aag cag ctt gat gag ctt gaa aag gtc<br>Glu Asp Ile Asn Ala Tyr Phe Lys Gln Leu Asp Glu Leu Glu Lys Val<br>                    800                        805                        810 | 2449 |
| atc aag aca aag gag gag tgg gta aaa cac act tcc att tct gaa tct<br>Ile Lys Thr Lys Glu Glu Trp Val Lys His Thr Ser Ile Ser Glu Ser<br>815                        820                        825 | 2497 |
| tcc cgg cag tcc ttg cca agc ttg aag gat tcc tgt cag cgg gaa ttg<br>Ser Arg Gln Ser Leu Pro Ser Leu Lys Asp Ser Cys Gln Arg Glu Leu<br>830                        835                        840                        845 | 2545 |
| aca aat ctt ctt ggc ctt cac ccc aaa att gaa atg gct cgt gca agc<br>Thr Asn Leu Leu Gly Leu His Pro Lys Ile Glu Met Ala Arg Ala Ser<br>                    850                        855                        860 | 2593 |
| tgc tcg gcc ctg atg tct cag cct tct gcc cca gat ttt gtc cag cgg<br>Cys Ser Ala Leu Met Ser Gln Pro Ser Ala Pro Asp Phe Val Gln Arg<br>865                        870                        875 | 2641 |
| ggc ttc gat agc ttt ctg ggc cgc tac caa gct gta caa gag gct gta<br>Gly Phe Asp Ser Phe Leu Gly Arg Tyr Gln Ala Val Gln Glu Ala Val<br>                    880                        885                        890 | 2689 |
| gag gat cgt caa caa cat cta gag aat gaa ctg aag ggc caa cct gga<br>Glu Asp Arg Gln Gln His Leu Glu Asn Glu Leu Lys Gly Gln Pro Gly<br>895                        900                        905 | 2737 |
| cat gca tat ctg gaa aca ttg aaa aca ctg aaa gat gtg cta aat gat<br>His Ala Tyr Leu Glu Thr Leu Lys Thr Leu Lys Asp Val Leu Asn Asp<br>910                        915                        920                        925 | 2785 |
| tca gaa aat aag gcc cag gtg tct ctg aat gtc ctt aat gat ctt gcc<br>Ser Glu Asn Lys Ala Gln Val Ser Leu Asn Val Leu Asn Asp Leu Ala<br>                    930                        935                        940 | 2833 |
| aag gtg gag aag gcc ctg caa gaa aaa aag acc ctt gat gaa atc ctt<br>Lys Val Glu Lys Ala Leu Gln Glu Lys Lys Thr Leu Asp Glu Ile Leu<br>945                        950                        955 | 2881 |
| gag aat cag aaa cct gca tta cat aaa ctt gca gaa gaa aca aag gct | 2929 |

-continued

```
Glu Asn Gln Lys Pro Ala Leu His Lys Leu Ala Glu Glu Thr Lys Ala
            960                 965                 970 ctg gag aaa aat gtt cat cct gat gta gaa aaa tta tat aag caa gaa      2977
Leu Glu Lys Asn Val His Pro Asp Val Glu Lys Leu Tyr Lys Gln Glu
975                 980                 985 ttt gat gat gtg caa gga aag tgg aac aag cta aag gtc ttg gtt tcc      3025
Phe Asp Asp Val Gln Gly Lys Trp Asn Lys Leu Lys Val Leu Val Ser
990                 995                 1000                1005 aaa gat cta cat ttg ctt gag gaa att gct ctc aca ctc aga gct ttt      3073
Lys Asp Leu His Leu Leu Glu Glu Ile Ala Leu Thr Leu Arg Ala Phe
            1010                1015                1020 gag gcc gat tca aca gtc att gag aag tgg atg gat ggc gtg aaa gac      3121
Glu Ala Asp Ser Thr Val Ile Glu Lys Trp Met Asp Gly Val Lys Asp
            1025                1030                1035 ttc tta atg aaa cag cag gct gcc caa gga gac gac gca ggt cta cag      3169
Phe Leu Met Lys Gln Gln Ala Ala Gln Gly Asp Asp Ala Gly Leu Gln
            1040                1045                1050 agg cag tta gac cag tgc tct gca ttt gtt aat gaa ata gaa aca att      3217
Arg Gln Leu Asp Gln Cys Ser Ala Phe Val Asn Glu Ile Glu Thr Ile
            1055                1060                1065 gaa tca tct ctg aaa aac atg aag gaa ata gag act aat ctt cga agt      3265
Glu Ser Ser Leu Lys Asn Met Lys Glu Ile Glu Thr Asn Leu Arg Ser
1070                1075                1080                1085 ggt cca gtt gct gga ata aaa act tgg gtg cag aca aga cta ggt gac      3313
Gly Pro Val Ala Gly Ile Lys Thr Trp Val Gln Thr Arg Leu Gly Asp
            1090                1095                1100 tac caa act caa ctg gag aaa ctt agc aag gag atc gct act caa aaa      3361
Tyr Gln Thr Gln Leu Glu Lys Leu Ser Lys Glu Ile Ala Thr Gln Lys
            1105                1110                1115 agt agg ttg tct gaa agt caa gaa aaa gct gcg aac ctg aag aaa gac      3409
Ser Arg Leu Ser Glu Ser Gln Glu Lys Ala Ala Asn Leu Lys Lys Asp
            1120                1125                1130 ttg gca gag atg cag gaa tgg atg acc cag gcc gag gaa gaa tat ttg      3457
Leu Ala Glu Met Gln Glu Trp Met Thr Gln Ala Glu Glu Glu Tyr Leu
            1135                1140                1145 gag cgg gat ttt gag tac aag tca cca gaa gag ctt gag agt gct gtg      3505
Glu Arg Asp Phe Glu Tyr Lys Ser Pro Glu Glu Leu Glu Ser Ala Val
1150                1155                1160                1165 gaa gag atg aag agg gca aaa gag gat gtg ttg cag aag gag gtg aga      3553
Glu Glu Met Lys Arg Ala Lys Glu Asp Val Leu Gln Lys Glu Val Arg
            1170                1175                1180 gtg aag att ctc aag gac aac atc aag tta tta gct gcc aag gtg ccc      3601
Val Lys Ile Leu Lys Asp Asn Ile Lys Leu Leu Ala Ala Lys Val Pro
            1185                1190                1195 tct ggt ggc cag gag ttg acg tct gag ctg aat gtt gtg ctg gag aat      3649
Ser Gly Gly Gln Glu Leu Thr Ser Glu Leu Asn Val Val Leu Glu Asn
            1200                1205                1210 tac caa ctt ctt tgt aat aga att cga gga aag tgc cac acg cta gag      3697
Tyr Gln Leu Leu Cys Asn Arg Ile Arg Gly Lys Cys His Thr Leu Glu
            1215                1220                1225 gag gtc tgg tct tgt tgg att gaa ctg ctt cac tat ttg gat ctt gaa      3745
Glu Val Trp Ser Cys Trp Ile Glu Leu Leu His Tyr Leu Asp Leu Glu
1230                1235                1240                1245 act acc tgg tta aac act ttg gaa gag cgg atg aag agc aca gag gtc      3793
Thr Thr Trp Leu Asn Thr Leu Glu Glu Arg Met Lys Ser Thr Glu Val
            1250                1255                1260 ctg cct gag aag acg gat gct gtc aac gaa gcc ctg gag tct ctg gaa      3841
Leu Pro Glu Lys Thr Asp Ala Val Asn Glu Ala Leu Glu Ser Leu Glu
            1265                1270                1275
```

```
tct gtt ctg cgc cac ccg gca gat aat cgc acc cag att cga gag ctt    3889
Ser Val Leu Arg His Pro Ala Asp Asn Arg Thr Gln Ile Arg Glu Leu
    1280                1285                1290 ggc cag act ctg att gat ggg ggg atc ctg gat gat ata atc agt gag    3937
Gly Gln Thr Leu Ile Asp Gly Gly Ile Leu Asp Asp Ile Ile Ser Glu
1295                1300                1305 aaa ctg gag gct ttc aac agc cga tat gaa gat cta agt cac ctg gca    3985
Lys Leu Glu Ala Phe Asn Ser Arg Tyr Glu Asp Leu Ser His Leu Ala
1310                1315                1320                1325 gag agc aag cag att tct ttg gaa aag caa ctc cag gtg ctg cgg gaa    4033
Glu Ser Lys Gln Ile Ser Leu Glu Lys Gln Leu Gln Val Leu Arg Glu
        1330                1335                1340 act gac cag atg ctt caa gtc ttg caa gag agc ttg ggg gag ctg gac    4081
Thr Asp Gln Met Leu Gln Val Leu Gln Glu Ser Leu Gly Glu Leu Asp
    1345                1350                1355 aaa cag ctc acc aca tac ctg act gac agg ata gat gct ttc caa gtt    4129
Lys Gln Leu Thr Thr Tyr Leu Thr Asp Arg Ile Asp Ala Phe Gln Val
1360                1365                1370 cca cag gaa gct cag aaa atc caa gca gag atc tca gcc cat gag cta    4177
Pro Gln Glu Ala Gln Lys Ile Gln Ala Glu Ile Ser Ala His Glu Leu
    1375                1380                1385 acc cta gag gag ttg aga aga aat atg cgt tct cag ccc ctg acc tcc    4225
Thr Leu Glu Glu Leu Arg Arg Asn Met Arg Ser Gln Pro Leu Thr Ser
1390                1395                1400                1405 cca gag agt agg act gcc aga gga gga agt cag atg gat gtg cta cag    4273
Pro Glu Ser Arg Thr Ala Arg Gly Gly Ser Gln Met Asp Val Leu Gln
        1410                1415                1420 agg aaa ctc cga gag gtg tcc aca aag ttc cag ctt ttc cag aag cca    4321
Arg Lys Leu Arg Glu Val Ser Thr Lys Phe Gln Leu Phe Gln Lys Pro
    1425                1430                1435 gct aac ttc gag cag cgc atg ctg gac tgc aag cgt gtg ctg gat ggc    4369
Ala Asn Phe Glu Gln Arg Met Leu Asp Cys Lys Arg Val Leu Asp Gly
1440                1445                1450 gtg aaa gca gaa ctt cac gtt ctg gat gtg aag gac gta gac cct gac    4417
Val Lys Ala Glu Leu His Val Leu Asp Val Lys Asp Val Asp Pro Asp
        1455                1460                1465 gtc ata cag acg cac ctg gac aag tgt atg aaa ctg tat aaa act ttg    4465
Val Ile Gln Thr His Leu Asp Lys Cys Met Lys Leu Tyr Lys Thr Leu
1470                1475                1480                1485 agt gaa gtc aaa ctt gaa gtg gaa act gtg att aaa aca gga aga cat    4513
Ser Glu Val Lys Leu Glu Val Glu Thr Val Ile Lys Thr Gly Arg His
        1490                1495                1500 att gtc cag aaa cag caa acg gac aac cca aaa ggg atg gat gag cag    4561
Ile Val Gln Lys Gln Gln Thr Asp Asn Pro Lys Gly Met Asp Glu Gln
    1505                1510                1515 ctg act tcc ctg aag gtt ctt tac aat gac ctg ggc gca cag gtg aca    4609
Leu Thr Ser Leu Lys Val Leu Tyr Asn Asp Leu Gly Ala Gln Val Thr
        1520                1525                1530 gaa gga aaa cag gat ctg gaa aga gca tca cag ttg gcc cgg aaa atg    4657
Glu Gly Lys Gln Asp Leu Glu Arg Ala Ser Gln Leu Ala Arg Lys Met
    1535                1540                1545 aag aaa gag gct gct tct ctc tct gaa tgg ctt tct gct act gaa act    4705
Lys Lys Glu Ala Ala Ser Leu Ser Glu Trp Leu Ser Ala Thr Glu Thr
1550                1555                1560                1565 gaa ttg gta cag aag tcc act tca gaa ggt ctg ctt ggt gac ttg gat    4753
Glu Leu Val Gln Lys Ser Thr Ser Glu Gly Leu Leu Gly Asp Leu Asp
        1570                1575                1580 aca gaa att tcc tgg gct aaa aat gtt ctg aag gat ctg gaa aag aga    4801
Thr Glu Ile Ser Trp Ala Lys Asn Val Leu Lys Asp Leu Glu Lys Arg
    1585                1590                1595
```

```
aaa gct gat tta aat acc atc aca gag agt agt gct gcc ctg caa aac      4849
Lys Ala Asp Leu Asn Thr Ile Thr Glu Ser Ser Ala Ala Leu Gln Asn
            1600                1605                1610 ttg att gag ggc agt gag cct att tta gaa gag agg ctc tgc gtc ctt      4897
Leu Ile Glu Gly Ser Glu Pro Ile Leu Glu Glu Arg Leu Cys Val Leu
    1615                1620                1625 aac gct ggg tgg agc cga gtt cgt acc tgg act gaa gat tgg tgc aat      4945
Asn Ala Gly Trp Ser Arg Val Arg Thr Trp Thr Glu Asp Trp Cys Asn
1630                1635                1640                1645 acc ttg atg aac cat cag aac cag cta gaa ata ttt gat ggg aac gtg      4993
Thr Leu Met Asn His Gln Asn Gln Leu Glu Ile Phe Asp Gly Asn Val
                1650                1655                1660 gct cac ata agt acc tgg ctt tat caa gct gaa gct cta ttg gat gaa      5041
Ala His Ile Ser Thr Trp Leu Tyr Gln Ala Glu Ala Leu Leu Asp Glu
        1665                1670                1675 att gaa aag aaa cca aca agt aaa cag gaa gaa att gtg aag cgt tta      5089
Ile Glu Lys Lys Pro Thr Ser Lys Gln Glu Glu Ile Val Lys Arg Leu
    1680                1685                1690 gta tct gag ctg gat gat gcc aac ctc cag gtt gaa aat gtc cgc gat      5137
Val Ser Glu Leu Asp Asp Ala Asn Leu Gln Val Glu Asn Val Arg Asp
1695                1700                1705 caa gcc ctt att ttg atg aat gcc cgt gga agc tca agc agg gag ctt      5185
Gln Ala Leu Ile Leu Met Asn Ala Arg Gly Ser Ser Ser Arg Glu Leu
1710                1715                1720                1725 gta gaa cca aag tta gct gag ctg aat agg aac ttt gaa aag gtg tct      5233
Val Glu Pro Lys Leu Ala Glu Leu Asn Arg Asn Phe Glu Lys Val Ser
                1730                1735                1740 caa cat atc aaa agt gcc aaa ttg cta att gct cag gaa cca tta tac      5281
Gln His Ile Lys Ser Ala Lys Leu Leu Ile Ala Gln Glu Pro Leu Tyr
        1745                1750                1755 caa tgt ttg gtc acc act gaa aca ttt gaa act ggt gtg cct ttc tct      5329
Gln Cys Leu Val Thr Thr Glu Thr Phe Glu Thr Gly Val Pro Phe Ser
    1760                1765                1770 gac ttg gaa aaa tta gaa aat gac ata gaa aat atg tta aaa ttt gtg      5377
Asp Leu Glu Lys Leu Glu Asn Asp Ile Glu Asn Met Leu Lys Phe Val
1775                1780                1785 gaa aaa cac ttg gaa tcc agt gat gaa gat gaa aag atg gat gag gag      5425
Glu Lys His Leu Glu Ser Ser Asp Glu Asp Glu Lys Met Asp Glu Glu
1790                1795                1800                1805 agt gcc cag att gag gaa gtt cta caa aga gga gaa gaa atg tta cat      5473
Ser Ala Gln Ile Glu Glu Val Leu Gln Arg Gly Glu Glu Met Leu His
        1810                1815                1820 caa cct atg gaa gat aat aaa aaa gaa aag atc cgt ttg caa tta tta      5521
Gln Pro Met Glu Asp Asn Lys Lys Glu Lys Ile Arg Leu Gln Leu Leu
    1825                1830                1835 ctt ttg cat act aga tac aac aaa att aag gca atc cct att caa cag      5569
Leu Leu His Thr Arg Tyr Asn Lys Ile Lys Ala Ile Pro Ile Gln Gln
1840                1845                1850 agg aaa atg ggt caa ctt gct tct gga att aga tca tca ctt ctt cct      5617
Arg Lys Met Gly Gln Leu Ala Ser Gly Ile Arg Ser Ser Leu Leu Pro
        1855                1860                1865 aca gat tat ctg gtt gaa att aac aaa att tta ctt tgc atg gat gat      5665
Thr Asp Tyr Leu Val Glu Ile Asn Lys Ile Leu Leu Cys Met Asp Asp
1870                1875                1880                1885 gtt gaa tta tcg ctt aat gtt cca gag ctc aac act gct att tac gaa      5713
Val Glu Leu Ser Leu Asn Val Pro Glu Leu Asn Thr Ala Ile Tyr Glu
        1890                1895                1900 gac ttc tct ttt cag gaa gac tct ctg aag aat atc aaa gac caa ctg      5761
Asp Phe Ser Phe Gln Glu Asp Ser Leu Lys Asn Ile Lys Asp Gln Leu
```

```
                        1905                    1910                    1915
gac aaa ctt gga gag cag att gca gtc att cat gaa aaa cag cca gat          5809
Asp Lys Leu Gly Glu Gln Ile Ala Val Ile His Glu Lys Gln Pro Asp
        1920                    1925                    1930 gtc atc ctt gaa gcc tct gga cct gaa gcc att cag atc aga gat aca          5857
Val Ile Leu Glu Ala Ser Gly Pro Glu Ala Ile Gln Ile Arg Asp Thr
    1935                    1940                    1945 ctt act cag ctg aat gca aaa tgg gac aga att aat aga atg tac agt          5905
Leu Thr Gln Leu Asn Ala Lys Trp Asp Arg Ile Asn Arg Met Tyr Ser
1950                    1955                    1960                    1965 gat cgg aaa ggt tgt ttt gac agg gca atg gaa gaa tgg aga cag ttc          5953
Asp Arg Lys Gly Cys Phe Asp Arg Ala Met Glu Glu Trp Arg Gln Phe
                1970                    1975                    1980 cat tgt gac ctt aat gac ctc aca cag tgg ata aca gag gct gaa gaa          6001
His Cys Asp Leu Asn Asp Leu Thr Gln Trp Ile Thr Glu Ala Glu Glu
            1985                    1990                    1995 tta ctg gtt gat acc tgt gct cca ggt ggc agc ctg gac tta gag aaa          6049
Leu Leu Val Asp Thr Cys Ala Pro Gly Gly Ser Leu Asp Leu Glu Lys
        2000                    2005                    2010 gcc agg ata cat cag cag gaa ctt gag gtg ggc atc agc agc cac cag          6097
Ala Arg Ile His Gln Gln Glu Leu Glu Val Gly Ile Ser Ser His Gln
2015                    2020                    2025 ccc agt ttt gca gca cta aac cga act ggg gat ggg att gtg cag aaa          6145
Pro Ser Phe Ala Ala Leu Asn Arg Thr Gly Asp Gly Ile Val Gln Lys
2030                    2035                    2040                    2045 ctc tcc cag gca gat gga agc ttc ttg aaa gaa aaa ctg gca ggt tta          6193
Leu Ser Gln Ala Asp Gly Ser Phe Leu Lys Glu Lys Leu Ala Gly Leu
                2050                    2055                    2060 aac caa cgc tgg gat gca att gtt gca gaa gtg aag gat agg cag cca          6241
Asn Gln Arg Trp Asp Ala Ile Val Ala Glu Val Lys Asp Arg Gln Pro
            2065                    2070                    2075 agg cta aaa gga gaa agt aag cag gtg atg aag tac agg cat cag cta          6289
Arg Leu Lys Gly Glu Ser Lys Gln Val Met Lys Tyr Arg His Gln Leu
        2080                    2085                    2090 gat gag att atc tgt tgg tta aca aag gct gag cat gct atg caa aag          6337
Asp Glu Ile Ile Cys Trp Leu Thr Lys Ala Glu His Ala Met Gln Lys
    2095                    2100                    2105 aga tca acc acc gaa ttg gga gaa aac ctg caa gaa tta aga gac tta          6385
Arg Ser Thr Thr Glu Leu Gly Glu Asn Leu Gln Glu Leu Arg Asp Leu
2110                    2115                    2120                    2125 act caa gaa atg gaa gta cat gct gaa aaa ctc aaa tgg ctg aat aga          6433
Thr Gln Glu Met Glu Val His Ala Glu Lys Leu Lys Trp Leu Asn Arg
                2130                    2135                    2140 act gaa ttg gag atg ctt tca gat aaa agt ctg agt tta cct gaa agg          6481
Thr Glu Leu Glu Met Leu Ser Asp Lys Ser Leu Ser Leu Pro Glu Arg
            2145                    2150                    2155 gat aaa att tca gaa agc tta agg act gta aat atg aca tgg aat aag          6529
Asp Lys Ile Ser Glu Ser Leu Arg Thr Val Asn Met Thr Trp Asn Lys
        2160                    2165                    2170 att tgc aga gag gtg cct acc acc ctg aag gaa tgc atc cag gag ccc          6577
Ile Cys Arg Glu Val Pro Thr Thr Leu Lys Glu Cys Ile Gln Glu Pro
    2175                    2180                    2185 agt tct gtt tca cag aca agg att gct gct cat cct aat gtc caa aag          6625
Ser Ser Val Ser Gln Thr Arg Ile Ala Ala His Pro Asn Val Gln Lys
2190                    2195                    2200                    2205 gtg gtg cta gta tca tct gcg tca gat att cct gtt cag tct cat cgt          6673
Val Val Leu Val Ser Ser Ala Ser Asp Ile Pro Val Gln Ser His Arg
                2210                    2215                    2220 act tcg gaa att tca att cct gct gat ctt gat aaa act ata aca gaa          6721
```

-continued

```
Thr Ser Glu Ile Ser Ile Pro Ala Asp Leu Asp Lys Thr Ile Thr Glu
        2225                2230                2235 cta gcc gac tgg ctg gta tta atc gac cag atg ctg aag tcc aac att    6769
Leu Ala Asp Trp Leu Val Leu Ile Asp Gln Met Leu Lys Ser Asn Ile
    2240                2245                2250 gtc act gtt ggg gat gta gaa gag atc aat aag acc gtt tcc cga atg    6817
Val Thr Val Gly Asp Val Glu Glu Ile Asn Lys Thr Val Ser Arg Met
    2255                2260                2265 aaa att aca aag gct gac tta gaa cag cgc cat cct cag ctg gat tat    6865
Lys Ile Thr Lys Ala Asp Leu Glu Gln Arg His Pro Gln Leu Asp Tyr
2270                2275                2280                2285 gtt ttt aca ttg gca cag aat ttg aaa aat aaa gct tcc agt tca gat    6913
Val Phe Thr Leu Ala Gln Asn Leu Lys Asn Lys Ala Ser Ser Ser Asp
        2290                2295                2300 atg aga aca gca att aca gaa aaa ttg gaa agg gtc aag aac cag tgg    6961
Met Arg Thr Ala Ile Thr Glu Lys Leu Glu Arg Val Lys Asn Gln Trp
    2305                2310                2315 gat ggc acc cag cat ggc gtt gag cta aga cag cag cag ctt gag gac    7009
Asp Gly Thr Gln His Gly Val Glu Leu Arg Gln Gln Gln Leu Glu Asp
    2320                2325                2330 atg att att gac agt ctt cag tgg gat gac cat agg gag gag act gaa    7057
Met Ile Ile Asp Ser Leu Gln Trp Asp Asp His Arg Glu Glu Thr Glu
2335                2340                2345 gaa ctg atg aga aaa tat gag gct cga ctc tat att ctt cag caa gcc    7105
Glu Leu Met Arg Lys Tyr Glu Ala Arg Leu Tyr Ile Leu Gln Gln Ala
2350                2355                2360                2365 cga cgg gat cca ctc acc aaa caa att tct gat aac caa ata ctg ctt    7153
Arg Arg Asp Pro Leu Thr Lys Gln Ile Ser Asp Asn Gln Ile Leu Leu
        2370                2375                2380 caa gaa ctg ggt cct gga gat ggt atc gtc atg gcg ttc gat aac gtc    7201
Gln Glu Leu Gly Pro Gly Asp Gly Ile Val Met Ala Phe Asp Asn Val
    2385                2390                2395 ctg cag aaa ctc ctg gag gaa tat ggg agt gat gac aca agg aat gtg    7249
Leu Gln Lys Leu Leu Glu Glu Tyr Gly Ser Asp Asp Thr Arg Asn Val
    2400                2405                2410 aaa gaa acc aca gag tac tta aaa aca tca tgg atc aat ctc aaa caa    7297
Lys Glu Thr Thr Glu Tyr Leu Lys Thr Ser Trp Ile Asn Leu Lys Gln
    2415                2420                2425 agt att gct gac aga cag aac gcc ttg gag gct gag tgg agg acg gtg    7345
Ser Ile Ala Asp Arg Gln Asn Ala Leu Glu Ala Glu Trp Arg Thr Val
    2430                2435                2440                2445 cag gcc tct cgc aga gat ctg gaa aac ttc ctg aag tgg atc caa gaa    7393
Gln Ala Ser Arg Arg Asp Leu Glu Asn Phe Leu Lys Trp Ile Gln Glu
        2450                2455                2460 gca gag acc aca gtg aat gtg ctt gtg gat gcc tct cat cgg gag aat    7441
Ala Glu Thr Thr Val Asn Val Leu Val Asp Ala Ser His Arg Glu Asn
        2465                2470                2475 gct ctt cag gat agt atc ttg gcc agg gaa ctc aaa cag cag atg cag    7489
Ala Leu Gln Asp Ser Ile Leu Ala Arg Glu Leu Lys Gln Gln Met Gln
    2480                2485                2490 gac atc cag gca gaa att gat gcc cac aat gac ata ttt aaa agc att    7537
Asp Ile Gln Ala Glu Ile Asp Ala His Asn Asp Ile Phe Lys Ser Ile
    2495                2500                2505 gac gga aac agg cag aag atg gta aaa gct ttg gga aat tct gaa gag    7585
Asp Gly Asn Arg Gln Lys Met Val Lys Ala Leu Gly Asn Ser Glu Glu
2510                2515                2520                2525 gct act atg ctt caa cat cga ctg gat gat atg aac caa aga tgg aat    7633
Ala Thr Met Leu Gln His Arg Leu Asp Asp Met Asn Gln Arg Trp Asn
        2530                2535                2540
```

```
gac tta aaa gca aaa tct gct agc atc agg gcc cat ttg gag gcc agc         7681
Asp Leu Lys Ala Lys Ser Ala Ser Ile Arg Ala His Leu Glu Ala Ser
            2545                2550                2555 gct gag aag tgg aac agg ttg ctg atg tcc tta gaa gaa ctg atc aaa         7729
Ala Glu Lys Trp Asn Arg Leu Leu Met Ser Leu Glu Glu Leu Ile Lys
        2560                2565                2570 tgg ctg aat atg aaa gat gaa gag ctt aag aaa caa atg cct att gga         7777
Trp Leu Asn Met Lys Asp Glu Glu Leu Lys Lys Gln Met Pro Ile Gly
    2575                2580                2585 gga gat gtt cca gcc tta cag ctc cag tat gac cat tgt aag gcc ctg         7825
Gly Asp Val Pro Ala Leu Gln Leu Gln Tyr Asp His Cys Lys Ala Leu
2590                2595                2600                2605 aga cgg gag tta aag gag aaa gaa tat tct gtc ctg aat gct gtc gac         7873
Arg Arg Glu Leu Lys Glu Lys Glu Tyr Ser Val Leu Asn Ala Val Asp
            2610                2615                2620 cag gcc cga gtt ttc ttg gct gat cag cca att gag gcc cct gaa gag         7921
Gln Ala Arg Val Phe Leu Ala Asp Gln Pro Ile Glu Ala Pro Glu Glu
        2625                2630                2635 cca aga aga aac cta caa tca aaa aca gaa tta act cct gag gag aga         7969
Pro Arg Arg Asn Leu Gln Ser Lys Thr Glu Leu Thr Pro Glu Glu Arg
    2640                2645                2650 gcc caa aag att gcc aaa gcc atg cgc aaa cag tct tct gaa gtc aaa         8017
Ala Gln Lys Ile Ala Lys Ala Met Arg Lys Gln Ser Ser Glu Val Lys
2655                2660                2665 gaa aaa tgg gaa agt cta aat gct gta act agc aat tgg caa aag caa         8065
Glu Lys Trp Glu Ser Leu Asn Ala Val Thr Ser Asn Trp Gln Lys Gln
2670                2675                2680                2685 gtg gac aag gca ttg gag aaa ctc aga gac ctg cag gga gct atg gat         8113
Val Asp Lys Ala Leu Glu Lys Leu Arg Asp Leu Gln Gly Ala Met Asp
            2690                2695                2700 gac ctg gac gct gac atg aag gag gca gag tcc gtg cgg aat ggc tgg         8161
Asp Leu Asp Ala Asp Met Lys Glu Ala Glu Ser Val Arg Asn Gly Trp
        2705                2710                2715 aag ccc gtg gga gac tta ctc att gac tcg ctg cag gat cac att gaa         8209
Lys Pro Val Gly Asp Leu Leu Ile Asp Ser Leu Gln Asp His Ile Glu
    2720                2725                2730 aaa atc atg gca ttt aga gaa gaa att gca cca atc aac ttt aaa gtt         8257
Lys Ile Met Ala Phe Arg Glu Glu Ile Ala Pro Ile Asn Phe Lys Val
2735                2740                2745 aaa acg gtg aat gat tta tcc agt cag ctg tct cca ctt gac ctg cat         8305
Lys Thr Val Asn Asp Leu Ser Ser Gln Leu Ser Pro Leu Asp Leu His
2750                2755                2760                2765 ccc tct cta aag atg tct cgc cag cta gat gac ctt aat atg cga tgg         8353
Pro Ser Leu Lys Met Ser Arg Gln Leu Asp Asp Leu Asn Met Arg Trp
            2770                2775                2780 aaa ctt tta cag gtt tct gtg gat gat cgc ctt aaa cag ctt cag gaa         8401
Lys Leu Leu Gln Val Ser Val Asp Asp Arg Leu Lys Gln Leu Gln Glu
        2785                2790                2795 gcc cac aga gat ttt gga cca tcc tct cag cat ttt ctc tct acg tca         8449
Ala His Arg Asp Phe Gly Pro Ser Ser Gln His Phe Leu Ser Thr Ser
    2800                2805                2810 gtc cag ctg ccg tgg caa aga tcc att tca cat aat aaa gtg ccc tat         8497
Val Gln Leu Pro Trp Gln Arg Ser Ile Ser His Asn Lys Val Pro Tyr
2815                2820                2825 tac atc aac cat caa aca cag acc acc tgt tgg gac cat cct aaa atg         8545
Tyr Ile Asn His Gln Thr Gln Thr Thr Cys Trp Asp His Pro Lys Met
2830                2835                2840                2845 acc gaa ctc ttt caa tcc ctt gct gac ctg aat aat gta cgt ttt tct         8593
Thr Glu Leu Phe Gln Ser Leu Ala Asp Leu Asn Asn Val Arg Phe Ser
            2850                2855                2860
```

```
gcc tac cgt aca gca atc aaa atc cga aga cta caa aaa gca cta tgt    8641
Ala Tyr Arg Thr Ala Ile Lys Ile Arg Arg Leu Gln Lys Ala Leu Cys
         2865                2870                2875 ttg gat ctc tta gag ttg agt aca aca aat gaa att ttc aaa cag cac    8689
Leu Asp Leu Leu Glu Leu Ser Thr Thr Asn Glu Ile Phe Lys Gln His
    2880                2885                2890 aag ttg aac caa aat gac cag ctc ctc agt gtt cca gat gtc atc aac    8737
Lys Leu Asn Gln Asn Asp Gln Leu Leu Ser Val Pro Asp Val Ile Asn
    2895                2900                2905 tgt ctg aca aca act tat gat gga ctt gag caa atg cat aag gac ctg    8785
Cys Leu Thr Thr Thr Tyr Asp Gly Leu Glu Gln Met His Lys Asp Leu
2910                2915                2920                2925 gtc aac gtt cca ctc tgt gtt gat atg tgt ctc aat tgg ttg ctc aat    8833
Val Asn Val Pro Leu Cys Val Asp Met Cys Leu Asn Trp Leu Leu Asn
         2930                2935                2940 gtc tat gac acg ggt cga act gga aaa att aga gtg cag agt ctg aag    8881
Val Tyr Asp Thr Gly Arg Thr Gly Lys Ile Arg Val Gln Ser Leu Lys
         2945                2950                2955 att gga tta atg tct ctc tcc aaa ggt ctc ttg gaa gaa aaa tac aga    8929
Ile Gly Leu Met Ser Leu Ser Lys Gly Leu Leu Glu Glu Lys Tyr Arg
         2960                2965                2970 tat ctc ttt aag gaa gtt gcg ggg ccg aca gaa atg tgt gac cag agg    8977
Tyr Leu Phe Lys Glu Val Ala Gly Pro Thr Glu Met Cys Asp Gln Arg
    2975                2980                2985 cag ctg ggc ctg tta ctt cat gat gcc atc cag atc ccc cgg cag cta    9025
Gln Leu Gly Leu Leu Leu His Asp Ala Ile Gln Ile Pro Arg Gln Leu
2990                2995                3000                3005 ggt gaa gta gca gct ttt gga ggc agt aat att gag cct agt gtt cgc    9073
Gly Glu Val Ala Ala Phe Gly Gly Ser Asn Ile Glu Pro Ser Val Arg
         3010                3015                3020 agc tgc ttc caa cag aat aac aat aaa cca gaa ata agt gtg aaa gag    9121
Ser Cys Phe Gln Gln Asn Asn Asn Lys Pro Glu Ile Ser Val Lys Glu
         3025                3030                3035 ttt ata gat tgg atg cat ttg gaa cca cag tcc atg gtt tgg ctc cca    9169
Phe Ile Asp Trp Met His Leu Glu Pro Gln Ser Met Val Trp Leu Pro
    3040                3045                3050 gtt tta cat cga gtg gca gca gcg gag act gca aaa cat cag gcc aaa    9217
Val Leu His Arg Val Ala Ala Ala Glu Thr Ala Lys His Gln Ala Lys
    3055                3060                3065 tgc aac atc tgt aaa gaa tgt cca att gtc ggg ttc agg tat aga agc    9265
Cys Asn Ile Cys Lys Glu Cys Pro Ile Val Gly Phe Arg Tyr Arg Ser
3070                3075                3080                3085 ctt aag cat ttt aac tat gat gtc tgc cag agt tgt ttc ttt tcg ggt    9313
Leu Lys His Phe Asn Tyr Asp Val Cys Gln Ser Cys Phe Phe Ser Gly
         3090                3095                3100 cga aca gca aaa ggt cac aaa tta cat tac cca atg gtg gaa tat tgt    9361
Arg Thr Ala Lys Gly His Lys Leu His Tyr Pro Met Val Glu Tyr Cys
         3105                3110                3115 ata cct aca aca tct ggg gaa gat gta cga gac ttc aca aag gta ctt    9409
Ile Pro Thr Thr Ser Gly Glu Asp Val Arg Asp Phe Thr Lys Val Leu
         3120                3125                3130 aag aac aag ttc agg tcg aag aag tac ttt gcc aaa cac cct cga ctt    9457
Lys Asn Lys Phe Arg Ser Lys Lys Tyr Phe Ala Lys His Pro Arg Leu
    3135                3140                3145 ggt tac ctg cct gtc cag aca gtt ctt gaa ggt gac aac tta gag act    9505
Gly Tyr Leu Pro Val Gln Thr Val Leu Glu Gly Asp Asn Leu Glu Thr
3150                3155                3160                3165 cct atc aca ctc atc agt atg tgg cca gag cac tat gac ccc tca caa    9553
Pro Ile Thr Leu Ile Ser Met Trp Pro Glu His Tyr Asp Pro Ser Gln
```

```
                3170              3175              3180
tct cct caa ctg ttt cat gat gac acc cat tca aga ata gaa caa tat      9601
Ser Pro Gln Leu Phe His Asp Asp Thr His Ser Arg Ile Glu Gln Tyr
        3185              3190              3195 gcc aca cga ctg gcc cag atg gaa agg act aat ggg tct ttt ctc act      9649
Ala Thr Arg Leu Ala Gln Met Glu Arg Thr Asn Gly Ser Phe Leu Thr
    3200              3205              3210 gat agc agc tcc acc aca gga agt gtg gaa gac gag cac gcc ctc atc      9697
Asp Ser Ser Ser Thr Thr Gly Ser Val Glu Asp Glu His Ala Leu Ile
    3215              3220              3225 cag cag tat tgc caa aca ctc gga gga gag tcc cca gtg agc cag ccg      9745
Gln Gln Tyr Cys Gln Thr Leu Gly Gly Glu Ser Pro Val Ser Gln Pro
3230              3235              3240              3245 cag agc cca gct cag atc ctg aag tca gta gag agg gaa gaa cgt gga      9793
Gln Ser Pro Ala Gln Ile Leu Lys Ser Val Glu Arg Glu Glu Arg Gly
        3250              3255              3260 gaa ctg gag agg atc att gct gac ctg gag gaa gaa caa aga aat cta      9841
Glu Leu Glu Arg Ile Ile Ala Asp Leu Glu Glu Glu Gln Arg Asn Leu
    3265              3270              3275 cag gtg gag tat gag cag ctg aag gac cag cac ctc cga agg ggg ctc      9889
Gln Val Glu Tyr Glu Gln Leu Lys Asp Gln His Leu Arg Arg Gly Leu
    3280              3285              3290 cct gtc ggt tca ccg cca gag tcg att ata tct ccc cat cac acg tct      9937
Pro Val Gly Ser Pro Pro Glu Ser Ile Ile Ser Pro His His Thr Ser
    3295              3300              3305 gag gat tca gaa ctt ata gca gaa gca aaa ctc ctc agg cag cac aaa      9985
Glu Asp Ser Glu Leu Ile Ala Glu Ala Lys Leu Leu Arg Gln His Lys
3310              3315              3320              3325 ggt cgg ctg gag gct agg atg cag att tta gaa gat cac aat aaa cag     10033
Gly Arg Leu Glu Ala Arg Met Gln Ile Leu Glu Asp His Asn Lys Gln
        3330              3335              3340 ctg gag tct cag ctc cac cgc ctc cga cag ctg ctg gag cag cct gaa     10081
Leu Glu Ser Gln Leu His Arg Leu Arg Gln Leu Leu Glu Gln Pro Glu
    3345              3350              3355 tct gat tcc cga atc aat ggt gtt tcc cca tgg gct tct cct cag cat     10129
Ser Asp Ser Arg Ile Asn Gly Val Ser Pro Trp Ala Ser Pro Gln His
    3360              3365              3370 tct gca ctg agc tac tcg ctt gat cca gat gcc tcc ggc cca cag ttc     10177
Ser Ala Leu Ser Tyr Ser Leu Asp Pro Asp Ala Ser Gly Pro Gln Phe
    3375              3380              3385 cac cag gca gcg gga gag gac ctg ctg gcc cca ccg cac gac acc agc     10225
His Gln Ala Ala Gly Glu Asp Leu Leu Ala Pro Pro His Asp Thr Ser
3390              3395              3400              3405 acg gat ctc acg gag gtc atg gag cag att cac agc acg ttt cca tct     10273
Thr Asp Leu Thr Glu Val Met Glu Gln Ile His Ser Thr Phe Pro Ser
        3410              3415              3420 tgc tgc cca aat gtt ccc agc agg cca cag gca atg taa tcactagt        10320
Cys Cys Pro Asn Val Pro Ser Arg Pro Gln Ala Met
            3425              3430

<210> SEQ ID NO 10
<211> LENGTH: 3433
<212> TYPE: PRT
<213> ORGANISM: Artificial Sequence
<220> FEATURE:
<221> NAME/KEY: misc_feature
<222> LOCATION: (239) ... (250)
<223> OTHER INFORMATION: Description of Artificial Sequence: Full length
      utrophin construct; Xaa = unknown

<400> SEQUENCE: 10
```

-continued

```
Met Ala Lys Tyr Gly Glu His Glu Ala Ser Pro Asp Asn Gly Gln Asn
 1               5                  10                  15

Glu Phe Ser Asp Ile Ile Glu Ser Arg Ser Asp Glu His Asn Asp Val
             20                  25                  30

Gln Lys Lys Thr Phe Thr Lys Trp Ile Asn Ala Arg Phe Ser Lys Ser
         35                  40                  45

Gly Lys Pro Pro Ile Ser Asp Met Phe Ser Asp Leu Lys Asp Gly Arg
     50                  55                  60

Lys Leu Leu Asp Leu Leu Glu Gly Leu Thr Gly Thr Ser Leu Pro Lys
 65                  70                  75                  80

Glu Arg Gly Ser Thr Arg Val His Ala Leu Asn Asn Val Asn Arg Val
                 85                  90                  95

Leu Gln Val Leu His Gln Asn Asn Val Asp Leu Val Asn Ile Gly Gly
            100                 105                 110

Thr Asp Ile Val Asp Gly Asn Pro Lys Leu Thr Leu Gly Leu Leu Trp
        115                 120                 125

Ser Ile Ile Leu His Trp Gln Val Lys Asp Val Met Lys Asp Ile Met
130                 135                 140

Ser Asp Leu Gln Gln Thr Asn Ser Glu Lys Ile Leu Leu Ser Trp Val
145                 150                 155                 160

Arg Gln Thr Thr Arg Pro Tyr Ser Gln Val Asn Val Leu Asn Phe Thr
                165                 170                 175

Thr Ser Trp Thr Asp Gly Leu Ala Phe Asn Ala Val Leu His Arg His
            180                 185                 190

Lys Pro Asp Leu Phe Ser Trp Asp Arg Val Val Lys Met Ser Pro Ile
        195                 200                 205

Glu Arg Leu Glu His Ala Phe Ser Lys Ala His Thr Tyr Leu Gly Ile
    210                 215                 220

Glu Lys Leu Leu Asp Pro Glu Asp Val Ala Val His Leu Pro Xaa Xaa
225                 230                 235                 240

Xaa Xaa Xaa Xaa Xaa Xaa Xaa Xaa Xaa Val Glu Val Leu Pro Gln
                245                 250                 255

Gln Val Thr Ile Asp Ala Ile Arg Glu Val Glu Thr Leu Pro Arg Lys
                260                 265                 270

Tyr Lys Lys Glu Cys Glu Glu Glu Ile His Ile Gln Ser Ala Val
            275                 280                 285

Leu Ala Glu Glu Gly Gln Ser Pro Arg Ala Glu Thr Pro Ser Thr Val
    290                 295                 300

Thr Glu Val Asp Met Asp Leu Asp Ser Tyr Gln Ile Ala Leu Glu Glu
305                 310                 315                 320

Val Leu Thr Trp Leu Leu Ser Ala Glu Asp Thr Phe Gln Glu Gln Asp
                325                 330                 335

Asp Ile Ser Asp Asp Val Glu Glu Val Lys Glu Gln Phe Ala Thr His
            340                 345                 350

Glu Thr Phe Met Met Glu Leu Thr Ala His Gln Ser Ser Val Gly Ser
        355                 360                 365

Val Leu Gln Ala Gly Asn Gln Leu Met Thr Gln Gly Thr Leu Ser Glu
    370                 375                 380

Glu Glu Glu Phe Glu Ile Gln Glu Gln Met Thr Leu Leu Asn Ala Arg
385                 390                 395                 400

Trp Glu Ala Leu Arg Val Glu Ser Met Glu Arg Gln Ser Arg Leu His
                405                 410                 415

Asp Ala Leu Met Glu Leu Gln Lys Lys Gln Leu Gln Gln Leu Ser Ser
```

-continued

```
                420                 425                 430
Trp Leu Ala Leu Thr Glu Glu Arg Ile Gln Lys Met Glu Ser Pro Pro
            435                 440                 445
Leu Gly Asp Asp Leu Pro Ser Leu Gln Lys Leu Leu Gln Glu His Lys
    450                 455                 460
Ser Leu Gln Asn Asp Leu Glu Ala Glu Gln Val Lys Val Asn Ser Leu
465                 470                 475                 480
Thr His Met Val Val Ile Val Asp Glu Asn Ser Gly Glu Ser Ala Thr
                485                 490                 495
Ala Leu Leu Glu Asp Gln Leu Gln Lys Leu Gly Glu Arg Trp Thr Ala
            500                 505                 510
Val Cys Arg Trp Thr Glu Glu Arg Trp Asn Arg Leu Gln Glu Ile Ser
        515                 520                 525
Ile Leu Trp Gln Glu Leu Leu Glu Glu Gln Cys Leu Leu Glu Ala Trp
    530                 535                 540
Leu Thr Glu Lys Glu Glu Ala Leu Asn Lys Val Gln Thr Ser Asn Phe
545                 550                 555                 560
Lys Asp Gln Lys Glu Leu Ser Val Ser Val Arg Arg Leu Ala Ile Leu
                565                 570                 575
Lys Glu Asp Met Glu Met Lys Arg Gln Thr Leu Asp Gln Leu Ser Glu
            580                 585                 590
Ile Gly Gln Asp Val Gly Gln Leu Leu Ser Asn Pro Lys Ala Ser Lys
        595                 600                 605
Lys Met Asn Ser Asp Ser Glu Glu Leu Thr Gln Arg Trp Asp Ser Leu
    610                 615                 620
Val Gln Arg Leu Glu Asp Ser Ser Asn Gln Val Thr Gln Ala Val Ala
625                 630                 635                 640
Lys Leu Gly Met Ser Gln Ile Pro Gln Lys Asp Leu Leu Glu Thr Val
                645                 650                 655
His Val Arg Glu Lys Gly Met Val Lys Lys Pro Lys Gln Glu Leu Pro
            660                 665                 670
Pro Pro Leu Gly Pro Lys Lys Arg Gln Ile His Val Asp Ile Glu Ala
        675                 680                 685
Lys Lys Lys Phe Asp Ala Ile Ser Ala Glu Leu Leu Asn Trp Ile Leu
    690                 695                 700
Lys Trp Lys Thr Ala Ile Gln Thr Thr Glu Ile Lys Glu Tyr Met Lys
705                 710                 715                 720
Met Gln Asp Thr Ser Glu Met Lys Lys Leu Lys Ala Leu Glu Lys
                725                 730                 735
Glu Gln Arg Glu Arg Ile Pro Arg Ala Asp Glu Leu Asn Gln Thr Gly
            740                 745                 750
Gln Ile Leu Val Glu Gln Met Gly Lys Glu Gly Leu Pro Thr Glu Glu
        755                 760                 765
Ile Lys Asn Val Leu Glu Lys Val Ser Ser Glu Trp Lys Asn Val Ser
    770                 775                 780
Gln His Leu Glu Asp Leu Glu Arg Lys Ile Gln Leu Gln Glu Asp Ile
785                 790                 795                 800
Asn Ala Tyr Phe Lys Gln Leu Asp Glu Leu Glu Lys Val Ile Lys Thr
                805                 810                 815
Lys Glu Glu Trp Val Lys His Thr Ser Ile Ser Glu Ser Arg Gln
            820                 825                 830
Ser Leu Pro Ser Leu Lys Asp Ser Cys Gln Arg Glu Leu Thr Asn Leu
    835                 840                 845
```

-continued

```
Leu Gly Leu His Pro Lys Ile Glu Met Ala Arg Ala Ser Cys Ser Ala
        850                 855                 860
Leu Met Ser Gln Pro Ser Ala Pro Asp Phe Val Gln Arg Gly Phe Asp
865                 870                 875                 880
Ser Phe Leu Gly Arg Tyr Gln Ala Val Gln Glu Ala Val Glu Asp Arg
                885                 890                 895
Gln Gln His Leu Glu Asn Glu Leu Lys Gly Gln Pro Gly His Ala Tyr
            900                 905                 910
Leu Glu Thr Leu Lys Thr Leu Lys Asp Val Leu Asn Asp Ser Glu Asn
        915                 920                 925
Lys Ala Gln Val Ser Leu Asn Val Leu Asn Asp Leu Ala Lys Val Glu
    930                 935                 940
Lys Ala Leu Gln Glu Lys Lys Thr Leu Asp Glu Ile Leu Glu Asn Gln
945                 950                 955                 960
Lys Pro Ala Leu His Lys Leu Ala Glu Glu Thr Lys Ala Leu Glu Lys
                965                 970                 975
Asn Val His Pro Asp Val Glu Lys Leu Tyr Lys Gln Glu Phe Asp Asp
            980                 985                 990
Val Gln Gly Lys Trp Asn Lys Leu Lys Val Leu Val Ser Lys Asp Leu
        995                 1000                1005
His Leu Leu Glu Glu Ile Ala Leu Thr Leu Arg Ala Phe Glu Ala Asp
    1010                1015                1020
Ser Thr Val Ile Glu Lys Trp Met Asp Gly Val Lys Asp Phe Leu Met
1025                1030                1035                1040
Lys Gln Gln Ala Ala Gln Gly Asp Asp Ala Gly Leu Gln Arg Gln Leu
                1045                1050                1055
Asp Gln Cys Ser Ala Phe Val Asn Glu Ile Glu Thr Ile Glu Ser Ser
            1060                1065                1070
Leu Lys Asn Met Lys Glu Ile Glu Thr Asn Leu Arg Ser Gly Pro Val
        1075                1080                1085
Ala Gly Ile Lys Thr Trp Val Gln Thr Arg Leu Gly Asp Tyr Gln Thr
    1090                1095                1100
Gln Leu Glu Lys Leu Ser Lys Glu Ile Ala Thr Gln Lys Ser Arg Leu
1105                1110                1115                1120
Ser Glu Ser Gln Glu Lys Ala Ala Asn Leu Lys Lys Asp Leu Ala Glu
                1125                1130                1135
Met Gln Glu Trp Met Thr Gln Ala Glu Glu Tyr Leu Glu Arg Asp
            1140                1145                1150
Phe Glu Tyr Lys Ser Pro Glu Glu Leu Glu Ser Ala Val Glu Glu Met
        1155                1160                1165
Lys Arg Ala Lys Glu Asp Val Leu Gln Lys Glu Val Arg Val Lys Ile
    1170                1175                1180
Leu Lys Asp Asn Ile Lys Leu Leu Ala Ala Lys Val Pro Ser Gly Gly
1185                1190                1195                1200
Gln Glu Leu Thr Ser Glu Leu Asn Val Val Leu Glu Asn Tyr Gln Leu
                1205                1210                1215
Leu Cys Asn Arg Ile Arg Gly Lys Cys His Thr Leu Glu Glu Val Trp
            1220                1225                1230
Ser Cys Trp Ile Glu Leu Leu His Tyr Leu Asp Leu Glu Thr Thr Trp
        1235                1240                1245
Leu Asn Thr Leu Glu Glu Arg Met Lys Ser Thr Glu Val Leu Pro Glu
    1250                1255                1260
```

-continued

```
Lys Thr Asp Ala Val Asn Glu Ala Leu Glu Ser Leu Glu Ser Val Leu
1265                1270                1275                1280

Arg His Pro Ala Asp Asn Arg Thr Gln Ile Arg Glu Leu Gly Gln Thr
                1285                1290                1295

Leu Ile Asp Gly Gly Ile Leu Asp Asp Ile Ile Ser Glu Lys Leu Glu
            1300                1305                1310

Ala Phe Asn Ser Arg Tyr Glu Asp Leu Ser His Leu Ala Glu Ser Lys
    1315                1320                1325

Gln Ile Ser Leu Glu Lys Gln Leu Gln Val Leu Arg Glu Thr Asp Gln
1330                1335                1340

Met Leu Gln Val Leu Gln Glu Ser Leu Gly Glu Leu Asp Lys Gln Leu
1345                1350                1355                1360

Thr Thr Tyr Leu Thr Asp Arg Ile Asp Ala Phe Gln Val Pro Gln Glu
            1365                1370                1375

Ala Gln Lys Ile Gln Ala Glu Ile Ser Ala His Glu Leu Thr Leu Glu
        1380                1385                1390

Glu Leu Arg Arg Asn Met Arg Ser Gln Pro Leu Thr Ser Pro Glu Ser
        1395                1400                1405

Arg Thr Ala Arg Gly Gly Ser Gln Met Asp Val Leu Gln Arg Lys Leu
    1410                1415                1420

Arg Glu Val Ser Thr Lys Phe Gln Leu Phe Gln Lys Pro Ala Asn Phe
1425                1430                1435                1440

Glu Gln Arg Met Leu Asp Cys Lys Arg Val Leu Asp Gly Val Lys Ala
                1445                1450                1455

Glu Leu His Val Leu Asp Val Lys Asp Val Asp Pro Asp Val Ile Gln
            1460                1465                1470

Thr His Leu Asp Lys Cys Met Lys Leu Tyr Lys Thr Leu Ser Glu Val
        1475                1480                1485

Lys Leu Glu Val Glu Thr Val Ile Lys Thr Gly Arg His Ile Val Gln
1490                1495                1500

Lys Gln Gln Thr Asp Asn Pro Lys Gly Met Asp Glu Gln Leu Thr Ser
1505                1510                1515                1520

Leu Lys Val Leu Tyr Asn Asp Leu Gly Ala Gln Val Thr Glu Gly Lys
            1525                1530                1535

Gln Asp Leu Glu Arg Ala Ser Gln Leu Ala Arg Lys Met Lys Lys Glu
        1540                1545                1550

Ala Ala Ser Leu Ser Glu Trp Leu Ser Ala Thr Glu Thr Glu Leu Val
    1555                1560                1565

Gln Lys Ser Thr Ser Glu Gly Leu Leu Gly Asp Leu Asp Thr Glu Ile
1570                1575                1580

Ser Trp Ala Lys Asn Val Leu Lys Asp Leu Glu Lys Arg Lys Ala Asp
1585                1590                1595                1600

Leu Asn Thr Ile Thr Glu Ser Ser Ala Ala Leu Gln Asn Leu Ile Glu
            1605                1610                1615

Gly Ser Glu Pro Ile Leu Glu Glu Arg Leu Cys Val Leu Asn Ala Gly
        1620                1625                1630

Trp Ser Arg Val Arg Thr Trp Thr Glu Asp Trp Cys Asn Thr Leu Met
    1635                1640                1645

Asn His Gln Asn Gln Leu Glu Ile Phe Asp Gly Asn Val Ala His Ile
1650                1655                1660

Ser Thr Trp Leu Tyr Gln Ala Glu Ala Leu Leu Asp Glu Ile Glu Lys
1665                1670                1675                1680

Lys Pro Thr Ser Lys Gln Glu Glu Ile Val Lys Arg Leu Val Ser Glu
```

```
                    1685                  1690                       1695
Leu Asp Asp Ala Asn Leu Gln Val Glu Asn Val Arg Asp Gln Ala Leu
                1700                1705                1710
Ile Leu Met Asn Ala Arg Gly Ser Ser Arg Glu Leu Val Glu Pro
        1715                1720                1725
Lys Leu Ala Glu Leu Asn Arg Asn Phe Glu Lys Val Ser Gln His Ile
        1730                1735                1740
Lys Ser Ala Lys Leu Leu Ile Ala Gln Glu Pro Leu Tyr Gln Cys Leu
1745                1750                1755                1760
Val Thr Thr Glu Thr Phe Glu Thr Gly Val Pro Phe Ser Asp Leu Glu
                1765                1770                1775
Lys Leu Glu Asn Asp Ile Glu Asn Met Leu Lys Phe Val Glu Lys His
                1780                1785                1790
Leu Glu Ser Ser Asp Glu Asp Glu Lys Met Asp Glu Glu Ser Ala Gln
                1795                1800                1805
Ile Glu Glu Val Leu Gln Arg Gly Glu Glu Met Leu His Gln Pro Met
            1810                1815                1820
Glu Asp Asn Lys Lys Glu Lys Ile Arg Leu Gln Leu Leu Leu Leu His
1825                1830                1835                1840
Thr Arg Tyr Asn Lys Ile Lys Ala Ile Pro Ile Gln Gln Arg Lys Met
                1845                1850                1855
Gly Gln Leu Ala Ser Gly Ile Arg Ser Ser Leu Leu Pro Thr Asp Tyr
            1860                1865                1870
Leu Val Glu Ile Asn Lys Ile Leu Leu Cys Met Asp Asp Val Glu Leu
            1875                1880                1885
Ser Leu Asn Val Pro Glu Leu Asn Thr Ala Ile Tyr Glu Asp Phe Ser
        1890                1895                1900
Phe Gln Glu Asp Ser Leu Lys Asn Ile Lys Asp Gln Leu Asp Lys Leu
1905                1910                1915                1920
Gly Glu Gln Ile Ala Val Ile His Glu Lys Gln Pro Asp Val Ile Leu
                1925                1930                1935
Glu Ala Ser Gly Pro Glu Ala Ile Gln Ile Arg Asp Thr Leu Thr Gln
            1940                1945                1950
Leu Asn Ala Lys Trp Asp Arg Ile Asn Arg Met Tyr Ser Asp Arg Lys
        1955                1960                1965
Gly Cys Phe Asp Arg Ala Met Glu Glu Trp Arg Gln Phe His Cys Asp
    1970                1975                1980
Leu Asn Asp Leu Thr Gln Trp Ile Thr Glu Ala Glu Glu Leu Leu Val
1985                1990                1995                2000
Asp Thr Cys Ala Pro Gly Gly Ser Leu Asp Leu Glu Lys Ala Arg Ile
                2005                2010                2015
His Gln Gln Glu Leu Glu Val Gly Ile Ser Ser His Gln Pro Ser Phe
            2020                2025                2030
Ala Ala Leu Asn Arg Thr Gly Asp Gly Ile Val Gln Lys Leu Ser Gln
        2035                2040                2045
Ala Asp Gly Ser Phe Leu Lys Glu Lys Leu Ala Gly Leu Asn Gln Arg
    2050                2055                2060
Trp Asp Ala Ile Val Ala Glu Val Lys Asp Arg Gln Pro Arg Leu Lys
2065                2070                2075                2080
Gly Glu Ser Lys Gln Val Met Lys Tyr Arg His Gln Leu Asp Glu Ile
            2085                2090                2095
Ile Cys Trp Leu Thr Lys Ala Glu His Ala Met Gln Lys Arg Ser Thr
        2100                2105                2110
```

-continued

```
Thr Glu Leu Gly Glu Asn Leu Gln Glu Leu Arg Asp Leu Thr Gln Glu
    2115                2120                2125
Met Glu Val His Ala Glu Lys Leu Lys Trp Leu Asn Arg Thr Glu Leu
    2130                2135                2140
Glu Met Leu Ser Asp Lys Ser Leu Ser Leu Pro Glu Arg Asp Lys Ile
2145                2150                2155                2160
Ser Glu Ser Leu Arg Thr Val Asn Met Thr Trp Asn Lys Ile Cys Arg
            2165                2170                2175
Glu Val Pro Thr Thr Leu Lys Glu Cys Ile Gln Glu Pro Ser Ser Val
                2180                2185                2190
Ser Gln Thr Arg Ile Ala Ala His Pro Asn Val Gln Lys Val Val Leu
        2195                2200                2205
Val Ser Ser Ala Ser Asp Ile Pro Val Gln Ser His Arg Thr Ser Glu
    2210                2215                2220
Ile Ser Ile Pro Ala Asp Leu Asp Lys Thr Ile Thr Glu Leu Ala Asp
2225                2230                2235                2240
Trp Leu Val Leu Ile Asp Gln Met Leu Lys Ser Asn Ile Val Thr Val
            2245                2250                2255
Gly Asp Val Glu Glu Ile Asn Lys Thr Val Ser Arg Met Lys Ile Thr
                2260                2265                2270
Lys Ala Asp Leu Glu Gln Arg His Pro Gln Leu Asp Tyr Val Phe Thr
        2275                2280                2285
Leu Ala Gln Asn Leu Lys Asn Lys Ala Ser Ser Asp Met Arg Thr
    2290                2295                2300
Ala Ile Thr Glu Lys Leu Glu Arg Val Lys Asn Gln Trp Asp Gly Thr
2305                2310                2315                2320
Gln His Gly Val Glu Leu Arg Gln Gln Gln Leu Glu Asp Met Ile Ile
            2325                2330                2335
Asp Ser Leu Gln Trp Asp Asp His Arg Glu Glu Thr Glu Glu Leu Met
                2340                2345                2350
Arg Lys Tyr Glu Ala Arg Leu Tyr Ile Leu Gln Gln Ala Arg Arg Asp
        2355                2360                2365
Pro Leu Thr Lys Gln Ile Ser Asp Asn Gln Ile Leu Leu Gln Glu Leu
    2370                2375                2380
Gly Pro Gly Asp Gly Ile Val Met Ala Phe Asp Asn Val Leu Gln Lys
2385                2390                2395                2400
Leu Leu Glu Glu Tyr Gly Ser Asp Asp Thr Arg Asn Val Lys Glu Thr
            2405                2410                2415
Thr Glu Tyr Leu Lys Thr Ser Trp Ile Asn Leu Lys Gln Ser Ile Ala
                2420                2425                2430
Asp Arg Gln Asn Ala Leu Glu Ala Glu Trp Arg Thr Val Gln Ala Ser
        2435                2440                2445
Arg Arg Asp Leu Glu Asn Phe Leu Lys Trp Ile Gln Glu Ala Glu Thr
    2450                2455                2460
Thr Val Asn Val Leu Val Asp Ala Ser His Arg Glu Asn Ala Leu Gln
2465                2470                2475                2480
Asp Ser Ile Leu Ala Arg Glu Leu Lys Gln Gln Met Gln Asp Ile Gln
            2485                2490                2495
Ala Glu Ile Asp Ala His Asn Asp Ile Phe Lys Ser Ile Asp Gly Asn
                2500                2505                2510
Arg Gln Lys Met Val Lys Ala Leu Gly Asn Ser Glu Glu Ala Thr Met
        2515                2520                2525
```

-continued

```
Leu Gln His Arg Leu Asp Asp Met Asn Gln Arg Trp Asn Asp Leu Lys
    2530                2535                2540
Ala Lys Ser Ala Ser Ile Arg Ala His Leu Glu Ala Ser Ala Glu Lys
2545                2550                2555                2560
Trp Asn Arg Leu Leu Met Ser Leu Glu Glu Leu Ile Lys Trp Leu Asn
                2565                2570                2575
Met Lys Asp Glu Glu Leu Lys Lys Gln Met Pro Ile Gly Gly Asp Val
            2580                2585                2590
Pro Ala Leu Gln Leu Gln Tyr Asp His Cys Lys Ala Leu Arg Arg Glu
        2595                2600                2605
Leu Lys Glu Lys Glu Tyr Ser Val Leu Asn Ala Val Asp Gln Ala Arg
    2610                2615                2620
Val Phe Leu Ala Asp Gln Pro Ile Glu Ala Pro Glu Glu Pro Arg Arg
2625                2630                2635                2640
Asn Leu Gln Ser Lys Thr Glu Leu Thr Pro Glu Glu Arg Ala Gln Lys
                2645                2650                2655
Ile Ala Lys Ala Met Arg Lys Gln Ser Ser Glu Val Lys Glu Lys Trp
            2660                2665                2670
Glu Ser Leu Asn Ala Val Thr Ser Asn Trp Gln Lys Gln Val Asp Lys
        2675                2680                2685
Ala Leu Glu Lys Leu Arg Asp Leu Gln Gly Ala Met Asp Asp Leu Asp
    2690                2695                2700
Ala Asp Met Lys Glu Ala Glu Ser Val Arg Asn Gly Trp Lys Pro Val
2705                2710                2715                2720
Gly Asp Leu Leu Ile Asp Ser Leu Gln Asp His Ile Glu Lys Ile Met
                2725                2730                2735
Ala Phe Arg Glu Glu Ile Ala Pro Ile Asn Phe Lys Val Lys Thr Val
            2740                2745                2750
Asn Asp Leu Ser Ser Gln Leu Ser Pro Leu Asp Leu His Pro Ser Leu
        2755                2760                2765
Lys Met Ser Arg Gln Leu Asp Asp Leu Asn Met Arg Trp Lys Leu Leu
    2770                2775                2780
Gln Val Ser Val Asp Asp Arg Leu Lys Gln Leu Gln Glu Ala His Arg
2785                2790                2795                2800
Asp Phe Gly Pro Ser Ser Gln His Phe Leu Ser Thr Ser Val Gln Leu
            2805                2810                2815
Pro Trp Gln Arg Ser Ile Ser His Asn Lys Val Pro Tyr Tyr Ile Asn
        2820                2825                2830
His Gln Thr Gln Thr Thr Cys Trp Asp His Pro Lys Met Thr Glu Leu
    2835                2840                2845
Phe Gln Ser Leu Ala Asp Leu Asn Asn Val Arg Phe Ser Ala Tyr Arg
    2850                2855                2860
Thr Ala Ile Lys Ile Arg Arg Leu Gln Lys Ala Leu Cys Leu Asp Leu
2865                2870                2875                2880
Leu Glu Leu Ser Thr Thr Asn Glu Ile Phe Lys Gln His Lys Leu Asn
                2885                2890                2895
Gln Asn Asp Gln Leu Leu Ser Val Pro Asp Val Ile Asn Cys Leu Thr
            2900                2905                2910
Thr Thr Tyr Asp Gly Leu Glu Gln Met His Lys Asp Leu Val Asn Val
            2915                2920                2925
Pro Leu Cys Val Asp Met Cys Leu Asn Trp Leu Leu Asn Val Tyr Asp
        2930                2935                2940
Thr Gly Arg Thr Gly Lys Ile Arg Val Gln Ser Leu Lys Ile Gly Leu
```

-continued

```
2945              2950              2955              2960

Met Ser Leu Ser Lys Gly Leu Leu Glu Glu Lys Tyr Arg Tyr Leu Phe
            2965              2970              2975

Lys Glu Val Ala Gly Pro Thr Glu Met Cys Asp Gln Arg Gln Leu Gly
            2980              2985              2990

Leu Leu Leu His Asp Ala Ile Gln Ile Pro Arg Gln Leu Gly Glu Val
            2995              3000              3005

Ala Ala Phe Gly Gly Ser Asn Ile Glu Pro Ser Val Arg Ser Cys Phe
            3010              3015              3020

Gln Gln Asn Asn Asn Lys Pro Glu Ile Ser Val Lys Glu Phe Ile Asp
3025              3030              3035              3040

Trp Met His Leu Glu Pro Gln Ser Met Val Trp Leu Pro Val Leu His
            3045              3050              3055

Arg Val Ala Ala Ala Glu Thr Ala Lys His Gln Ala Lys Cys Asn Ile
            3060              3065              3070

Cys Lys Glu Cys Pro Ile Val Gly Phe Arg Tyr Arg Ser Leu Lys His
            3075              3080              3085

Phe Asn Tyr Asp Val Cys Gln Ser Cys Phe Phe Ser Gly Arg Thr Ala
            3090              3095              3100

Lys Gly His Lys Leu His Tyr Pro Met Val Glu Tyr Cys Ile Pro Thr
3105              3110              3115              3120

Thr Ser Gly Glu Asp Val Arg Asp Phe Thr Lys Val Leu Lys Asn Lys
            3125              3130              3135

Phe Arg Ser Lys Lys Tyr Phe Ala Lys His Pro Arg Leu Gly Tyr Leu
            3140              3145              3150

Pro Val Gln Thr Val Leu Glu Gly Asp Asn Leu Glu Thr Pro Ile Thr
            3155              3160              3165

Leu Ile Ser Met Trp Pro Glu His Tyr Asp Pro Ser Gln Ser Pro Gln
            3170              3175              3180

Leu Phe His Asp Asp Thr His Ser Arg Ile Glu Gln Tyr Ala Thr Arg
3185              3190              3195              3200

Leu Ala Gln Met Glu Arg Thr Asn Gly Ser Phe Leu Thr Asp Ser Ser
            3205              3210              3215

Ser Thr Thr Gly Ser Val Glu Asp Glu His Ala Leu Ile Gln Gln Tyr
            3220              3225              3230

Cys Gln Thr Leu Gly Gly Glu Ser Pro Val Ser Gln Pro Gln Ser Pro
            3235              3240              3245

Ala Gln Ile Leu Lys Ser Val Glu Arg Glu Arg Gly Glu Leu Glu
            3250              3255              3260

Arg Ile Ile Ala Asp Leu Glu Glu Glu Gln Arg Asn Leu Gln Val Glu
3265              3270              3275              3280

Tyr Glu Gln Leu Lys Asp Gln His Leu Arg Arg Gly Leu Pro Val Gly
            3285              3290              3295

Ser Pro Pro Glu Ser Ile Ile Ser Pro His His Thr Ser Glu Asp Ser
            3300              3305              3310

Glu Leu Ile Ala Glu Ala Lys Leu Leu Arg Gln His Lys Gly Arg Leu
            3315              3320              3325

Glu Ala Arg Met Gln Ile Leu Glu Asp His Asn Lys Gln Leu Glu Ser
            3330              3335              3340

Gln Leu His Arg Leu Arg Gln Leu Leu Glu Gln Pro Glu Ser Asp Ser
3345              3350              3355              3360

Arg Ile Asn Gly Val Ser Pro Trp Ala Ser Pro Gln His Ser Ala Leu
            3365              3370              3375
```

```
Ser Tyr Ser Leu Asp Pro Asp Ala Ser Gly Pro Gln Phe His Gln Ala
            3380            3385                3390

Ala Gly Glu Asp Leu Leu Ala Pro Pro His Asp Thr Ser Thr Asp Leu
        3395                3400                3405

Thr Glu Val Met Glu Gln Ile His Ser Thr Phe Pro Ser Cys Cys Pro
    3410                3415                3420

Asn Val Pro Ser Arg Pro Gln Ala Met
3425                3430

<210> SEQ ID NO 11
<211> LENGTH: 300
<212> TYPE: PRT
<213> ORGANISM: Homo sapiens

<400> SEQUENCE: 11

Met Ala Lys Tyr Gly Glu His Glu Ala Ser Pro Asp Asn Gly Gln Asn
1               5                   10                  15

Glu Phe Ser Asp Ile Ile Lys Ser Arg Ser Asp Glu His Asn Asp Val
            20                  25                  30

Gln Lys Lys Thr Phe Thr Lys Trp Ile Asn Ala Arg Phe Ser Lys Ser
        35                  40                  45

Gly Lys Pro Pro Ile Asn Asp Met Phe Thr Asp Leu Lys Asp Gly Arg
    50                  55                  60

Lys Leu Leu Asp Leu Leu Glu Gly Leu Thr Gly Thr Ser Leu Pro Lys
65                  70                  75                  80

Glu Arg Gly Ser Thr Arg Val His Ala Leu Asn Asn Val Asn Arg Val
                85                  90                  95

Leu Gln Val Leu His Gln Asn Asn Val Glu Leu Val Asn Ile Gly Gly
            100                 105                 110

Thr Asp Ile Val Asp Gly Asn His Lys Leu Thr Leu Gly Leu Leu Trp
        115                 120                 125

Ser Ile Ile Leu His Trp Gln Val Lys Asp Val Met Lys Asp Ile Met
    130                 135                 140

Ser Asp Leu Gln Gln Thr Asn Ser Glu Lys Ile Leu Leu Ser Trp Val
145                 150                 155                 160

Arg Gln Thr Thr Arg Pro Tyr Ser Gln Val Asn Val Leu Asn Phe Thr
                165                 170                 175

Thr Ser Trp Thr Asp Gly Leu Ala Phe Asn Ala Val Leu His Arg His
            180                 185                 190

Lys Pro Asp Leu Phe Ser Trp Asp Lys Val Val Lys Met Ser Pro Ile
        195                 200                 205

Glu Arg Leu Glu His Ala Phe Ser Lys Ala Gln Thr Tyr Leu Gly Ile
    210                 215                 220

Glu Lys Leu Leu Asp Pro Glu Asp Val Ala Val Arg Leu Pro Asp Lys
225                 230                 235                 240

Lys Ser Ile Ile Met Tyr Leu Thr Ser Leu Phe Glu Val Leu Pro Gln
                245                 250                 255

Gln Val Thr Ile Asp Ala Ile Arg Glu Val Glu Thr Leu Pro Arg Lys
            260                 265                 270

Tyr Lys Lys Glu Cys Glu Glu Ala Ile Asn Ile Gln Ser Thr Ala
        275                 280                 285

Pro Glu Glu Glu His Glu Ser Pro Arg Ala Glu Thr
    290                 295                 300
```

-continued

```
<210> SEQ ID NO 12
<211> LENGTH: 300
<212> TYPE: PRT
<213> ORGANISM: Mus sp.
<220> FEATURE:
<221> NAME/KEY: SITE
<222> LOCATION: (239)..(250)
<223> OTHER INFORMATION: Precise residue is left open

<400> SEQUENCE: 12

Met Ala Lys Tyr Gly Glu His Glu Ala Ser Pro Asp Asn Gly Gln Asn
  1               5                  10                  15

Glu Phe Ser Asp Ile Ile Glu Ser Arg Ser Asp Glu His Asn Asp Val
                 20                  25                  30

Gln Lys Lys Thr Phe Thr Lys Trp Ile Asn Ala Arg Phe Ser Lys Ser
             35                  40                  45

Gly Lys Pro Pro Ile Ser Asp Met Phe Ser Asp Leu Lys Asp Gly Arg
 50                  55                  60

Lys Leu Leu Asp Leu Leu Glu Gly Leu Thr Gly Thr Ser Leu Pro Lys
 65                  70                  75                  80

Glu Arg Gly Ser Thr Arg Val His Ala Leu Asn Asn Val Asn Arg Val
                 85                  90                  95

Leu Gln Val Leu His Gln Asn Asn Val Asp Leu Val Asn Ile Gly Gly
            100                 105                 110

Thr Asp Ile Val Asp Gly Asn Pro Lys Leu Thr Leu Gly Leu Leu Trp
        115                 120                 125

Ser Ile Ile Leu His Trp Gln Val Lys Asp Val Met Lys Asp Ile Met
130                 135                 140

Ser Asp Leu Gln Gln Thr Asn Ser Glu Lys Ile Leu Leu Ser Trp Val
145                 150                 155                 160

Arg Gln Thr Thr Arg Pro Tyr Ser Gln Val Asn Val Leu Asn Phe Thr
                165                 170                 175

Thr Ser Trp Thr Asp Gly Leu Ala Phe Asn Ala Val Leu His Arg His
            180                 185                 190

Lys Pro Asp Leu Phe Ser Trp Asp Arg Val Val Lys Met Ser Pro Ile
        195                 200                 205

Glu Arg Leu Glu His Ala Phe Ser Lys Ala His Thr Tyr Leu Gly Ile
    210                 215                 220

Glu Lys Leu Leu Asp Pro Glu Asp Val Ala Val His Leu Pro Xaa Xaa
225                 230                 235                 240

Xaa Xaa Xaa Xaa Xaa Xaa Xaa Xaa Xaa Val Glu Val Leu Pro Gln
                245                 250                 255

Gln Val Thr Ile Asp Ala Ile Arg Glu Val Glu Thr Leu Pro Arg Lys
            260                 265                 270

Tyr Lys Lys Glu Cys Glu Glu Glu Ile His Ile Gln Ser Ala Val
        275                 280                 285

Leu Ala Glu Glu Gly Gln Ser Pro Arg Ala Glu Thr
    290                 295                 300

<210> SEQ ID NO 13
<211> LENGTH: 300
<212> TYPE: PRT
<213> ORGANISM: Rattus sp.

<400> SEQUENCE: 13

Met Ala Lys Tyr Gly His Leu Glu Ala Ser Pro Asp Asp Gly Gln Asn
  1               5                  10                  15
```

-continued

```
Gln Phe Ser Asp Ile Ile Lys Ser Arg Ser Asp Glu His Asn Asp Val
                 20                  25                  30

Gln Lys Lys Thr Phe Thr Lys Trp Ile Asn Ala Arg Phe Ser Lys Ser
             35                  40                  45

Gly Lys Pro Pro Ile Asn Asp Met Phe Ser Asp Leu Lys Asp Gly Arg
         50                  55                  60

Lys Leu Leu Asp Leu Leu Glu Gly Leu Thr Gly Thr Ser Leu Pro Lys
 65                  70                  75                  80

Glu Arg Gly Ser Thr Arg Val His Ala Leu Asn Asn Val Asn Arg Val
                 85                  90                  95

Leu Gln Val Leu His Gln Asn Asn Val Glu Leu Val Asn Ile Gly Gly
                100                 105                 110

Thr Asp Ile Val Asp Gly Asn Pro Lys Leu Thr Leu Gly Leu Leu Trp
            115                 120                 125

Ser Ile Ile Leu His Trp Gln Val Lys Asp Val Met Lys Asp Ile Met
145                 150                 155                 160

Arg Gln Thr Thr Arg Pro Tyr Ser Gln Val Asn Val Leu Asn Phe Thr
                165                 170                 175

Thr Ser Trp Thr Asp Gly Leu Ala Phe Asn Ala Val Leu His Arg His
            180                 185                 190

Lys Pro Asp Leu Phe Ser Trp Asp Arg Val Val Lys Met Ser Pro Thr
        195                 200                 205

Glu Arg Leu Glu His Ala Phe Ser Lys Ala His Thr Tyr Leu Gly Ile
    210                 215                 220

Glu Lys Leu Leu Asp Pro Glu Asp Val Ala Val Gln Leu Pro Asp Lys
225                 230                 235                 240

Lys Ser Ile Ile Met Tyr Leu Ser Leu Phe Glu Val Leu Pro Gln
                245                 250                 255

Gln Val Thr Ile Asp Ala Ile Arg Glu Val Glu Thr Leu Pro Arg Lys
            260                 265                 270

Tyr Lys Lys Glu Cys Glu Gly Glu Ile Asn Ile Gln Ser Ala Val
        275                 280                 285

Leu Thr Glu Glu Gly Gln Ser Pro Arg Ala Glu Thr
    290                 295                 300

<210> SEQ ID NO 14
<211> LENGTH: 22
<212> TYPE: DNA
<213> ORGANISM: Mus sp.

<400> SEQUENCE: 14
gattgtggat gaaaacagtg gg                                              22

<210> SEQ ID NO 15
<211> LENGTH: 12
<212> TYPE: PRT
<213> ORGANISM: Homo sapiens

<400> SEQUENCE: 15

Asp Lys Lys Ser Ile Ile Met Tyr Leu Thr Ser Leu
  1               5                  10
```